United States Patent [19]

Pastan et al.

[11] Patent Number: 5,981,726
[45] Date of Patent: Nov. 9, 1999

[54] CHIMERIC AND MUTATIONALLY STABILIZED TUMOR-SPECIFIC B1, B3 AND B5 ANTIBODY FRAGMENTS; IMMUNOTOXIC FUSION PROTEINS; AND USES THEREOF

[75] Inventors: Ira Pastan, Potomac; Itai Benhar, Rockville, both of Md.

[73] Assignee: The United States of America as represented by the Department of Health and Human Services, Washington, D.C.

[21] Appl. No.: 08/331,397

[22] Filed: Oct. 28, 1994

Related U.S. Application Data

[63] Continuation-in-part of application No. 07/767,331, Sep. 30, 1991, abandoned, which is a continuation-in-part of application No. 07/596,289, Oct. 12, 1990, Pat. No. 5,242,813.

[51] Int. Cl.$^6$ .......................... A61K 39/395; C07M 21/04
[52] U.S. Cl. .................................. 536/23.53; 530/387.3; 530/387.7; 530/389.7; 530/391.7; 424/133.1; 424/135.1; 424/138.1; 424/155.1; 424/174.1; 424/181.1; 424/183.1; 435/328; 435/344; 435/69.6; 435/69.7; 435/91.1; 536/23.4
[58] Field of Search .............................. 530/387.1, 387.3, 530/387.5, 387.7, 388.1, 388.8, 390.5, 866, 867, 389.7, 391.7; 435/69.1, 69.7, 91.1, 69.6, 328, 344; 536/23.53, 23.4; 424/174.1, 181.1, 183.1, 133.1, 135.1, 138.1, 155.1

[56] References Cited

U.S. PATENT DOCUMENTS

| 4,545,985 | 10/1985 | Pastan et al. |           |
|-----------|---------|---------------|-----------|
| 5,242,813 | 9/1993  | Pastan et al. | 435/70.21 |
| 5,258,498 | 11/1993 | Houston et al.| 530/350   |

FOREIGN PATENT DOCUMENTS

WO 9307286  4/1993  WIPO.

OTHER PUBLICATIONS

Proceedings of the National Academy of Sciences of the USA, vol. 88, No. 19, Oct. 1,1991 Washington DC, USA, pp. 8616–8620, U. Brinkmann et al. 'B3 (Fv)–PE38KDEL, a single–chain immunotoxin that causes complete regression of a human carcinoma in mice', cited in the application, see abstract, see figures 1,2.

Bioconjugate Chemistry, vol. 5, No. 4, Jul. 1994 Washington, DC, USA, pp. 321–326, XP 000564453 I. Benhar et al. 'Mutations of two lysine residues in the CDR loops of a recombinant immunotoxin that reduce its sensitivity to chemical derivatization.', cited in the application, see abstract, see figure 1.

Cancer Research, vol. 53, No. 2, Jan. 15, 1993 Philadelphia, PA, USA, pp. 334–339, P. Friedman et al. 'BR96 sFv–PE40, a potent single–chain immunotoxin that selectively kills carcinoma cells.', see abstract, see discussion.

The Journal of Immunology, vol. 152, No. 5, Mar. 1, 1994 Baltimore, MD, USA, pp. 2377–2384, C. Siegall et al., 'In vitro and in vivo characterization of BR96 sFv–PE40.' see abstract.

Bast et al. *J. Clin. Invest.*, 68: 1331–1337 (1981).

Batra et al., *J. Biol. Chem.*, 265: 15198–15202 (1990).

Batra et al., *Proc. Natl. Acad. Sci. USA* 86: 8545–8549 (1989).

Bird et al., *Science*, 242: 423–26 (1988).

Brinkmann et al. *Proc. Natl. Acad. Sci. USA*, 89: 3075–3079 (1992).

Brinkmann and Pastan, *Biochem. Biophys. Acta.*, 1198: 27–45 (1994).

Chaudhary et al., *Proc. Natl. Acad. Sci. USA* 87: 9491–9494 (1990).

Chaudhary et al., *Proc. Natl. Acad. Sci. USA* 87: 1066–1070 (1990).

Chaudhary et al., *Nature*, 339: 394–397 (1989).

Hartman et al. *E.M.B.O.J.* 3: 3023–3030 (1984).

Hellstrom et al. *Cancer Res.*, 50: 2183–2190 (1990).

Hoess et al., *Gene*, 128: 43–49 (1993).

Houston et al., *Proc. Natl. Acad. Sci. USA*, 85: 5879–5883 (1988).

Kondo et al., *J. Biol. Chem.*, 263: 9470–9475 (1988).

Pai et al., *Proc. Natl. Acad. Sci. USA*, 88: 3358–3362 (1991).

Pastan et al. *Cancer Res.*, 51: 3781–3787 (1991).

Willingham et al. *Proc. Natl. Acad. Sci. USA*, 84: 2474–2478 (1987).

*Primary Examiner*—Paula K. Hutzell
*Assistant Examiner*—Julie E Burke
*Attorney, Agent, or Firm*—Townsend and Townsend and Crew LLP

[57] ABSTRACT

This invention provides for recombinant single chain antibodies capable of specifically binding to a Lewis$^Y$-related carbohydrate antigen and fusion proteins comprising these antibodies. More particularly, the invention provides for single chain Fv regions of the monoclonal antibodies B1 and B5. The invention also provides for a number of stabilizing mutations of the Lewis$^Y$-binding monoclonal antibody B3. In addition, the invention provides for methods of detecting cells bearing a Lewis$^Y$ antigen in a patient and for methods of killing or inhibiting the growth of cells bearing a Lewis$^Y$ antigen in a patient.

3 Claims, 17 Drawing Sheets

```
                                      NdeI  |----Fv HEAVY CHAIN--
  1 TTTAACTTTAAGAAGGAGATATACATATGGATGTGAAGCTGGTGGAGTCT  50
                        SD        M  D  V  K  L  V  E  S
                                     E  V  K  L  V  E  S
--------->
 51 GGGGGAGGCTTAGTGCAGCCTGGAGGGTCCCTGAAACTCTCCTGTGCAAC 100
     G  G  G  L  V  Q  P  G  G  S  L  K  L  S  C  A  T
     G  G  G  L  V  Q  P  G  G  S  L

101 CTCTGGATTCACTTTCAGTGACTATTACATGTATTGGGTTCGCCAGACTC 150
     S  G  F  T  F  S  D  Y  Y  M  Y  W  V  R  Q  T  P

151 CAGAGAAGAGGCTGGAGTGGGTCGCATACATTAGTAATGATGATAGTTCC 200
     E  K  R  L  E  W  V  A  Y  I  S  N  D  D  S  S

201 GCCGCTTATTCAGACACTGTAAAGGGCCGGTTCACCATCTCCAGAGACAA 250
     A  A  Y  S  D  T  V  K  G  R  F  T  I  S  R  D  N

251 TGCCAGGAACACCCTCTACCTGCAAATGAGCCGTCTGAAGTCTGAGGACA 300
     A  R  N  T  L  Y  L  Q  M  S  R  L  K  S  E  D  T

301 CAGCCATATATTCCTGTGCAAGAGGACTGGCCTGGGGAGCCTGGTTTGCT 350
     A  I  Y  S  C  A  R  G  L  A  W  G  A  W  F  A
                                                  BamHI
351 TACTGGGGCCAAGGGACTCTGGTCACTGTCTCCTCAGGCGGAGGCGGATC 400
     Y  W  G  Q  G  T  L  V  T  V  S  S  G  G  G  S
           <-----Fv HEAVY CHAIN--|----------LINKER-

----------LINKER----------------|--Fv LIGHT CHAIN---
401 CGGTGGTGGCGGATCTGGAGGTGGCGGAAGCGATGTGCTGATGACCCAGT 450
     G  G  G  G  S  G  G  G  G  S  D  V  L  M  T  Q  S
                                  D  V  L  M  T  Q  S

-----Fv LIGHT CHAIN--------->
451 CTCCATTGAGTTTACCTGTCAGTCTTGGAGATCAAGCCTCCATCTCTTGC 500
     P  L  S  L  P  V  S  L  G  D  Q  A  S  I  S  C
     P  L  S  L  P  V  S  L  G  ?  Q

501 AGATCTAGTCAGATCATTGTACATAGTAATGGAAACACCTATTTAGAATG 550
     R  S  S  Q  I  I  V  M  S  N  G  N  T  Y  L  E  W

551 GTACCTGCAGAAACCAGGCCAGTCTCCAAAGCTCCTGATCTACAAAGTTT 600
     Y  L  Q  K  P  G  Q  S  P  K  L  L  I  Y  K  V  S
```

FIG. 2A-1.

601 CCAACCGATTTTCTGGGGTCCCAGACAGGTTCAGTGGCAGTGGATCAGGG 650
    N   R   F   S   G   V   P   D   R   F   S   G   S   G   S   G

651 ACAGATTTCACACTCAAGATCAGCAGAGTGGAGGCTGAGGATCTGGGAGT 700
    T   D   F   T   L   K   I   S   R   V   E   A   E   D   L   G   V

701 TTATTACTGCTTTCAAGGTTCACATGTTCCATTCACGTTCGGCTCGGGGA 750
    Y   Y   C   F   Q   G   S   N   V   P   F   T   F   G   S   G   T

HindIII
751 CAAAGCTGGAAATTAAAGCTTT........                    772
    K   L   E   I   K   A   F -> PE40

FIG. 2A-2.

721 CACATGTTCCATTCACGTTCGGCTCGGGGACAAAGCTGGAAATTAAATAA 770
    H   V   P   F   T   F   G   S   G   T   K   L   E   I   K   *

EcoRI
771 TGAATTCC..                                        779
    * -> TERM

FIG. 2B.

```
                    11      16                    CDR1                    40 42 44                        CDR2
                    |       |                                              |  | |
B3VH       DVKLVESGGGLVQPGGSLKLSCATSGFTFS DYYMY WVRQTPEKRLEWVA YISNDDSSAAYSDTVKG
56P1'CL    QVELVESGGGVVQPGRSLRLSCAASGFTFS SYAMH WVRQAPGKGLEWVA VISYDGSNKYYADSVKG
HumB3VH    DVKLVESGGGVVQPGRSLKLSCATSGFTFS DYYMY WVRQAPGKGLEWVA YISNDDSSAAYSDRVKG
            *   *                                                  *

74 75  82a 82b 83 84                    CDR3
               | |    |   |  |  |
B3VH       RFTISTDNARNTLYLQMSRLKSEDRAIYSCAR GLAWGAWFAY    WGQGTLVTVSS
56P1'CL    RFTISRDNSKNTLYLQMNSLRAEDTAVYYCAR RSARTYYFDY    WGQGTLVTVSS
HumB3VH    RFTISRDNSKNTLYLQMNSLRAEDTAIYSCAR TLAWTAWRAY    WGQGTLVTVSS
                                         *  *

FIG. 11A.

14 15 17 18                CDR1                                 45           CDR2
               |  |  | |                                                      |
B3VL       DVLMTQSPLSLPVSLGDQASISC RSSQIIVHSNGNTYLE WYLQKPGQSPKLLIY KVSNRFS
GM607      DIVMTQSPLSLPVTPGEPASISC RSSQSLLHSNGYNYLD WYLQKPGQSPQLLIY LGSNRAS
HumB3VL    DVLMTQSPLSLPVTPGEPASISC RSSQIIVHSNGNTYLE WYLQKPGQSPQLLIY KVSNRFS
            *  *                                                    *

83             CDR3    100 104
                                  |                       |   |
B3VL       GVPDRFSGSGSGTDFTLKISRVEAEDLGVYYC FQFSHVPFT FGSGTKLEIK
GM607      GVPDRFSGSGSGTDFTLKISRVEAEDVGVYYC MQGLQTPQT FGQGTKVEIK
HumB3VL    GVPDRFSGSGSGTDFRLKISRVEAEDVGVYYC FQFSHVPFT FGQGTKVEIK

FIG. 11B.
```

—◯— B3(Fv)PE38  —□— B3V$_H$-HUMV$_L$-PE38
—△— B3HUMV$_H$-V$_L$-PE38  —●— B3HUMV$_H$-HUMV$_L$-PE38
—▲— HUMB3(Fv)PE38

```
GAGGTGCAGCTGGTGGAATCTGGAGGAGGCTTAGTGAAGCCTGGAGGGTCCCTGAAA
 E   V   Q   L   V   E   S   G   G   G   L   V   K   P   G   G   S   L   K
 E   V   Q   L   V   E   S   G   G   G   L   V   K   P   G   G   S   L
CTCTCCTGTGCAGCCTCTGGATTCATTTTCAGTGACAATTACATGTATTGGGTTCGC
 L   S   C   A   A   S   G   F   I   F   S   D   N   Y   M   Y   W   V   R
                                         ─────────────────
                                              CDR 1
CAGACTCCGGAGAAGAGGCTGGAGTGGGTCGCAACCATTAGTGATGGTGGCACTTAT
 Q   T   P   E   K   R   L   E   W   V   A   T   I   S   D   G   G   T   Y
                                             ────────────────────
                                                      CDR 2
ATCGACTATTCAGACAGTGTGAAGGGGCGATTCACCATCTCCAGAGACAATGCCAAG
 I   D   Y   S   D   S   V   K   G   R   F   T   I   S   R   D   N   A   K
 ─────────────────────────────

AATAATCTGTACTTGCAAATGAGCAGTCTGAGGTCTGAGGACACAGGCATGTATTAT
 N   N   L   Y   L   Q   M   S   S   L   R   S   E   D   T   G   M   Y   Y

TGTGGAAGGAGTCCGATCTACTATGATTACGCCCCGTTTACTTACTGGGGCCAAGGG
 C   G   R   S   P   I   Y   Y   D   Y   A   P   F   T   Y   W   G   Q   G
             ──────────────────────────────────────
                        CDR 3
ACTCTGGTCACTGTCTCTGCAGCCAAAACGACACCCCCATCTGTCTATCCACTGGCC
 C   L   V   T   V   S   A   A̶   K̶   T̶   T̶   P̶   P̶   S̶   V̶   Y̶   P̶   L̶   A̶

CCTGGATCTGCT
 P̶   G̶   S   A                    FIG. 15A.
```

```
GATGTTGTGATGACCCAGACTCCACTCTCCCTGCCTGTCAGTCTTGGAGATCAAGCC
 D   V   V   M   T   Q   T   P   L   S   L   P   V   S   L   G   D   Q   A
 D   V   V   M   T   Q   T   P   L   S   L   P   V   S   L   G   D
TCCATCTCTTGCAGATCTAGTCAAAACCTTGTACACAGTGATGGAAAAACCTATTTA
 S   I   S   C   R   S   S   Q   N   L   V   H   S   D   G   K   T   Y   L
                 ──────────────────────────────────────
                                  CDR 1
CATTGGTTCCTGCAGAAGCCTGGCCAGTCTCCAACGCTCCTGATCTACAAAGTTTCC
 H   W   F   L   Q   K   P   G   Q   S   P   T   L   L   I   Y   K   V   S
 ─                                                       ───────────
                                                            CDR 2
AACCGATTTTCTGGGGTCCCAGACAGGTTCAGTGGCAGTGGATCAGGGACAGATTTC
 N   R   F   S   G   V   P   D   R   F   S   G   S   G   S   G   T   D   F
 ────────────

ATACTCAAGATCAGCAGAGTGGAGGCTGAGGATCTGGGAGTTTATTTCTGCTCTCAA
 I   L   K   I   S   R   V   E   A   E   D   L   G   V   Y   F   C   S   Q
                                                             ───────

AGTACACATGTTCCGCTCACGTTCGGTGCTGGGACCAAGCTGGAGCTGAAACGGGCT
 S   T   H   V   P   L   T   F   G   A   G   T   K   L   E   L   K   R̶   A̶
 ───────────────
    CDR 3
GATGCTGCACCAACTGTATCCATCTTCCCACCA
 D̶   A̶   A̶   P̶   T̶   V̶   S̶   I̶   F̶   P̶   P̶
                         FIG. 15B.
```

```
GAGGTGAAGCTGGTGGAATCTGGAGGAGGCTTAGTGCAGCCTGGAGGGTCCCTGAAA
 E   V   K   L   V   E   S   G   G   G   L   V   Q   P   G   G   S   L   K
 E   V   K   L   V   E   S   G   G   G   L   V   Q   P   G
CTCTCCTGTGCAACCTCTGGATTTACTTTCAGTGACTATTACATGTATTGGGTTCGC
 L   S   C   A   T   S   G   F   T   F   S   D   Y   Y   M   Y   W   V   R
                                         CDR 1
CAGACTCCAGAGAAGAGGCTGGAGTGGGTCGCATACATTAGTAATGGTGGTGGTAGC
 Q   T   P   E   K   R   L   E   W   V   A   Y   I   S   N   G   G   S
                                              CDR 2
ACCTATTATCCAGACACTGTAAAGGGCCGATTCACCATCTCCAGAGACAACGCCAAG
 T   Y   Y   P   D   T   V   K   G   R   F   T   I   D   R   D   N   A   K

AACACCCTGTACCTGCAGATGAGCCGTCTGAAGTCTGAGGACACAGCCATGTATTAC
 N   T   L   Y   L   Q   M   S   R   L   K   S   E   D   T   A   M   Y   Y

TGTGCAAGGGGGCTCTCTGATGGTTCCTGGTTTGCTTACTGGGGCCAAGGGACTCTG
 C   A   R   G   L   S   D   G   S   W   F   A   Y   W   G   Q   G   T   L
             CDR 3
GTCACTGTCTCCTCAGGCGGAGGCGGATCCGGT
 V   T   V   S   S   G   G   G   G   S   G
```

FIG. 16A.

```
GATGTTTTGTTGACCCAAACTCCACTCTCCCTGCCTGTCAGTCTTGGAGATCAAGCC
 D   V   L   L   T   Q   T   P   L   S   L   P   V   S   L   G   D   Q   A
 D   V   L   L   T   Q   T   P   L   S   L   P   V   S   L
TCTATTTCTTGTAGATCTAGTCAGAGCATTGTACATAGTAATGGAAACACCTATTTA
 S   I   S   C   R   S   S   Q   S   I   V   H   S   N   G   N   T   Y   L
                     CDR 1
GAATGGTACCTGCAGAAACCAGGCCAGTCTCCAAAGCTCCTGATCTACAAAGTTTCC
 E   W   Y   L   Q   K   P   G   Q   S   P   K   L   L   I   Y   K   V   S
                                                        CDR 2
AACCGATTTTCTGGGGTCCCAGACAGGTTCAGTGGCAGTGGATCAGGGACAGATTTC
 N   R   F   S   G   V   P   D   R   F   S   G   S   G   S   G   T   D   F

ACACTCAAGATCAGCAGAGTGGAGGCTGAGGATCTGGGAGTTTATTACTGCTTTCAA
 T   L   K   I   S   R   V   E   A   E   D   L   G   V   Y   Y   C   F   Q

GGTTCACATGTTCCATTCACGTTCGGCTCGGGGACAAAGTTGGAAATAAAGCGGGCT
 G   S   H   V   P   F   T   F   G   S   G   T   K   L   E   I   K   R   A
     CDR 3
GATGCTGCACCAACTGTATCCATCTTCCCACCA
 D   A   A   P   T   V   S   I   F   P   P
```

FIG. 16B.

VH:
DVKLVESGGGLVQPGGSLKLSCATSGFTFS (DYYMY) WVRQTPEKRLEWVA (YISNDDSSAAYSDTVKG)
RFTISRDNARNTLYLQMSRLKSEDTAIYSCAR (GLAWGAWFAY) WGQGTLVTVSS

LINKER:
GGGGSGGGGSGGGGS

VL:
DVLMTQSPLSLPVSLGDQASISC (RSSQIIVHSNGNTYLE) WYLQKPGQSPKLLIY (KVSNRFS)
GVPDRFSGSGSGTDFTLKISRVEAEDLGVYYC (FQGSHVPFT) FGSGTKLEIK

FIG. 17.

VH:
GATGTGAAGCTGGTGGAGTCTGGGGGAGGCGTCTGTGCAGCCCGGGGCCTCCCTGAAACTCTCCTGTGCAACCTCTG
GATTCACTTTCAGTGACTATTACATGTATTGGGTTCGCCAGGCCCCTGAGTGGGTCGCATACAT
TAGTAATGATGATAGTTCCGCCGCTTATTCAGATGATAGTTCCACCATCTCTAGAGACAATAGCAAG
AACACCCTCTACCTGCAAATGAACCGTCTGCGCGCCAGCACACAGCCATATATTCCTGTCAAGAGAGACTGGCCT
GGGGAGCCTGGTTTGCTTACTGGGGCCAAGGGACTCTGGTCACTGTCTCCTCA

LINKER: ggcggaggcggatccggtggtggcggatctggaggtggcggaagc

VL:
GATGTGCTGATGACCCAGTCTCCATTGAGTTTACCTGTCACCCCGGGAGAGCCGGCCTCCATCTCTTGCAGATCTA
GTCAGATCATTGTACATAGTAATGGAAACACCTATTTAGAATTGGAAAACCAGGCCAGTCTCCACAGCT
GCTGATCTACAAAGTTTCCAACCGATTTTCTGGGGTCCCAGACAGGTTCAGTGGCAGTCAGGGACAGATTTC
ACACTCAAGATCAGCAGAGTGAGGCTGAGGACGTCGGAGTTTATTACTGCTTTCAAGGTTCACATGTTCCATTCA
CGTTCGGCCAGGGTACCAAGGTCGAAATTAAA

FIG. 18.

CHIMERIC AND MUTATIONALLY STABILIZED TUMOR-SPECIFIC B1, B3 AND B5 ANTIBODY FRAGMENTS; IMMUNOTOXIC FUSION PROTEINS; AND USES THEREOF

The present application is a continuation-in-part of U.S. patent application Ser. No. 07/767,331, filed on Sep. 30, 1991, now abandoned, which is a continuation-in-part of U.S. patent application Ser. No. 07/596,289 filed on Oct. 12, 1990, now U.S. Pat. No. 5,242,813, issued on Sep. 7, 1993, both of which are hereby incorporated by reference.

BACKGROUND OF THE INVENTION

The subject invention relates to tumor-specific recombinant antibody fragments, to molecules incorporating such fragments such as immunotoxins and to uses thereof. Exemplary embodiments of the invention include immunotoxins comprising Pseudomonas exotoxins fused to the Fv regions of monoclonal antibodies B1, B3, and B5 which have tumor specificity and which may be used in the treatment of mammalian cancer.

Monoclonal antibodies B1, B3, and B5 are recently isolated murine antibodies directed against a carbohydrate antigen in the Lewis$^Y$ (Le$^Y$) family (Pastan et al. Cancer Res., 51: 3781–3787 (1991)). The Le$^y$ antigens are found on the surface of many mucinous carcinomas of the colon, stomach, ovaries, breast, lung as well as some epidermal carcinomas. Because they react with only a limited number of normal tissues, these antibodies are ideal candidates for use in the treatment and diagnosis of cancer.

In order to create a cytotoxic agent that specifically attacks cancer cells, an antibody or its fragments may be used as the targeting moiety of an immunotoxin. In such immunotoxins, the targeting moiety typically replaces the cell binding domain of a cytotoxin molecule (e.g. domain I of Pseudomonas exotoxin (PE) or the B chain of Diphtheria toxin) and acts to specifically direct the cytotoxin to its target cell (as determined by the specificity of the targeting moiety). As a result, only cells which are recognized by the targeting moiety are efficiently killed and cells which are not recognized are spared (for a review see Brinkmann and Pastan, Biochem. Biophys. Acta., 1198: 27–45 (1994)).

Immunotoxins were first made by chemically coupling antibodies to cytotoxic molecules. Thus, for example, monoclonal antibody B3 has been chemically coupled to at least two different forms of Pseudomonas exotoxin (PE) (U.S. Pat. No. 4,545,985). One of these is the full length toxin (PE) and the other a truncated derivative (PE40) (Kondo et al., J. Biol. Chem., 263: 9470–75 (1988) and Pai et al., supra). Both of these immunotoxins have been shown to be selectively cytotoxic to tumor cells that contain the B3 antigen on their surface, and these immunotoxins have been shown to cause complete tumor regression in mice bearing human tumor xenografts (Pai et al., Proc. Natl. Acad. Sci. USA, 88: 3358–62 (1991)).

Although chemically coupled immunotoxins are useful they have several undesirable properties. For example, the chemical modifications can change the antibody and affect its binding to the antigen. Furthermore, the purified immunotoxins are a heterogeneous mixture of antibody-toxin molecules connected to each other via different positions on the antibody and the toxin. Thus, Pseudomonas exotoxin, for example, can be coupled either to the light- or heavy-chain of the antibody and to different positions on each of these chains.

To overcome the limitations of chemically conjugated immunotoxins, chimeric immunotoxins have been made as recombinant, single chain, antibody-toxin fusion proteins. It has been shown that certain single chain antigen binding proteins made from the Fv portions of the heavy and light chain of antibodies held together by a polypeptide linker can have the same binding properties as their full length two chain counterparts (Bird et al., Science, 242: 423–26 (1988) and Huston et al., Proc. Natl. Acad. Sci. USA, 85: 5879–83 (1988)). It has also been shown that, in some cases, fusion proteins composed of single chain antibodies linked to toxins may retain the binding capacity of the single chain antibody as well as the activity of the toxin (Chaudhary et al., Nature, 339: 394–97 (1989); Batra et al., J. Biol. Chem., 265: 15198–15202 (1990); Batra et al., Proc. Natl. Acad. Sci. USA 86: 8545–8549 (1989); Chaudhary et al., Proc. Natl. Acad. Sci. USA 87: 1066–1070 (1990)).

Receptor proteins have often been used as immunotoxin targets because they are cell surface proteins which are often overexpressed in various cancers (Brinkmann and Pastan, Biochem. Biophys. Acta., 1198: 27–45 (1994)) and thus provide cancer-specific targets. For example, single chain immunotoxins have been made consisting of the Fv domain of an antibody directed at the interleulin 2 receptor (Chaudhary et al., Nature, 339: 394–97 (1989) and Batra et al., J. Biol. Chem. 265: 15198–15202 (1990)) or at the transferrin receptor (Batra et al., Proc. Natl. Acad. Sci. USA 86: 8545–49 (1989)) fused to truncated forms of PE or diphtheria toxin (Chaudhary et al., Proc. Natl. Acad. Sci. USA 87:9491–94 (1990)). Although receptor proteins are overexpressed on many cancers, they may still be present on healthy cells and therefore often do not provide the defined cancer specificity desired for an immunotoxin.

Since the number of antibodies that react preferentially with carcinomas is limited, the identification and characterization of additional "cancer specific" antibodies that would react with all or most of the cells in a tumor and with relatively few normal cells and tissues is desirable. In addition, recombinant immunotoxins are known to degrade over time both in vitro and in vivo. It would be desirable to obtain immunotoxins that show a reduced rate of degradation and therefore require less frequent administration. Finally, with repeated use, murine antibodies and fusion proteins containing murine antibodies, like any other foreign protein, may ultimately prove immunogenic and invoke an immune response in the treated organism. It would be desirable to produce targeting moieties and immunotoxins having reduced antigenic potential. As will be explained herein, these advantages and others are provided by the present invention.

SUMMARY OF THE INVENTION

The present invention provides for recombinant single chain antibodies and fusion proteins such as immunotoxins employing these antibodies. In particular, this invention provides for recombinantly produced antibodies comprising the variable light and heavy (Fv) chain regions of antibodies that have the binding specificity of monoclonal antibody B1 or B5 as described below. These antibodies provide carcinoma-specific targeting moieties suitable for use in cytotoxic fusion proteins.

In one embodiment, this invention provides for single-chain antibodies comprising an Fv region of both the variable light ($V_L$) and variable heavy ($V_H$) chain regions of an antibody where the single-chain antibody has the binding specificity of monoclonal antibody B1 or B5. Particularly preferred are single chain antibodies B1Fv) and B5(Fv).

This invention also provides for single-chain B3 antibodies having various mutations that increase the stability of the antibody. Particularly preferred mutations are in the $V_L$ chain and include a mutation of methionine to leucine at position 4 (B3(Fv): M4L, or a mutation of serine to threonine at position 7 (B3(Fv): S7T) or the combination of both mutations (B3(Fv): M4L S7T).

In another embodiment, this invention provides for chimeric single-chain antibodies comprising a variable heavy chain of a first antibody and a variable light chain of a second antibody where the first and second antibody are different antibodies and the heavy and light chain are recombinantly fused to form a single-chain antibody which specifically binds a lewis$^Y$ carbohydrate antigen. In a particularly preferred embodiment, the single-chain antibody has the binding specificity of monoclonal antibody B1, B3, or B5. In one embodiment, the first antibody is B1, B3, or B5. In another embodiment, the second antibody is B1, B3, or B5. Particularly preferred single chain antibodies include B5$V_H$-B$^3V_L$ and B3VH-B5$V_L$.

In any of the single chain antibodies described above, the variable heavy chain region and the variable light chain region may be joined by a linker. One particularly preferred linker is (Gly$_4$Ser)$_3$ (SEQ ID NO: 32).

Any of the single-chain antibodies described above may also be incorporated into single-chain fusion proteins. The fusion proteins preferably comprise the single-chain antibody recombinantly fused to an effector molecule. The effector molecule may be a cytotoxin such as Pseudomonas exotoxin and more preferably is either PE38, PE40, PE38KDEL, or PE38REDL. Thus, particularly preferred fusion proteins include B1(Fv)-PE38, B1(Fv)-PE40, B1(Fv)-PE38KDEL, B1(Fv)-PE38REDL, B5(Fv)-PE38, B5(Fv)-PE40, B5(Fv)-PE38KDEL, B5(Fv)-PE38REDL, B3(Fv): S7T-PE38, B3(Fv): S7T-PE40, B3(Fv): S7T-PE38KDEL, B3(Fv): S7T-PE38REDL, B3(Fv): M4L-PE38, B3(Fv): M4L-PE40, B3(Fv): M4L-PE38KDEL, B3(Fv): M4L-PE38REDL, B3(Fv): M4L S7T-PE38, B3(Fv): M4L S7T-PE40, B3(Fv): M4L S7T-PE38KDEL, B3(Fv): M4L S7T-PE38REDL, B5$V_H$-B3$V_L$-PE38, B5$V_H$-B3$V_L$-PE40, B5$V_H$-B3$V_L$-PE38KDEL, B5$V_H$-B3$V_L$-PE38REDL, B3$V_H$-B5$V_L$-PE38, B3$V_H$-B5$V_L$-P40, B3$V_H$-B5$V_L$-PE38KDEL, and B3$V_H$-B5$V_L$-PE38REDL, all of which are described below.

In any of the fusion proteins and antibodies described above the variable heavy region ($V_H$) and the variable light ($V_L$) chain regions may be joined by a linker. One particularly preferred linker is (Gly$_4$Ser)$_3$ (SEQ ID NO: 32). In any of the fusion proteins described above, the single-chain Fv region may be joined to the effector molecule by a connector. Peptide connectors are preferred and one particularly preferred peptide connector is SGGPEGGS (SEQ ID NO: 44).

In a preferred embodiment, each of the single-chain antibodies and fusion proteins described above may be recombinantly expressed in host cells such as E. coli that have been transformed with a nucleotide sequence encoding the single-chain antibody or fusion protein. Thus, this invention also provides for recombinant DNA molecules that encode any of the above-described antibodies or fusion proteins.

In another embodiment this invention provides for a pharmaceutical composition comprising any of the single-chain fusion proteins described above in a concentration sufficient to inhibit tumor cell growth together with a pharmaceutically acceptable carrier.

This invention similarly provides for a method of killing or inhibiting the growth of cells bearing a Lewis$^Y$ antigen in a patient. The method includes the steps of administering to the patient a pharmaceutical composition comprising any of the fusion proteins described above in an amount sufficient to kill or inhibit the growth of the cells.

This invention also provides for a method of detecting the presence or absence of a cell bearing a Lewis$^Y$ carbohydrate antigen in a patient, the method comprising the steps of removing a tissue or fluid sample from the patient, adding any of the single-chain antibodies described above to the sample, and detecting for the presence or absence of a binding complex between the antibody and the antigen.

BRIEF DESCRIPTION OF THE DRAWINGS

FIGS. 2a and 2b show the nucleotide sequences encoding the heavy and light chain Fv region of monoclonal antibody B3 (SEQ ID NO: 33). (FIG. 2a) The heavy chain Fv coding region extends from position 30 to 383, the light chain Fv gene from position 433 to 767 and the linker from 384 to 432. The deduced amino acid sequence is shown in plain letters (SEQ ID NO: 34); below in italic letters is the protein sequence determined by Edman sequencing of the antibody (SEQ ID NOS: 55 and 56). The first amino acid encoded by the cloned heavy chain Fv gene is Asp instead of Glu due to the oligonucleotide primer used at position 456–465. This is the region where the PCR cloning artifact was repaired. This sequence encodes the same amino acids as the original B3 light chain gene but uses other codons. Homology comparisons to the known nucleotide sequence of PACT Ig kappa chain (Taub et al.) J. Biol. Chem., 264: 59–65 (1989)) which is most homologous to the B3 light chain indicates that the original sequence was most probably CTCTCCCTG (SEQ ID NO: 37) instead of TTGAGTTTA (SEQ ID NO: 38). Thus the natural B3 light chain gene has a sequence repetition 5-(CCAGTCT[CC)ACTCTCC]-3' (SEQ ID NO: 39) between positions 445 and 465 which is responsible for the incorrect primer annealing in PCR. (FIG. 2b) Sequence at the 3'-end of the light chain for expression of the single chain B3(Fv) alone (SEQ ID No: 35 and amino acid Sequence SEQ ID NO: 36). (SD)—Shine Dalgarno consensus sequence; (*)—translation stop signal. (Term) transcription terminator.

Competition by monoclonal antibody B3 was performed on A431 cells as described in Example 7.

Figure 4A:
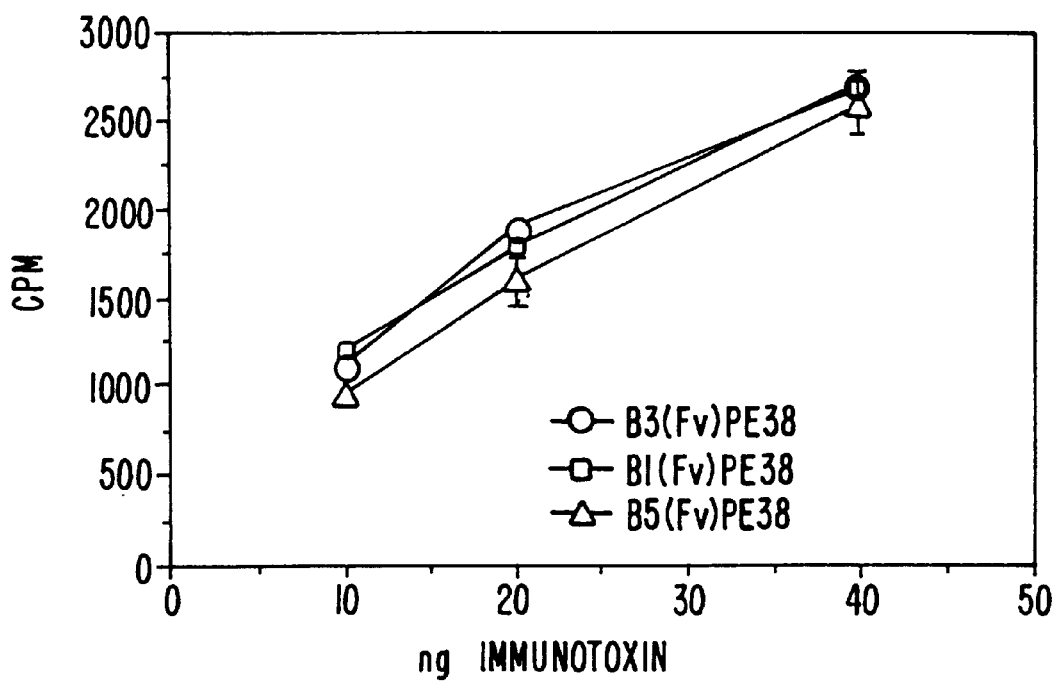
Figure 4B:
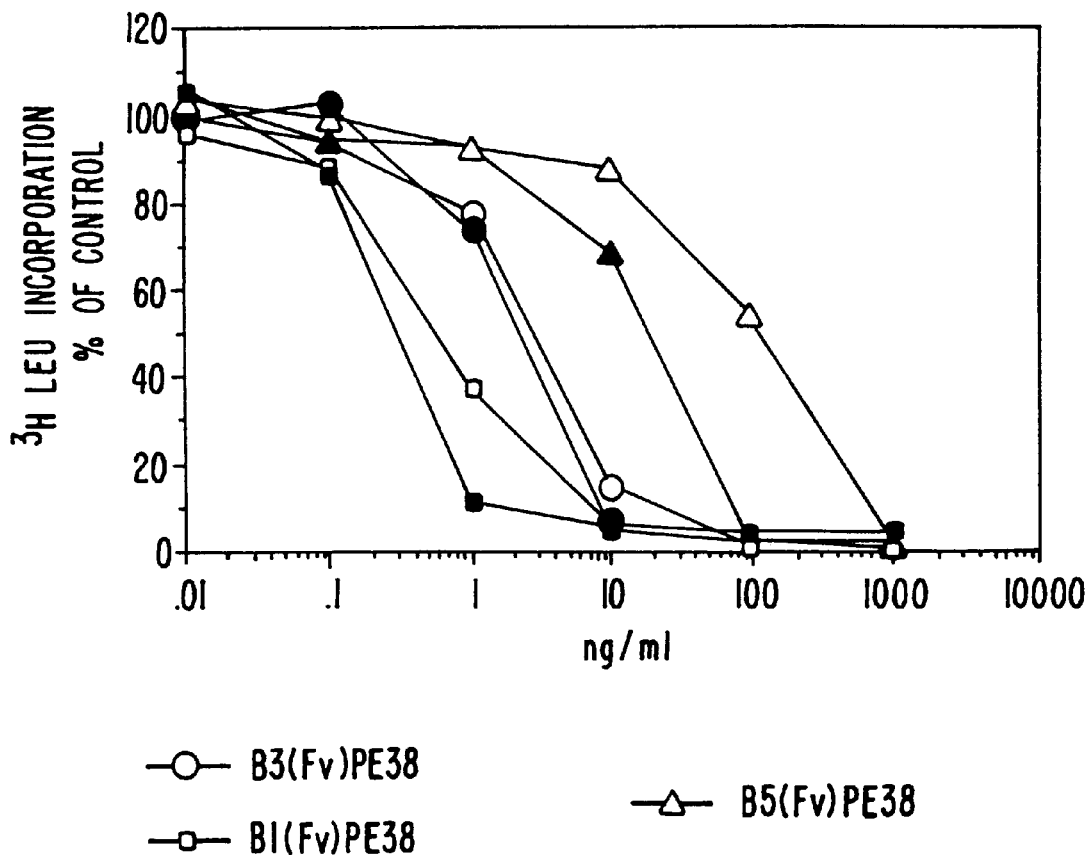

FIGS. 4a and 4b show the ADP-ribosylation and cytotoxic activities of B1(Fv)-PE38, B3(Fv)-PE38, B5(Fv)-PE38 recombinant immunotoxins. (FIG. 4a) ADP-ribosylation activity was determined by the incorporation on $^{14}$C-NAD into acid-precipitable material using elongation factor 2 enriched wheat-germ extract (Collier and Kandel, 1971). (FIG. 4b) Cytotoxicity towards A431 cells was measured by the inhibition of incorporation of 3H-leucine into cell protein, following 2 hours (open symbols) or 20 hours (solid symbols) of incubation of the cells with serial dilutions of immunotoxins in PBS+0.2% BSA.

Figure 5A:
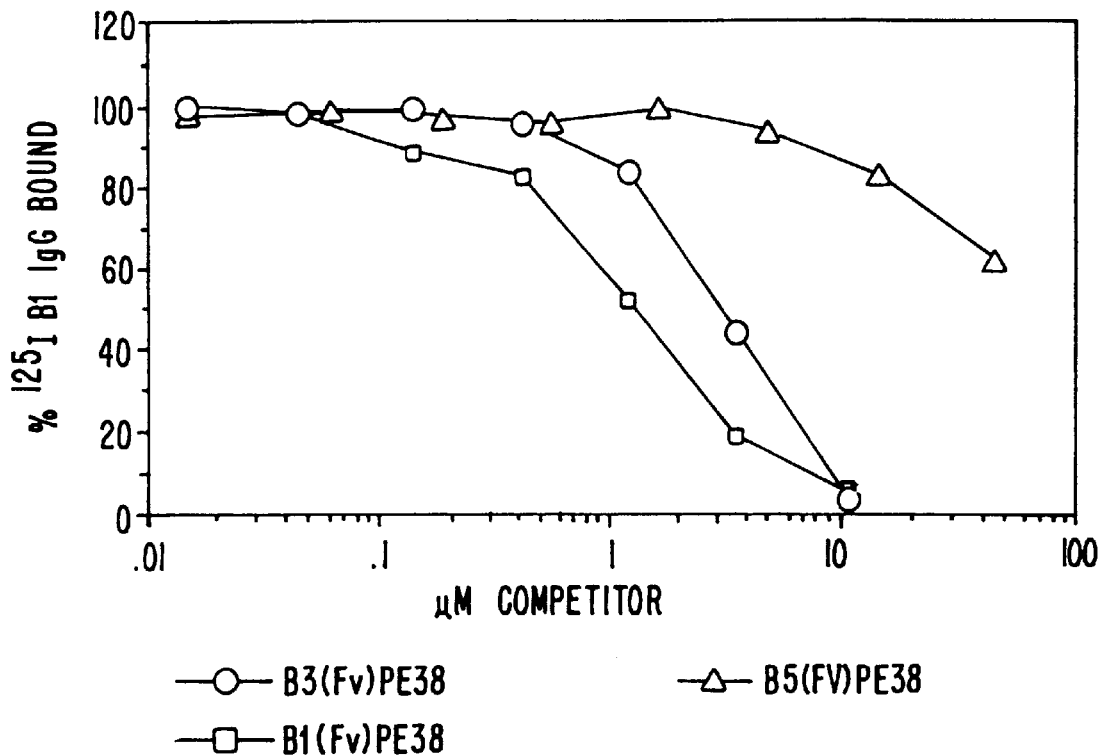
Figure 5B:
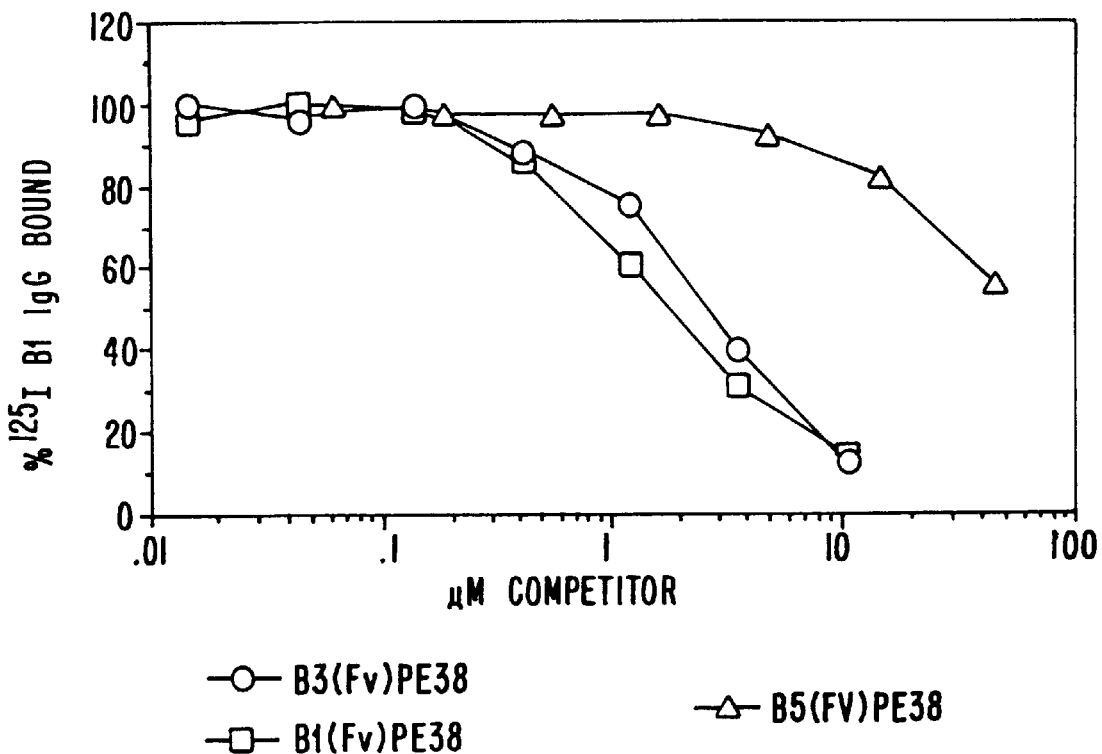

FIGS. 5a and 5b show antigen binding of B1(Fv)-PE38, B3(Fv)-PE38 and B5(Fv)-PE38. Antigen binding was estimated by competition of [$^{125}$I]-B1 IgG (FIG. 5a) or [$^{125}$I]-B3 IgG (FIG. 5b) binding to A431 cells at 4° C.

Figure 6A:
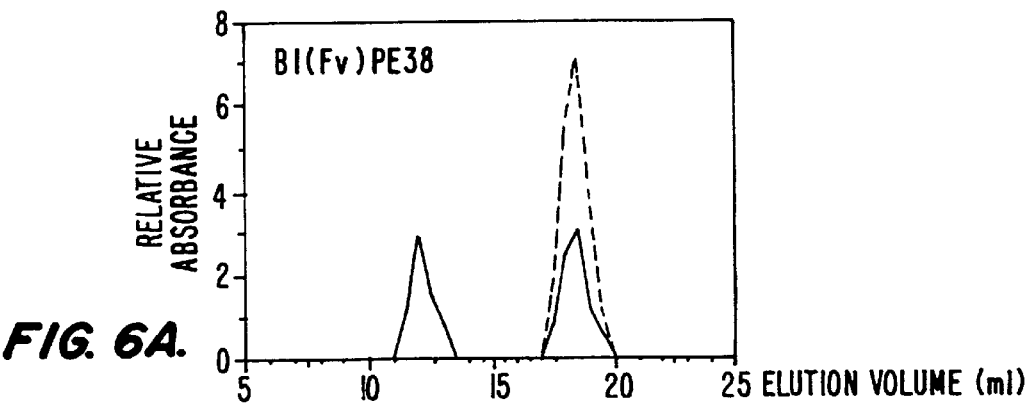
Figure 6B:
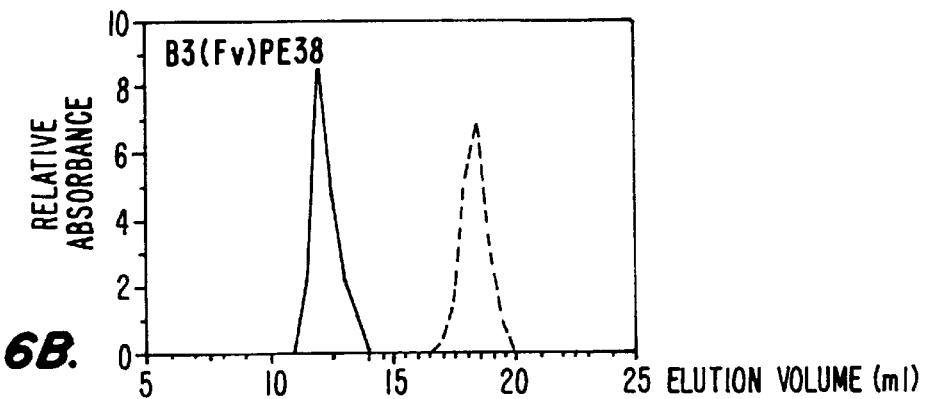
Figure 6C:
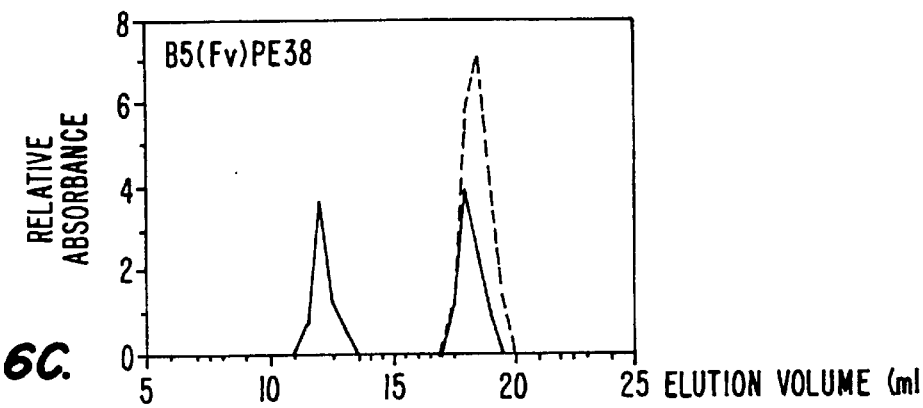
Figure 6D:
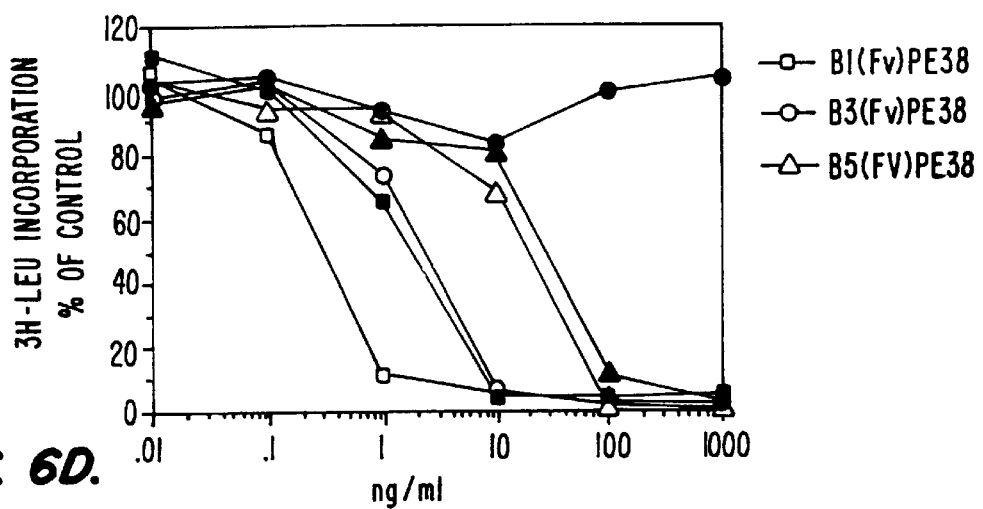

FIGS. 6a and 6b show stability data for B1(Fv)-PE38, B3(Fv)-PE38, and B5(Fv)-PE38. The immunotoxins were diluted in PBS to 0.1 mg/ml and incubated at 37° C. for 4 hours. (FIG. 6a) The molecular forms of the immunotoxins were than analyzed by size exclusion chromatography at 4° C. The monomer peak elutes at 18–20 ml, while the aggregates elute at 11–13 ml. Chromatograms of the proteins prior to incubation at 37° C. are shown by broken lines. The proteins after the incubation at 37° C. are shown by solid lines. (FIG. 6b) Cytotoxic activity of immunotoxins before (open symbols) or after (solid symbols) incubation at 37° C. Other details are as in FIG. 5b.

Figure 7:
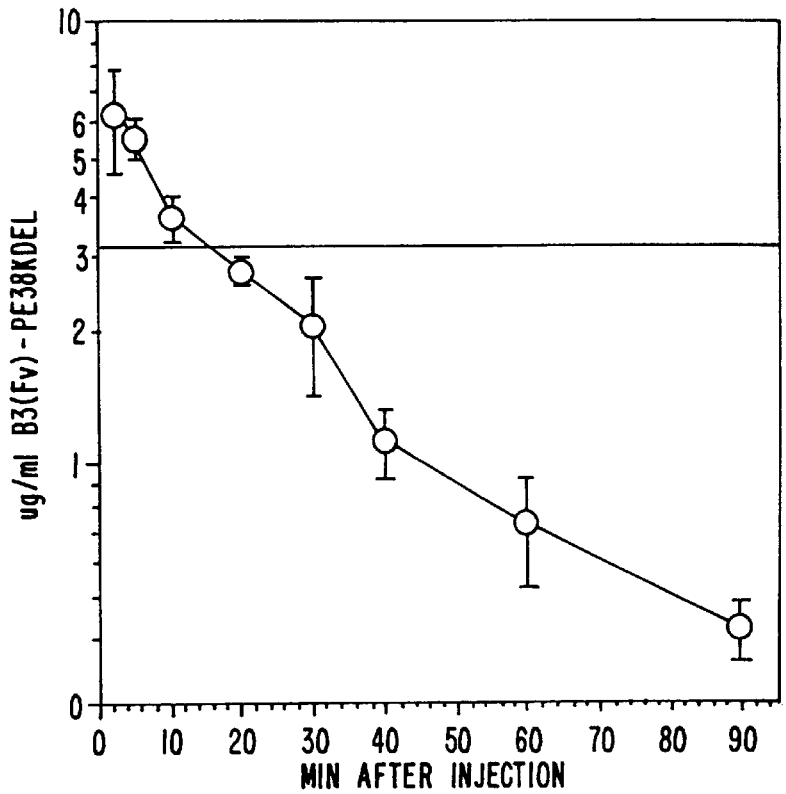
Figure 8A:
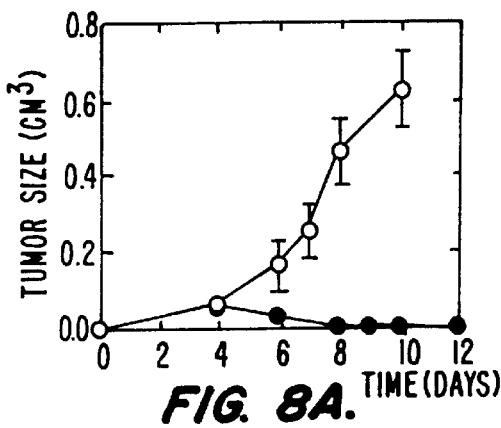
Figure 8B:
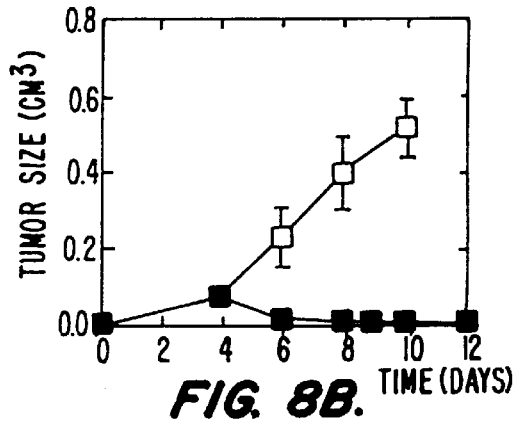
Figure 8C:
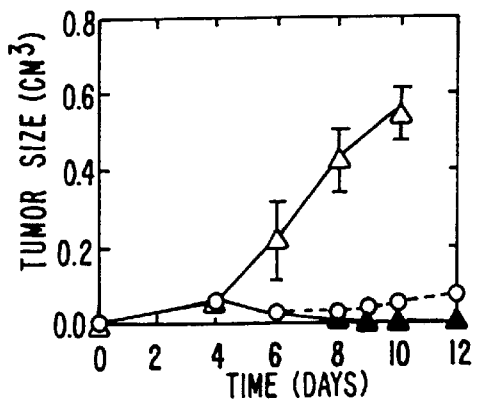
Figure 8D:
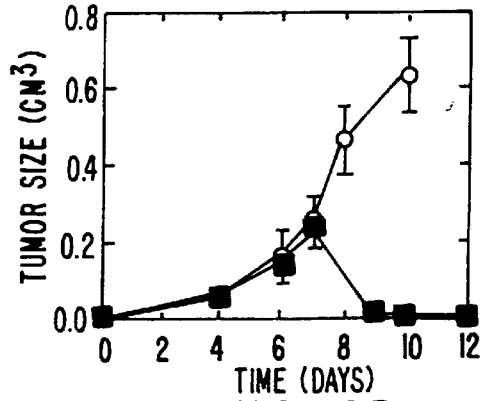

FIG. 7 shows blood levels of B3(Fv)-PE38KDEL in mice. Balb/c mice were injected intravenously with 10 μg of B3(Fv)-PE38KDEL and immunotoxin levels were measured at different time periods. Bars indicate the standard deviation.

FIG. 8 illustrates the effect of B3(Fv)-PE38KDEL on the growth of A431 tumors in nude mice. Mice were injected with 3×10$^6$ A431 cells on day 0 and treated beginning on day 4 with intravenous injections every 12 hrs ×6. A: (○) untreated; (●) 10 μg B3(Fv)-PE38KDEL;B: (○) 2.5 μg B3; (■) 5 μg B3(Fv)-PE38KDEL; C: (Δ) 2.5 μg anti-Tac (Fv) PE38KDEL; (▲) 2.5 μg B3(Fv)-PE38KDEL; (—○—) 0.5 μg B3(Fv)-PE38KDEL; D: treatment began on day 7 with intravenous injections every 12 hrs ×8. (○) untreated, (■) 5 μg B3(Fv)-PE38KDEL. Bars=1 standard deviation.

Figure 9:
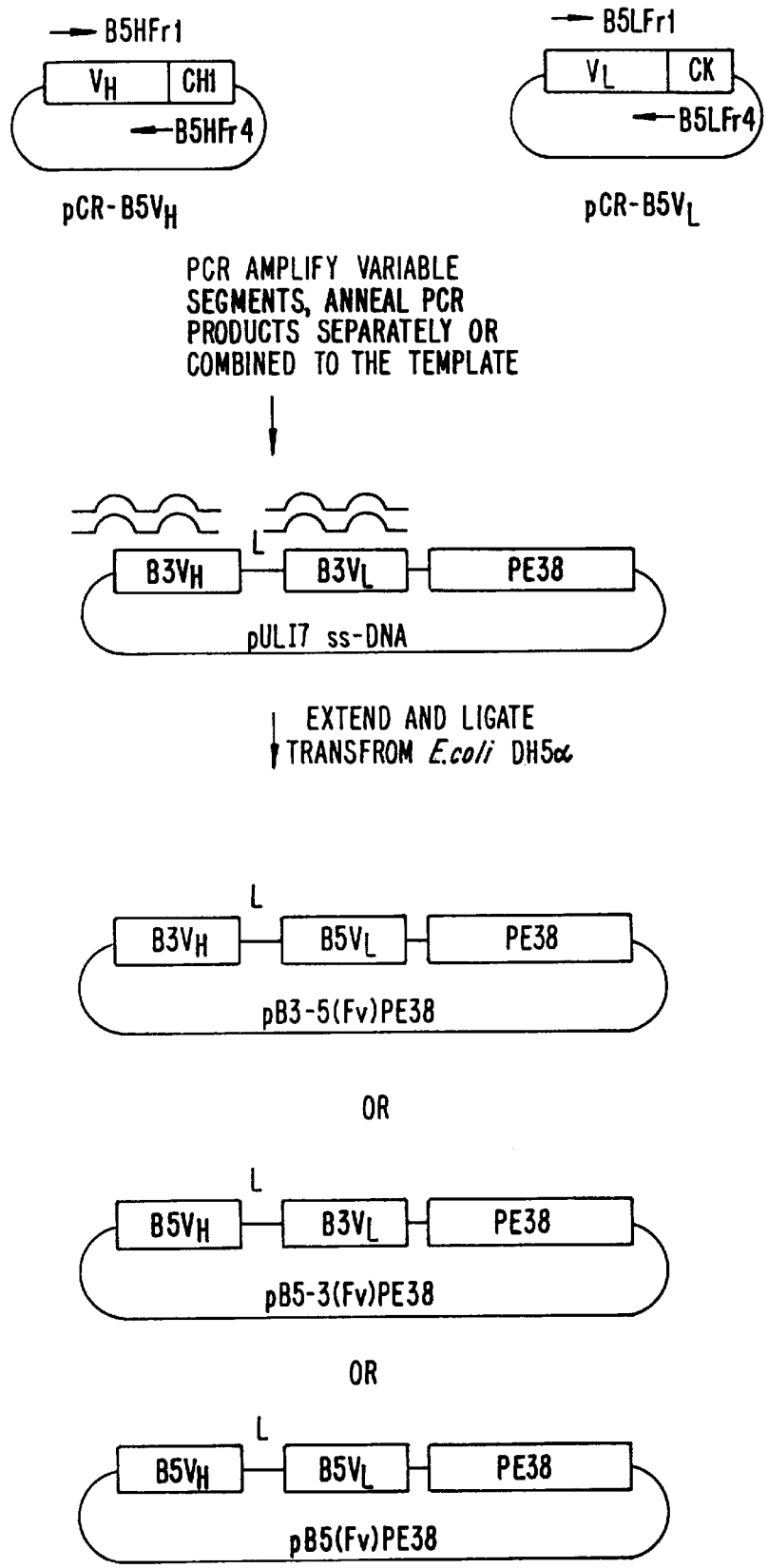

FIG. 9 illustrates the construction of plasmids for expression of B3-B5 chimeric Fv single chain immunotoxins. L indicates the (Gly$_4$Ser)$_3$ linker (SEQ ID No: 32) which connects the V$_H$ to the V$_L$ in the single-chain Fv configuration.

Figure 10A:
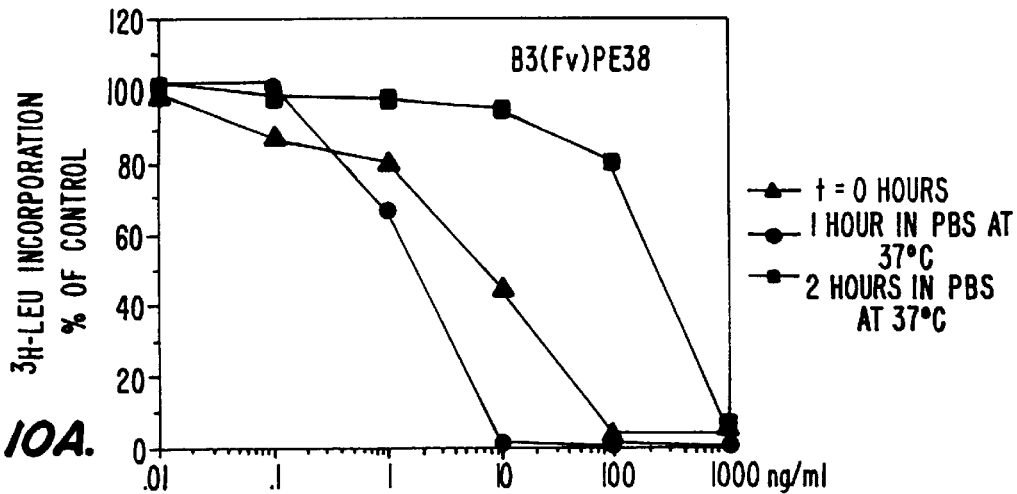
Figure 10B:
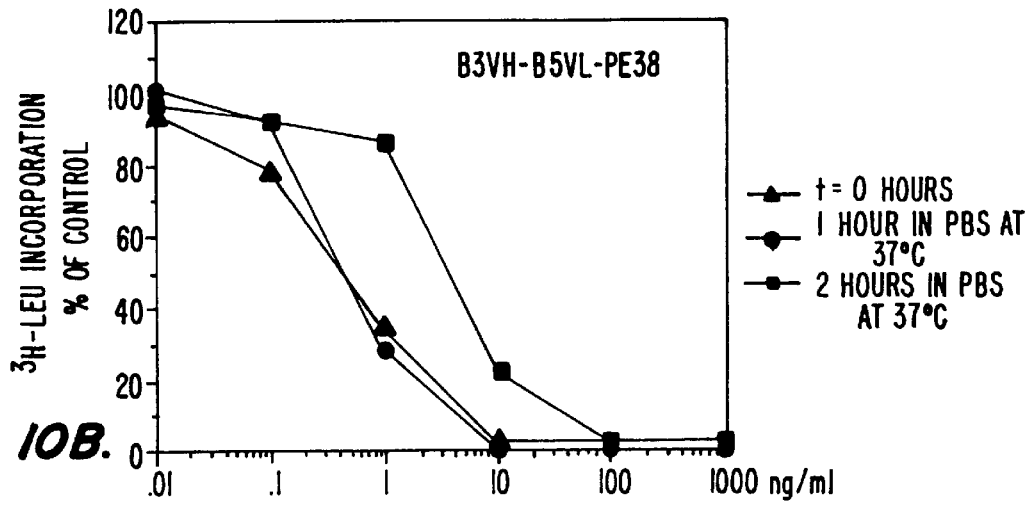
Figure 10C:
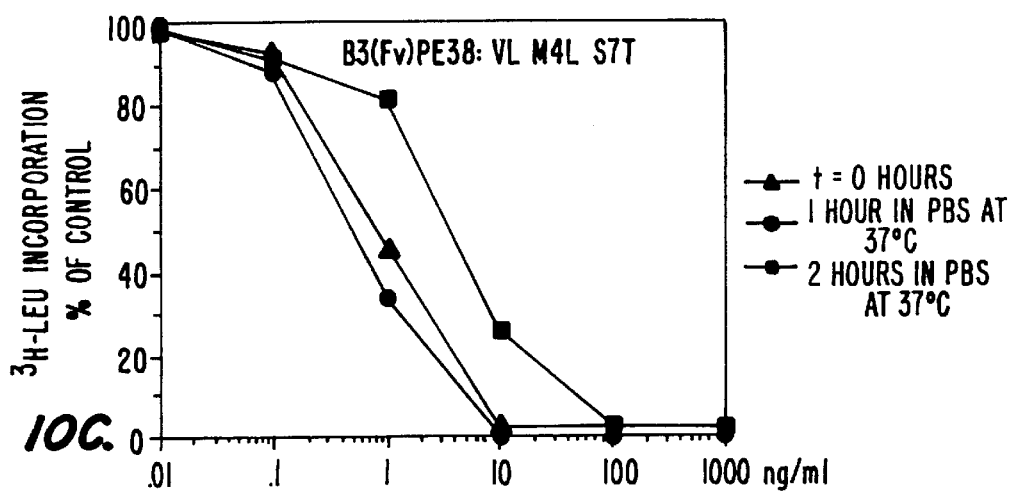

FIG. 10 shows the cytotoxic activity of immunotoxins B3(Fv)-PE38, B3V$_H$-B5V$_L$-PE38 and B3(Fv)-PE38: V$_L$ M4L S7T following incubation in PBS at 37° C. A431 epidermoid carcinoma cells were incubated with aliquots of the immunotoxins which were diluted in PBS+0.2% BSA following incubation at 37° C. $^3$H-Leucine was added 20 hours after addition of immunotoxins.

FIGS. 11a and 11b illustrate the humanization of B3(Fv). Alignment of the amino acid sequences of (A) B3 V$_H$, 56P1'CL V$_H$ and HUMB3V$_H$ (SEQ ID NOS: 45, 46 and 47, respectively) (B) B3 V$_L$, GM607 V$_L$, and HUMB$^3$V$_L$ (SEQ ID NOS. 48, 49 and 50 respectively). B3 amino acids that differ from the residues of the corresponding position of the human antibody are indicated by vertical lines above the sequence. Inter-domain residues that were not humanized are indicated by asterisks below the sequence. Heavy chain residue 82b is indicated. Numbers above the sequence indicate the positions of residues that were humanized.

Figure 12A:
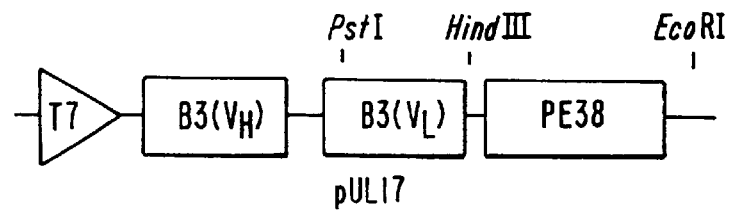
Figure 12B:
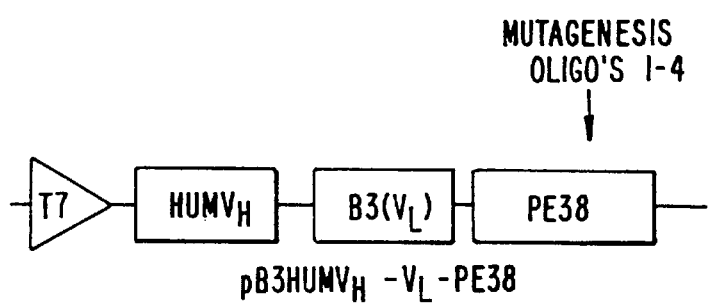

FIGS. 12a and 12b illustrate the plasmids utilized for expression of humanized B3(Fv)-PE38 immunotoxins. Single-stranded uracil-containing pULI7 DNA (A) encoding wild type B3(Fv)-PE38 was the template for the mutagenesis according to the method of Kunkel, Proc. Natl. Acad. Sci. USA 82,488–492 (1985). Single stranded uracil-containing pB3V$_H$-HUMV$_L$-PE$^{38}$ DNA (C) was the template for the generation of pHUMB3 (Fv)-PE38.

Figure 13A:
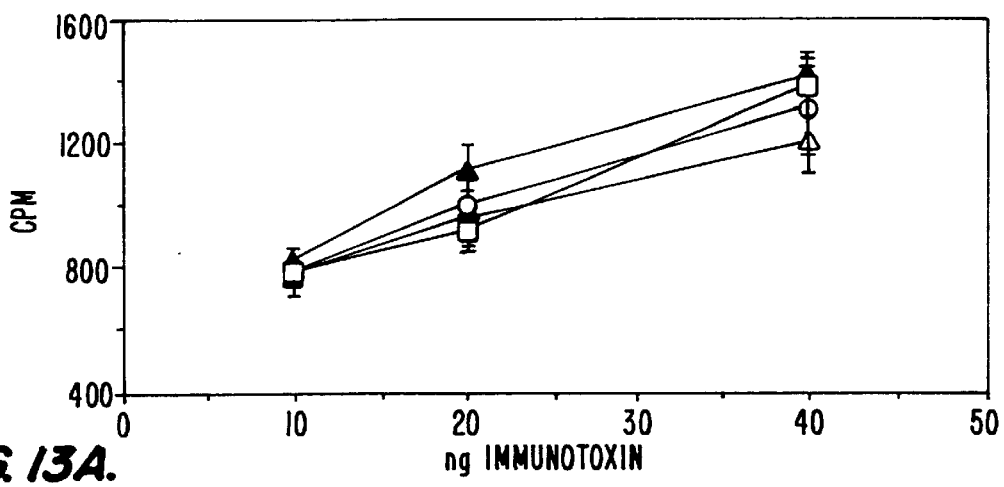
Figure 13B:
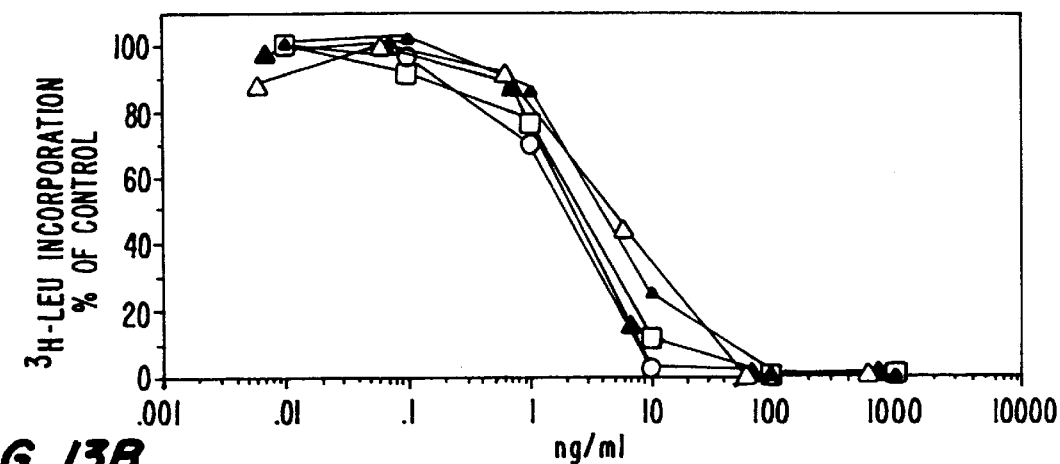
Figure 13C:
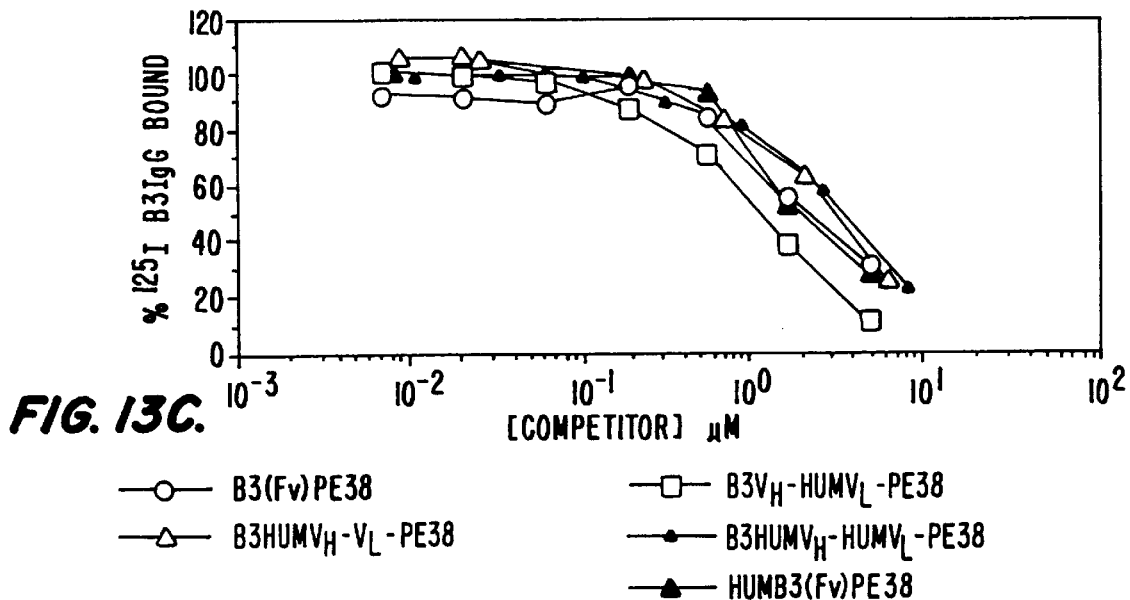

FIGS. 13a, 13b, and 13c show the ADP-ribosylation activity, cytotoxicity, and antigen binding of B3(Fv)PE38 and of the humanized variants. (A) ADP-ribosylation activity was determined by the incorporation on $^{14}$C-NAD into acid precipitable material using elongation factor 2 enriched wheat-germ extract. (B) Cytotoxicity towards A431 cells was measured by the inhibition of incorporation of [$^3$H]-leucine into cell protein. (C) Antigen binding was estimated by competition of [$^{125}$I]-B3 IgG binding to A431 cells at 4° C. with each immunotoxin.

Figure 14:
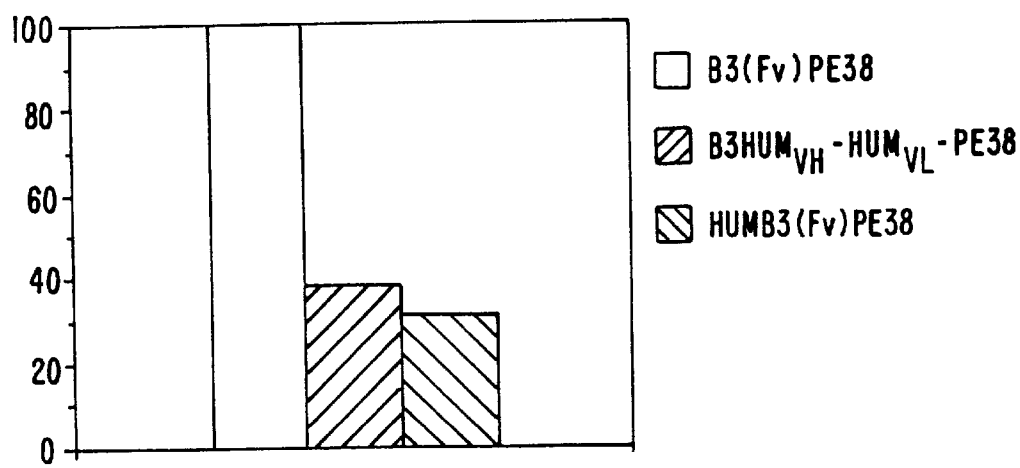

FIG. 14 shows the reactivity of pooled monkey anti-B3(Fv)-PE38 sera to B3(Fv)PE38 and humanized variants. B3(Fv)-PE38, B3HUMVH-HUMVL-PE38 and HUMPB3 (Fv)-PE38 were immobilized on a 96-well microtiter plate. Sera that were preincubated with PE38 as a competitor at a molar ratio of 1000 to 1 over the immobilized proteins were added in an equal volume at a dilution of 1:50. Percent reactivity was calculated by setting the mean reactivity with B3(Fv)-PE38 obtained from four independent experiments to 100% and adjusting the relative reactivities with the humanized variant accordingly.

FIGS. 15a and 15b provide the nucleotide (SEQ ID NO: 57 and SEQ ID NO: 58) and deduced amino acid sequences (SEQ ID NO: 61 and SEQ ID NO: 63) of B1 heavy (A) and light (B) chains. Underlined nucleotide sequences correspond (at the 5' end) or are complementary (at the 3' end) to the PCR primers which were used to PCR amplify the fragment. The amino acid sequence is in single-letter code; below is the amino acid sequence determined by Edman sequencing (SEQ ID NO: 62 and SEQ ID NO: 64) shown in italics. CDRs are underlined, and constant region amino acids are struck through.

FIGS. 16a and 16b provide the nucleotide (SEQ ID NO: 60) and deduced amino acid sequence (SEQ ID No: 65 and SEQ ID NO: 67) of B5 heavy chain (A) and the variable region and the beginning of the constant region of the light (B) chain. Other details are as in FIG. 15 (edman amino acid sequences are SEQ ID NO: 66 and SEQ ID NO: 68). The struck-through carboxyl-terminal amino acids in the heavy chain correspond to the beginning of the (Gly$_4$Ser)$_3$ linker (SEQ ID NO: 32) used to connect the V$_H$ and the V$_L$ in the single chain configuration.

FIG. 17 provides the amino acid (peptide) sequence of the B3 single chain Fv. The figure provides the sequences for the V$_H$ region (SEQ ID NO: 45), the linker and the V$_L$ (SEQ ID NO: 48) region respectively. CDRs are in parentheses.

FIG. 18 provides the nucleotide sequence of the humanized B3 single-chain Fv (SEQ ID NO: 31). CDRs are in parentheses.

DETAILED DESCRIPTION OF THE INVENTION

Definitions

Abbreviations used here for the twenty naturally occurring amino acids, the five naturally occurring nucleic acids and the eleven nucleic acid degeneracies (wobbles) follow conventional usage. In the polypeptide notation used herein, the left-hand direction is the amino terminal direction and the right-hand direction is the carboxy-terminal direction. In the nucleic acid notation used herein, the left-hand direction is the 5' direction and the right-hand direction is the 3' direction.

The term "nucleic acid" refers to a deoxyribonucleotide or ribonucleotide polymer in either single- or double-stranded form, and unless otherwise limited, would encompass known analogs of natural nucleotides that can function in a manner similar to naturally occurring nucleotides.

The phrase "nucleic acid encoding" or "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both full length nucleic acid sequences as well as shorter sequences derived from the full length sequences. It is understood that a particular nucleic acid sequence includes the degenerate codons of the native sequence or sequences which may be introduced to provide codon preference in a specific host cell. The nucleic acid includes both the sense and antisense strands as either individual single strands or in the duplex form.

The terms "isolated" or "substantially purified", when referring to recombinantly produced proteins, means a chemical composition which is essentially free of other cellular components. Such a composition is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The term "labeled antibody" as used herein refers to an antibody bound to a label such that detection of the presence of the label (e.g. as bound to a biological sample) indicates the presence of the antibody.

Cytotoxin refers to a molecule that when contacted with a cell brings about the death of that cell.

The phrase "binding specificity", "specifically binds to an antibody" or "specifically immunoreactive with," when referring to a protein or carbohydrate, refers to a binding reaction which is determinative of the presence of the protein or carbohydrate in the presence of a heterogeneous population of proteins and other biologics. Thus, under designated immunoassay conditions, the specified antibodies bind to a particular protein or carbohydrate and do not bind in a significant amount to other proteins or carbohydrates present in the sample. Specific binding to an antibody under such conditions may require an antibody that is selected for its specificity for a particular protein or carbohydrate. For example, antibodies raised to the $Le^Y$ antigens may be selected to provide antibodies that are specifically immunoreactive with $Le^Y$ proteins and not with other proteins. A variety of immunoassay formats may be used to select antibodies specifically immunoreactive with a particular protein or carbohydrate. For example, solid-phase ELISA immunoassays are routinely used to select antibodies specifically immunoreactive with a protein or carbohydrate. See Harlow and Lane (1988) *Antibodies, A Laboratory Manual*, Cold Spring Harbor Publications, N.Y., for a description of immunoassay formats and conditions that can be used to determine specific immunoreactivity.

The terms "recombinant DNA," "recombinant nucleic acid" or "recombinantly produced DNA" refer to DNA which has been isolated from its native or endogenous source and modified either chemically or enzymatically by adding, deleting or altering naturally-occurring flanking or internal nucleotides. Flanking nucleotides are those nucleotides which are either upstream or downstream from the described sequence or sub-sequence of nucleotides, while internal nucleotides are those nucleotides which occur within the described sequence or subsequence.

The terms "recombinant protein" or "recombinantly produced protein" refer to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein.

Mutations in proteins are designated by nomenclature consisting of the peptide sequence in which the mutation occurs, a representation of the non-mutated amino acid, followed by its position, followed by the representation of the mutated amino acid. Thus, for example, a mutation designated $B^3(Fv)V_L$ S7T is a mutation from serine (S) to threonine (T) at position 7 of the $V_L$ chain of B3(Fv).

Single Chain Antibodies

This invention relates to recombinantly produced single chain antibodies. In particular, this invention provides for recombinant single chain antibodies that may be joined to one or more effector molecules and, because of their ability to specifically bind to a particular preselected target molecule, these antibodies are useful as targeting moieties which serve to direct the joined effector molecules or compositions to a cell or tissue bearing the preselected target molecule.

As used herein, the term "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies may exist as intact immunoglobulins, or as modifications in a variety of forms including, for example, an Fv fragment containing only the light and heavy chain variable regions, a Fab or (Fab)'$_2$ fragment containing the variable regions and parts of the constant regions, a single-chain antibody (Bird et al., *Science* 242: 424–426 (1988); Huston et al., *Proc. Natl. Acad. Sci.* USA 85: 5879–5883

(1988) both incorporated by reference herein), and the like. The antibody may be of animal (especially mouse or rat) or human origin or may be chimeric (Morrison et al., *Proc Natl. Acad. Sci.* USA 81, 6851–6855 (1984) both incorporated by reference herein) or humanized (Jones et al., *Nature* 321, 522–525 (1986), and published UK patent application #8707252, both incorporated by reference herein). As used herein the term "antibody" includes these various forms. Using the guidelines provided herein and those methods well known to those skilled in the art which are described in the references cited above and in such publications as Harlow & Lane, *Antibodies: A Laboratory Manual,* Cold Spring Harbor Laboratory, (1988) the antibodies of the present invention can be readily made.

The term "Fv" region as used herein refers to a single chain antibody Fv region containing a variable heavy ($V_H$) and a variable light ($V_L$) chain. The heavy and light chain may be derived from the same antibody or different antibodies thereby producing a chimeric Fv region.

The term "effector molecule" or "effector composition" as used herein refer to agents having a particular biological activity which is to be directed to a particular target molecule or a cell bearing a target molecule. One of skill in the art will appreciate that effector molecules may include various drugs such as vinblastine, daunomycin and the like, cytotoxins such as native or modified Pseudomonas exotoxin or Diphtheria toxin, encapsulating agents (e.g., liposomes) which themselves contain pharmacological compositions, radioactive agents such as $^{125}I$, $^{131}Cs$, $^{32}P$, $^{14}C$, $^{3}H$, and $^{35}S$, target moieties and ligands.

As used herein "ligands" are molecules capable of reacting with or otherwise recognizing and specifically binding a "target" molecule. Ligands and their respective target molecules represent paired species. Typical paired species include, but are not limited to, enzyme/substrate, receptor/agonist, antibody/antigen, and lectin/carbohydrate. The binding between a ligand and its target may be mediated by covalent or non-covalent interactions or a combination of covalent and non-covalent interactions. When the interaction of the two species produces a non-covalently bound complex, the binding which occurs is typically electrostatic, hydrogen-bonding, or the result of hydrophilic/lipophilic interactions. Accordingly, "specific binding" occurs between a ligand and its target molecule where there is interaction between the two which produces a bound complex having the characteristics of an antibody/antigen or enzyme/substrate interaction. Specifically, examples of ligands include, but are not limited to antibodies, lymphokines, cytokines, receptor proteins such as CD4 and CD8, solubilized receptor proteins such as soluble CD4, hormones, growth factors, and the like which specifically bind desired target cells.

The choice of the particular effector molecule or composition depends on the particular target molecule or cell and the biological effect it is desired to evoke. Thus, for example, the effector molecule may be a cytotoxin where it is desired to bring about death of a particular target cell. Conversely, where it is merely desired to invoke a non-lethal biological response, the effector molecule may be a conjugated non-lethal pharmacological agent or a liposome containing a non-lethal pharmacological agent.

In a particularly preferred embodiment, the antibodies may be joined to an effector molecule that is a drug or to a cytotoxin to form an immunotoxin capable of selectively killing particular target cells. Numerous cytotoxic compounds are known to those of skill in the art and include, but are not limited to, ricin, abrin, Pseudomonas exotoxin (PE), Diphtheria toxin (DT), and the like. Preferred toxins are PE or DT. Native PE and DT are highly toxic compounds that typically bring about death through liver toxicity. PE and DT, however, can be modified into a form for use as an immunotoxin by removing the native targeting component of the toxin (e.g. domain Ia of PE and the B chain of DT) and replacing it with a different antibody targeting moiety.

The term "Pseudomonas exotoxin" (PE) as used herein refers to a full-length native (naturally occurring) PE or a PE that has been modified. Such modifications may include, but are not limited to, elimination of domain Ia, various amino acid deletions in domains II and III, single amino acid substitutions (e.g., replacing Lys with Gln at positions 590 and 606), and the addition of one or more sequences at the carboxyl terminus such (SEQ ID NO: 51) as KDEL and REDL (SEQ ID NO: 52). See Siegall et al., *J. Biol. Chem.* 264: 14256–14261 (1989). Thus, for example, PE38 refers to a truncated Pseudomonas exotoxin composed of amino acids 253–364 and 381–613 (see commonly assigned U.S. patent application Ser. No. 07/901,709 filed Jun. 18, 1992 incorporated herein by reference. The native C-terminus of PE, REDLK (SEQ ID NO: 53) (residues 609–613), may be replaced with the sequence KDEL (SEQ ID NO: 51), REDL (SEQ ID NO: 52), and Lys-590 and Lys-606 may be each mutated to Gln (see commonly assigned U.S. patent application Ser. No. 07/522,563 filed May 14, 1990, incorporated herein by reference).

The term "Diphtheria toxin" (DT) as used herein refers to full length native DT or to a DT that has been modified. Modifications typically include removal of the targeting domain in the B chain and, more specifically, involve truncations of the carboxyl region of the B chain.

The recombinant single chain antibodies of the present invention may be fused to, or otherwise bound to the effector molecule or composition by any method known and available to those in the art. The two components may be chemically bonded together by any of a variety of well-known chemical procedures. For example, the linkage may be by way of heterobifunctional cross-linkers, e.g. SPDP, carbodiimide, glutaraldehyde, or the like. Production of various immunotoxins is well-known within the art and can be found, for example in "Monoclonal Antibody-Toxin Conjugates: Aiming the Magic Bullet," Thorpe et al., *Monoclonal Antibodies in Clinical Medicine,* Academic Press, pp. 168–190 (1982) and Waldmann, *Science,* 252: 1657 (1991), both of which are incorporated by reference. To use the recombinant PE molecules with an antibody, a form of the PE molecule with cysteine at amino acid position 287 is preferred to couple the toxin to the antibody or other ligand through the thiol moiety of cysteine.

In a preferred embodiment, the antibodies of this invention may also be fused to a protein effector molecule by recombinant means such as through the use of recombinant DNA techniques to produce a nucleic acid which encodes both the antibody and the effector molecule and expressing the DNA sequence in a host cell such as *E. coli.* The DNA encoding the chimeric protein may be cloned in cDNA or in genomic form by any cloning procedure known to those skilled in the art. See for example Sambrook et al., *Molecular Cloning: A Laboratory Manual,* Cold Spring Harbor laboratory, (1989), which is herein incorporated by reference.

As indicated above, in addition to cytotoxins, the single chain antibodies of the present invention may be fused or chemically conjugated to a wide variety of effector molecules. Thus, for example, the antibody may be conjugated or fused to bacterial or plant toxins, or to other effector agents to treat or diagnose human cancer. For example, radionuclides conjugated to antibodies that bind to tumors can produce cell killing based on the high local concentration of radiation. Chemotherapeutic drugs, for example, vinblastine or daunomycin, can be coupled to the antibodies and delivered at high concentration to cells that react with the antibodies. Similarly, the antibodies of this invention may be utilized to specifically target a vehicle that encapsulates a therapeutic agent. For example, the antibodies may be conjugated to a liposome which itself carries a drug (e.g. doxorubicin) and thereby specifically targets the liposome to a specific tissue or cell. Alternatively, the antibodies may be recombinantly fused to a membrane-inserting protein and thereby incorporated into the liposome for delivery of therapeutic agents.

Fusion or conjugation of the antibodies of this invention to various labels produces a highly specific detectable marker that may be used to detect the presence or absence of cells or tissues bearing the particular molecule to which the antibody is detected. Alternatively, the antibodies may be chemically conjugated or fused to an effector molecule that is another specific binding moiety, e.g. a ligand such as those described above. In this form the composition will act as a highly specific bifunctional linker. This linker may act to bind and enhance the interaction between cells or cellular components to which the fusion protein binds. Thus, for example, where the fusion protein is a growth factor joined to an antibody or antibody fragment (e.g. an Fv fragment of an antibody), the antibody may specifically bind antigen positive cancer cells while the growth factor binds receptors (e.g., IL2 or IL4 receptors) on the surface of immune cells. The fusion protein may thus act to enhance and direct an immune response toward target cancer cells.

One of skill in the art will appreciate that the antibodies of the present invention may also be utilized as multiple targeting moieties. Thus this invention also provides for compositions in which two or more antibodies are bound to a single effector molecule. Where the effector molecule is a cytotoxin, the presence of two or more antibodies may increase specificity or avidity of binding of the immunotoxin. Conversely, multiple effector molecules may be fused or otherwise joined to a single antibody. Compositions of this nature may provide two or more kinds of biological activity with a single targeting moiety.

In a particularly preferred embodiment, the antibodies of this invention are antibodies that specifically bind Lewis$^Y$ (Le$^Y$) carbohydrates (Le$^Y$ carbohydrate antigens). As used herein, the Le$^Y$ carbohydrate antigens include natural or synthetic L$^Y$ carbohydrates or fragments thereof that contain epitopes recognizable by Le$^Y$ binding antibodies. Also included are carbohydrates, glycoproteins and other glycoconjugates which contain or mimic the Le$^Y$ carbohydrate or epitopes contained within the Le$^Y$ carbohydrate (see, Pastan et al., *Cancer Res.*, 51: 3781–3787 (1991) and Hoess et al., *Gene,* 128: 43–49 (1993)). Such mimics are known by their ability to specifically bind to known anti-Le$^Y$ antibodies such as B1, B3, B5, BR64 and BR96 (Hellstrom et al, *Cancer Res.,* 50:2183–90 (1990)), and the like.

Of the Le$^Y$ binding antibodies, particularly preferred are antibodies having the tissue binding specificity of B1, B3 or B5. The term "tissue binding specificity" as used herein refers to the particular distribution of tissues to which an antibody binds and does not bind as determined by immunohistochemical analysis. Methods of determining tissue binding specificity as well as the binding specificities for B1, B3 and B5 are described in U.S. Pat. No. 5,242,813 (see, especially Tables I, II and III) which is incorporated herein by reference.

The antibodies may be derived from the monoclonal antibodies designated B1, B3, and B5 (see U.S. Pat. No. 5,242,813). These antibodies have been shown to specifically bind to Lewis$^Y$ and Lewis$^Y$-related carbohydrate antigens that are typically found on various carcinomas including carcinomas of the breast, colon, cervix, and prostate.

The antibodies of this invention may be Fv regions comprising a variable light (V$_L$) and a variable heavy (V$_H$) chain. The light and heavy chains may be joined directly or through a linker. As used herein a Linker refers to a molecule that is covalently linked to the light and heavy chain and provides enough spacing and flexibility between the two chains such that they are able to achieve a conformation in which they are capable of specifically binding the epitope to which they are directed. Protein linkers are particularly preferred as they may be expressed as an intrinsic component of the fusion protein.

Preparation of Antibody Fv Fragments

Single chain B1, B3 and B5 Fv regions may be cloned from the hybridoma cell lines B1, B3 and B5 which were deposited on October 10, 1990 with the American Type Culture Collection (ATCC), 10801 University Boulevard, Manassas, Va. 20110-2209, where the deposits were granted the accession numbers ATCC HB 10572, HB 10573, and HB 10569, respectively. The deposits were made pursuant to the provisions of the Budapest Treaty.

The Fv regions may all be cloned using the same general strategy. Typically, for example, poly(A)$^+$ RNA extracted from the hybridoma cells is reverse transcribed using random hexamers as primers. The V$_H$ and V$_L$ domains are amplified separately by two polymerase chain reactions (PCR®). Heavy chain sequences may be amplified using 5' end primers which are designed according to the amino-terminal protein sequences of the B1, B3 and B5 heavy chains respectively (SEQ ID NOS: 19, 17, and 21 respectively) and 3' end primers according to consensus immunoglobulin constant region sequences (Kabat et al., *Sequences of Proteins of Immunological Interest.* 5th edition. U.S. Department of Health and Human Services, Public Health Service, National Institutes of Health, Bethesda, Md. (1991) incorporated by reference). Light chain Fv regions are amplified using 5' end primers designed according to the amino-terminal protein sequences of B1, B3 and B5 light chains respectively (SEQ ID NOS: 20, 18, and 22, respectively) and in combination with the primer C-kappa (Table 1 and SEQ ID NO: 14). Suitable primers are specifically illustrated in Examples 1 and 2 although one of skill in the art would recognize that other suitable primers may be derived from the sequence listings provided herein.

The crude PCR products are subcloned into a suitable cloning vector. Clones containing the correct size insert by DNA restriction are identified. The nucleotide sequence of the heavy or light chain coding regions may then be determined from double stranded plasmid DNA using sequencing primers adjacent to the cloning site. Commercially available kits (e.g. the Sequenase™ kit, United States Biochemical Corp., Cleveland, Ohio, USA) may be used to facilitate sequencing the DNA.

Of course the sequencing steps are unnecessary given the sequence information disclosed in the present invention. One of skill will appreciate that utilizing the sequence information provided for the Fv regions of B1, B3, and B5 (SEQ ID NOS: 17–22), nucleic acids encoding these sequences may be obtained using a number of methods well known to those of skill in the art. Thus, DNA encoding the Fv regions may be prepared by any suitable method, including, for example, amplification techniques such as ligase chain reaction (LCR) (see Wu and Wallace, *Genomics,* 4: 560 (1989), Landegren, et al, *Science,* 241: 1077 (1988) and Barringer, et al., *Gene,* 89: 117 (1990)), transcription amplification (see Kwoh, et al., *Proc. Natl. Acad. Sci. USA,* 86: 1173 (1989)), and self-sustained sequence replication (see Guatelli, et al., *Proc. Natl. Acad. Sci. USA,* 87: 1874 (1990)), cloning and restriction of appropriate sequences or direct chemical synthesis by methods such as the phosphotriester method of Narang et al. *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.,* 22: 1859–1862 (1981); and the solid support method of U.S. Pat. No. 4,458,066, all such references in this paragraph incorporated by reference herein.

Chemical synthesis produces a single stranded oligonucleotide. This may be converted into double stranded DNA by hybridization with a complementary sequence, or by polymerization with a DNA polymerase using the single strand as a template. While it is possible to chemically synthesize an entire single chain Fv region, it is preferable to synthesize a number of shorter sequences (about 100 to 150 bases) that are later ligated together.

Alternatively, subsequences may be cloned and the appropriate subsequences cleaved using appropriate restriction enzymes. The fragments may then be ligated to produce the desired DNA sequence.

Once the Fv variable light and heavy chain DNA is obtained, the sequences may be ligated together, either directly or through a DNA sequence encoding a peptide linker, using techniques well known to those of skill in the art. In a preferred embodiment, heavy and light chain regions are connected by a flexible peptide linker (e.g., (Gly$_4$Ser)$_3$(SEQ ID NO: 32)) which starts at the carboxyl end of the heavy chain Fv domain and ends at the amino terminus of the light chain Fv domain. The entire sequence encodes the Fv domain in the form of a single-chain antigen binding protein.

Preparation of Antibody Fusion Proteins

Once a DNA sequence has been identified that encodes an Fv region which, when expressed shows specific binding activity, fusion proteins comprising that Fv region may be prepared by methods known to one of skill in the art. The Fv region may be fused directly to the effector molecule (e.g. cytotoxin) or may be joined directly to the cytotoxin through a peptide connector. The peptide connector may be present simply to provide space between the targeting moiety and the effector molecule or to facilitate mobility between these regions to enable them to each attain their optimum conformation. The DNA sequence comprising the connector may also provide sequences (such as primer sites or restriction sites) to facilitate cloning or may preserve the reading frame between the sequence encoding the targeting moiety and the sequence encoding the effector molecule. The design of such connector peptides will be well known to those of skill in the art. However, one particularly preferred connector is the peptide SGGPEGGS (SEQ ID NO: 44), designated herein as the C3 connector.

Methods of producing fusion proteins are well known to those of skill in the art. Thus, for example, Chaudhary et al., *Nature,* 339: 394–97 (1989); Batra et al., *J. Biol. Chem.* 265: 15198–15202 (1990); Batra et al., *Proc. Natl. Acad. Sci. USA,* 86: 8545–8549 (1989); Chaudhary et al., *Proc. Natl. Acad. Sci. USA,* 87: 1066–1070 (1990), all incorporated by reference, describe the preparation of various single chain antibody-toxin fusion proteins.

Generally producing immunotoxin fusion proteins involves separately preparing the Fv light and heavy chains and DNA encoding any other protein to which they will be fused and recombining the DNA sequences in a plasmid or other vector to form a construct encoding the particular desired fusion protein. However, a simpler approach involves inserting the DNA encoding the particular Fv region into a construct already encoding the desired second protein.

Thus, for example, DNA encoding B1(Fv), B3(Fv), B5(Fv) or chimeric Fv fusion proteins is most easily prepared by inserting the DNA encoding the B1, B3, B5 or chimeric Fv regions into constructs already containing DNA encoding the desired cytotoxin. The expression plasmid pVC38H contains the gene from the immunotoxin TGFα-PE40 under control of the T7 promoter, the Tφ transcription terminator at the 3' end of the PE40 coding region and the single strand replication region F$^+$, to generate single stranded phage DNA by contransfection with (M13) helper phages, if desired to create derivatives of the plasmid by site directed mutagenesis (Chaudhary et al. *Proc.*

*Natl. Acad. Sci.USA,* 87: 1066–1070 (1990). Similarly, the plasmid pRK79K encodes the Pseudomonas exotoxin PE38KDEL (Chaudhary, et al. *Proc. Natl. Acad. Sci. USA,* 87: 308–312 (1990).

The DNA sequence encoding the Fv region is inserted into the construct using techniques well known to those of skill in the art. Thus, for example, to create a plasmid for expression of the immunotoxin B3(Fv)-PE40 (pULEE3), the TGFα gene is removed and replaced by the B3(Fv) gene in a 3 fragment ligation, using an NdeI/BamHI fragment of the heavy chain coding region and the BamHI/HindIII fragment encoding the light chain Fv (FIG. 1a) as described in Example 1.

Similarly, a plasmid encoding B3(Fv)-PE38 may be produced by removing the PE40 coding region from pULI1 from the HindIII site to an EcoRI site positioned just beyond the PE40 gene and replacing it with a HindIII/EcoRI fragment from pRK79K described by Chaudhary et al. supra. This approach is described in greater detail in Example 1.

A particularly preferred approach involves the use of plasmid pULI7 which encodes the B3(Fv)-PE38 immunotoxin (Benhar et al. *Bioconjug. Chem.,* 5: 321–326 (1994)). For each Fv, the V$_H$ and V$_L$ sequences are PCR amplified using the heavy chain and light chain in their respective plasmids as templates. The amplification primers are designed to have at their ends sequences that are complementary to the translation initiation, peptide linker and Fv-toxin junction (connector) which are common to the single-chain Fv-immunotoxin expression vectors. The PCR products are purified and annealed to a uracil-contaning single stranded DNA corresponding to the pULI7 DNA prepared by rescue of pULI17 with a helper phage. The annealed PCR products are extended using the single stranded DNA as a template (see, for example, MUTAGENE® mutagenesis protocol, Biorad, Hercules, Calif., USA). The intact DNA may be used to transform cells and express the new fusion protein. In a preferred embodiment, because annealing efficiency to the template is low, the remaining intact "unmodified" DNA may be digested using a restriction endonuclease which has a unique site in the B3(Fv) template but that is absent from B1 and B5. This destroys any residual B3(Fv) sequences leaving only the modified sequences. This approach is described in greater detail in Example 2.

The Preparation of DNA Encoding Variable Domain Shuffled Fusion Proteins

It was observed that the stability of monoclonal antibody B3 could be improved. In the form of a single chain Fv immunotoxin, B3 is considerably more stable, however it still undergoes inactivation, mainly by aggregation, especially upon incubation in 0.15M NaCl, 0.01M NaPO$_4$ pH 7.4 at 37° C. In contrast to B3(Fv)-PE38 immunotoxin, B5(Fv)-PE38 is more resistant to inactivation under these conditions (see FIG. 6a). Based on these observations, the stability of chimeric Fv immunotoxins was examined.

It is an unexpected discovery of the present invention that chimeric Fv regions containing variable heavy and light chain domains from different, albeit related, antibodies may show significantly greater stability in vitro and in vivo than Fv regions where both the heavy and light domain are derived from the same antibody. Thus, for example, a fusion protein comprising a B3 variable heavy region and a B5 variable light region fused together and to PE38 shows higher activity and longer term stability than a B3(Fv)-PE38 fusion protein.

Nucleic acids encoding chimeric Fv regions are easily prepared using the techniques described above. The $V_H$ and $V_L$ sequences are PCR amplified using the heavy chain and light chain in their respective plasmids as templates as described. However, instead of using the $V_H$ and $V_L$ DNA from the same antibody, the $V_H$ and $V_L$ DNAs are selected from different antibodies. Thus, for example, one may combine a B3$V_H$ with a B5$V_L$ or a B5$V_H$ with a B3$V_L$ and so forth. The DNAs are annealed to a uracil-containing single stranded DNA corresponding to the pULI7 DNA and the synthesis of the chimeric Fv-cytotoxin fusion protein DNA is completed as described above and in Examples 2 and 12.

One of skill will appreciate that it is possible to eliminate the cytotoxin moiety and express the chimeric or single antibody Fv regions alone. These may be used in various chemical conjugates for example, either directly with toxins or other therapeutic agents, with carriers for therapeutic agents such as liposomes, or with various labels and markers such as fluorescent labels.

Stabilizig Mutations of B3

When a more stable related form of an antibody is identified, site directed mutagenesis may be used to identify the differences between the more and less stable forms. Thus, for example the B$^3V_H$-BS$V_L$-PE3$^8$ immunotoxin shows greater stability than the B3-PE38 (B$^3V_H$-B$^3V_L$-PE3$^8$) immunotoxin. To identify the amino acid residues contributing to the increased stability one performs a sequence analysis to identify those regions of the particular light or heavy region (in this case the $V_L$ region) that differ from the corresponding light or heavy chain in the non-chimeric antibody. Once the differences have been identified, mutations reflecting those differences may be systematically introduced into the corresponding region of the non-chimeric antibody. Comparison of the activity and stability of the mutated antibody with the chimeric antibody fusion protein will indicate which mutation is responsible for the increased stability. For example, it was discovered that replacing the B3 $V_L$ methionine 4 with leucine stabilized the immunotoxin as much as the B3$V_H$-B5$V_L$-PE38 combination whereas replacing $V_L$ serine 7 with threonine had no stabilizing effect. Thus, in a particularly preferred embodiment, the fusion protein comprises either B$^3V_H$-B5$V_L$-PE38 or B3(Fv)-PE38: $V_L$ M4T.

Mutations that Increase Antibody Binding Affinity

An unexpected result of the present invention is the discovery that mutations at position 95 of the $V_H$ region can alter the binding affinity of the single chain antibody. More specifically, it was discovered that mutations that altered the serine at position 95 in B3(Fv) to tyrosine or to phenylalanine, which are the most common amino acids at this position in other antibodies, reduced the binding affinity of B3(Fv) by approximately 10-fold (see Example 18). Conversely, when the tyrosine at $V_H$ 95 in B5(fv) was mutated to serine showed a for-fold increase binding activity as analyzed by cytotoxicity assays. B5(Fv) differed from B3(Fv) in having a completely different binding site. Thus the effect of the mutation is independent of the particular binding site.

Without being bound to a particular theory, it is believed that a serine located in the $V_H/V_L$ interface slightly destabilizes the interface contacts enabling movement of $V_H$ relative to $V_L$. This movement facilitates a so called "induced fit" binding mode. This destabilization mechanism would be expected to function in any antibody in which the $V_H$ 95 position is not normally a serine. Thus, this invention provides a new mechanism for increasing the binding affinity of antibodies that do not normally have a serine at $V_H$ position 95.

Humanized B3(Fv)

Because monoclonal antibodies B1, B3 and B5 are mouse antibodies, repeated administration of either labeled antibodies or the immunotoxins including these antibodies as targeting moieties will result in the formation of anti-mouse antibodies (Parren et al., *Hum. Antibod. Hybridomas.*, 3: 137–145 (1992)), in addition to the production of antibodies to the toxin moiety. This immune response may preclude long term treatment in some cases. Therefore it is desirable to produce less immunogenic molecules.

As a first step in making less immunogenic molecules the Fv portion of the mouse antibody is humanized so that it may then be used to replace the Fv portion of the murine antibody in the fusion proteins of the present invention. Humanized antibodies are non-human antibodies in which some or all of the amino acid residues are replaced with the corresponding amino acid residue found in a similar human antibody. Humanization thereby reduces the antigenic potential of the antibody.

Antibody variable domains have been humanized by various methods, such as CDR grafting (Riechmann et al., *Nature*, 332: 323–327 (1988)), replacement of exposed residues (Padlan, *Mol. Immunol.* 28: 489–498 (1991)) and variable domain resurfacing (Roguska et al., *Proc. Natl. Acad. Sci. USA*, 91: 969–973 (1994), all incorporated by reference. The minimalistic approach of resurfacing is particularly suitable for antibody variable domains which require preservation of some mouse framework residues to maintain maximal antigen binding affinity. However, the straightforward CDR grafting approach has also been successfully used for the humanization of several antibodies either without preserving any of the mouse framework residues (Jones et al. *Nature*, 321: 522–525 (1986) and Verhoeyen et al., *Science*, 239: 1534–1536 (1988)) or with the preservation of just one or two mouse residues (Riechmann et al., *Nature*, 332: 323–327 (1988); Queen et al., *Proc. Natl. Acad. Sci. USA*, 86: 10029–10033 (1989), all incorporated by reference.

To improve the B1, B3, or B5 antibodies or the chimeric antibodies of this invention, for therapeutic applications, the Fv portion is humanized by a method referred to as "framework exchange". In this approach, framework residues are identified that differ from human framework residues in highly homologous human $V_H$ or $V_L$ donors. These differing framework residues are then simultaneously mutated to human residues. The mutations are introduced onto a single-stranded DNA template prepared from a single-chain immunotoxin cassette which may be expressed in *E. coli* and allows the rapid purification and analysis of the resulting humanized variants.

This approach combines, yet deviates from the principles of CDR grafting or from the replacement of exposed residues, as some residues that are not normally exposed are humanized, while some other residues that are normally exposed are not humanized. Decisions to preserve certain mouse residues are based on knowledge regarding the effect of mutating these particular residues on the binding affinity of the Fv fragment, or on the possible interactions of these residues with other Fv residues observed in a structural model.

More specifically, humanization is accomplished by aligning the variable domains of the heavy and light chains with the best human homolog identified in sequence databases such as GENBANK or SWISS-PROT using the standard sequence comparison software as described above. Sequence analysis and comparison to a structural model based on the crystal structure of the variable domains of monoclonal antibody McPC603 (Queen et al., *Proc. Natl. Acad. Sci.* USA, 86: 10029–10033 (1989) and Satow et al., *J. Mol. Biol.* 190: 593–604 (1986)); Protein Data bank Entry IMCP) allows identification of the framework residues that differ between the mouse antibody and its human counterpart.

In a preferred embodiment, the mouse residues at B3 $V_H$ positions 1, 3, 19 24, 89 and 91 (see coordinates in Kabat et al. supra.) and B3 $V_L$ positions 2, 3 and 41 (FIGS. 11a and 11b) are preserved. In a particularly preferred embodiment, residue 82b in B3 $V_H$ is mutated to arginine.

$V_H$ and $V_L$ gene segments (e.g. in plasmid pULI7) encoding wild type B3(Fv)-PE38 may be independently humanized by site specific mutagenesis (see Example 14). One of skill in the art will appreciate that once the Fv region has been cloned and sequenced, alteration of various residues by site specific mutagenesis is routine using standard techniques well known to those of skill in the art (Kunkel, *Proc. Natl. Acad. Sci.* USA, 82: 488–492 (1985)).

Expression of Recombinant Proteins

The recombinant Fv regions and fusion proteins incorporating these antibody regions may be expressed in a variety of host cells, including *E. coli,* other bacterial hosts, yeast, and various higher eukaryotic cells such as the COS, CHO and HeLa cells lines and myeloma cell lines. A particularly preferred host is *E. coli.* The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes, *Protein Purification,* Springer-Verlag, N.Y. (1982), Deutscher, *Methods in Enzymology* Vol. 182: *Guide to Protein Purification.,* Academic Press, Inc. N.Y. (1990)). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the single chain Fv region or a fusion protein comprising a single chain Fv region may possess a conformation substantially different than the native protein. In this case, it may be necessary to denature and reduce the protein and then to cause the protein to re-fold into the preferred conformation. Methods of reducing and denaturing the protein and inducing re-folding are well known to those of skill in the art. (See, Debinski et al. *J. Biol. Chem.,* 268: 14065–14070 (1993); Kreitman and Pastan, *Bioconjug. Chem.,* 4: 581–585 (1993); and Buchner, et al., *Anal. Biochem.,* 205: 263–270 (1992) which are incorporated herein by reference.) Debinski et al., for example, describe the denaturation and reduction of inclusion body proteins in guanidine-DTE. The protein is then refolded in a redox buffer containing oxidized glutathione and L-arginine.

One of skill would recognize that modifications can be made to the single chain Fv region and fusion proteins comprising the single chain Fv region without diminishing their biological activity. Some modifications may be made to facilitate the cloning, expression, or incorporation of the single chain Fv region into a fusion protein. Such modifications are well known to those of skill in the art and include, for example, a methionine added at the amino terminus to provide an initiation site, or additional amino acids placed on either terminus to create conveniently located restriction sites or termination codons. For example, in a preferred embodiment, the primers used to construct B5(Fv) will introduce a sequence encoding an initiator methionine for expression in *E. coli* and an NdeI restriction site to facilitate cloning.

One of skill will recognize that other modifications may be made. Thus, for example, amino acid substitutions may be made that increase specificity or binding affinity of single chain Fv region and fusion proteins comprising the single chain Fv region, etc. Alternatively, non-essential regions of the molecule may be shortened or eliminated entirely. Thus, where there are regions of the molecule that are not themselves involved in the activity of the molecule, they may be eliminated or replaced with shorter segments that serve to maintain the correct spatial relationships between the active components of the molecule. Alternatively more flexible segments may be placed in interdomain regions which then can facilitate folding or production of the molecule (Brinkmann, et al. *Proc. Natl. Acad. Sci.* USA, 89: 3075–3079 (1992).

Diagnostic Assays

In addition to the targeting of immunotoxins to tumors in a cancer patient, the recombinant antibodies of the present invention also recognize materials such as surface mucins on tumor cells that would be expected to be shed into the surrounding tissues, picked up by the blood stream, and detectable in blood samples taken from distant sites. Such shed antigens have proven to be useful in the diagnosis of primary and recurrent cancers using antibodies that react to these shed antigens. A currently useful example of this is the CA125 antigen that can be assayed in sera from patients with ovarian cancer to predict recurrence or to confirm a primary diagnosis of tumor. Similarly, B1, B3 and B5 may be useful in the diagnosis of tumors.

Also, the selective reactivity of these antibodies with certain types of tumor cells may be exploited for anatomic pathological diagnosis of tumors, clarifying the type and origin of tumors, and whether a particular group of cells represents a recurrence of a previous tumor or the development of another primary tumor elsewhere. Such a diagnostic determination can be useful for the subsequent planning of anti-tumor therapy in each particular patient. In particular, immunohistochemical pathologic diagnosis in tissue sections (e.g., biopsies) or cytological preparations (e.g., Pap smears, effusions) can be performed using the monoclonal antibodies of the present invention.

Another potential use of such targeting antibodies could be in the diagnosis of macroscopic foci of a tumor using antibodies B1, B3 or B5 coupled to radioisotopes that could be detected either by external body scanning (imaging diagnosis) or by localization using radiation detector probes at the time of exploratory surgery.

In general, the diagnostic methods described above involve contacting a B1(Fv), B3(Fv), B5(Fv) or chimeric Fv region with a biological sample either in vivo or ex vivo and subsequently detecting the binding of that antibody to the target tissue. In a preferred embodiment a diagnostic method comprises the steps of (a) removing a tissue or fluid sample from a patient; (b) adding an antibody which includes the Fv region of a heavy chain of a first antibody and the Fv region of a light chain of a second antibody, where the Fv regions are recombinantly fused to form a single molecule that specifically bind a $Lewis^Y$-related carbohydrate antigen; and (c) detecting for the presence or absence of the antibody in the sample.

In a preferred embodiment, detection is by the detection of a label bound to the antibody. Means of labeling antibodies are well known to those of skill in the art. Labels may be directly linked through a covalent bond or covalently through a linking molecule which typically bears reactive sites capable of forming covalent bonds with the label and the antibody respectively. A common approach is to label the antibody and the label with either avidin or streptavidin or biotin which, in turn, bind irreversibly with each other.

Suitable labels are well known to those of skill in the art. The term "label", as used herein, refers to a composition detectable by spectroscopic, photochemical, biochemical, immunochemical, or chemical means. For example, useful labels include radioactive molecules such as $^{32}P$, $^{14}C$, $^{125}I$, $^{3}H$, and $^{35}S$, fluorescent dyes such as fluorescein or rhodamine, electron-dense reagents, enzymes (as commonly used in an ELISA), luminescent enzymes such as luciferase and the like.

Pharmaceutical Compositions

The recombinant fusion proteins and pharmaceutical compositions of this invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the fusion proteins and pharmaceutical compositions of this invention, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The recombinant fusion proteins and pharmaceutical compositions of this invention are particularly useful for parenteral administration, such as intravenous administration or administration into a body cavity or lumen of an organ. The compositions for administration will commonly comprise a solution of the single chain antibody or a fusion protein comprising the single chain antibody dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of single chain antibody, fusion protein, or labeled single chain antibody in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.01 to 100 mg per patient per day. Dosages from 0.1 up to about 1000 mg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The compositions containing the present fusion proteins or a cocktail thereof (i.e., with other proteins) can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

Among various uses of the cytotoxic fusion proteins of the present invention are included a variety of disease conditions caused by specific human cells that may be eliminated by the toxic action of the protein. One preferred application is the treatment of cancers, in particular cancers in which the tumor cells express carbohydrate antigens that are members of the $Lewis^Y$ family. Such cancers include, but are not limited to colon, breast, esophagus, bladder, gastric, head and neck, lung and ovarian carcinomas. The fusion proteins may also be used in vitro, for example, in the elimination of harmful cells from bone marrow before transplant where those cells express $Lewis^Y$-related antigens.

Kits

This invention also embraces kits for research or diagnostic purposes. Research kits typically include one or more containers containing the single chain antibodies of the present invention. In a preferred embodiment, research kits comprise containers containing single chain B1(Fv), B3(Fv), B5(Fv), chimeric Fv, mutated Fv or humanized Fv antibodies in a form suitable for derivatizing with a second molecule, e.g. a label, a drug, a cytotoxin, and the like. In another embodiment, the research kits may contain DNA sequences encoding these antibodies. Preferably the DNA sequences encoding these antibodies are provided in a plasmid suitable for transfection into and expression by a host cell. The plasmid may contain a promoter (often an inducible promoter) to regulate expression of the DNA in the host cell. The plasmid may also contain appropriate restriction sites to facilitate the insertion of other DNA sequences into the plasmid to produce various fusion proteins. The plasmids may also contain numerous other elements to facilitate cloning and expression of the encoded proteins. Such elements are well known to those of skill in the art and include, for example, selectable markers, initiation codons, termination codons, and the like.

Diagnostic kits typically comprise containers containing the antibodies described above. The antibodies are themselves derivatized with a label or, alternatively, they may be bound with a secondary label to provide subsequent detection. As described above, such labels may include radiolabels, fluorescent labels, enzymatic labels, i.e., horseradish peroxidase (HRP), or the like. The kit may also contain appropriate secondary labels (e.g. a sheep anti-mouse-HRP, or the like). The kit may also contain various reagents to facilitate the binding of the antibodies, the removal of non-specific binding antibodies, and the detection of the bound labels. Such reagents are well known to those of skill in the art.

Methods for using the research and diagnostic kits described above are generally well known, and will generally be provided in an instruction manual for use of the kit.

EXAMPLES

The following examples are offered by way of illustration, not by way of limitation.

Example 1

Cloning of DNA Fragments Encoding the Heavy and Light Fv Region of MAb B3

B3 cloning experiments and propagation of plasmids were carried out initially in *E. coli* HB101 (Boyer et al., *J. Molec. Biol.* 41: 459–72 (1969)). DNA fragments encoding the Fv portions of the heavy and light chain of monoclonal antibody (MAb) B3 were obtained by (PCR®) amplification of single stranded DNA which was synthesized by random primed reverse transcription of mRNA from a B3 monoclonal antibody producing hybridoma cell line. Polymerase chain reaction (Saiki et al, *Science,* 239: 487–91 (1988)) was performed using the Perkin Elmer GeneAmp kit and an Perkin Elmer/Cetus thermocycler, under conditions as described in Chaudhary et al., *Proc. Natl. Acad. Sci. USA* 87: 1066–70 (1990).

Figure 1A:
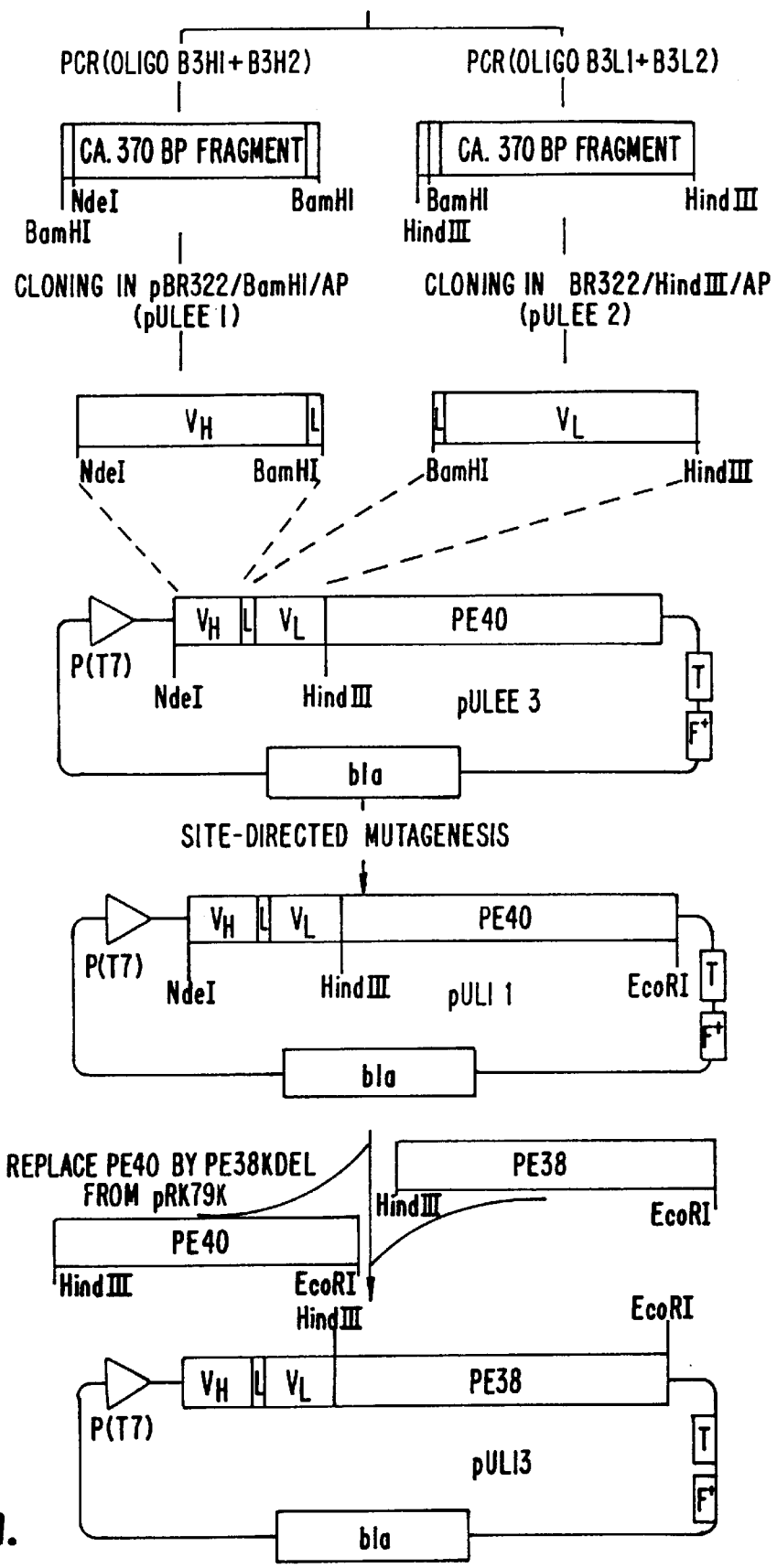
FIG. 1a illustrates the strategy for the cloning of the heavy and light chain Fv genes of monoclonal antibody B3 and the construction of expression vectors (e.g., plasmids) for the expression of B3(Fv) immunotoxins. The cloning strategy is a variation of that previously described (Chaudhary et al., Proc. Natl. Acad. Sci. USA, 87: 1066–70 (1990)). The plasmid pVC38H, which is used as a vector for construction of immunotoxins from heavy and light chain Fv regions, contains an NdeI and a HindIII recognition sequence preceding the PE40 gene (Chaudhary et al., supra (1990)). (*) indicates a PCR-generated mutation and was repaired by site directed mutagenesis; (L) indicates the region encoding the (Gly$_4$Ser)$_3$ linker (SEQ ID No: 32) which serves to join heavy and light chains of the immunotoxin.

The primer pair B3-H1 and B3-H2 was used for amplification of the heavy chain Fv coding region, while the primer pair B3-L1 and B3-L2 was used for amplification of the light chain Fv coding region (see Table 1 and SEQ ID NOS: 1, 2, 8 and 9, respectively). These oligonucleotides have at their 3' ends constant sequences that occur at the beginning and end of mouse Fv DNA. At their 5' ends are restriction endonuclease recognition sites (NdeI, BamI, HindIII) for cloning of the PCR products as shown in FIG. 1*a*. The products of the amplifications of heavy- and light chain Fv DNA fragments were identified by agarose gel electrophoresis to be DNA fragments between 350 and 400 bp. They were purified from gels, cut with BamHI or HindIII (FIG. 1*a*) and, after purification on a second gel, ligated with HindIII- or BamHI linearized and dephosphorylated pBR322 vector (Bolivar et al., *Gene,* 2: 95–113 (1977)). The nucleotide sequence of the light- and heavy chain Fv coding region of monoclonal antibody B3 was determined from double stranded plasmid DNA using sequencing primers (New England Biolabs, Beverly, Mass., USA) adjacent to the BamHI or HindHIII site of pBR322 and a T7 polymerase sequencing reagent kit (United States Biochemicals, Cleveland, Ohio, USA).

TABLE 1

PCR primers used to amplify Fv heavy and light chains. The Fr1 primers were designed according to the amino acid sequences which were determined by Edman degradation, and are indicated in single letter code above the primer sequences. Underlined Met are initiator methionine codons. Other underlined amino acids in the light chain primers are segments of the peptide linker that fuses $V_H$ to $V_L$ in the single chain configuration. Underlined nucleotides in B1HFr1 and B5HFr1 encode the initiator methionine for expression in *E. coli*, and include an NdeI restriction site. Underlined nucleotides in B1HFr4 and B5HFr4 are complementary to the coding sequence for segments of the peptide linker that fuses $V_H$ to $V_L$ in the single-chain configuration. Underlined nucleotides in B1LFr4 B5LFr4 are complementary to the coding sequence of the junction between the Fv and PE38 and include a HindIII restriction site.

| Seq. Name | Sequence 5'-3' | ID |
|---|---|---|
| Heavy chain primers | | |
| B3-H1 | TAACTAGGATCCGTCCATATGGATGTGAAGCTGGTGGAGTCTGG | 1 |
| B3-H2 | TGGATAGACTGATGGGGATCCGCCTCCGCCTGAGGAGAC | 2 |
| B1HFr1 |           M  E  V  Q  L  V  E  S  G  G<br>GATATA<u>CATATG</u>GAGGTGCAGCTGGTGGAATCTGGAGGA | 40<br>3 |
| B5HFr1 |           M  E  V  K  L  V  E  S  G  G<br>GATATA<u>CATATG</u>GAGGTGAAGCTGGTGGAATCTGGAGGA | 41<br>4 |
| GammaCH1 | AGCAGATCCAGGGGCCAGTGGATA | 5 |

TABLE 1-continued

PCR primers used to amplify Fv heavy and light chains. The Fr1 primers were designed according to the amino acid sequences which were determined by Edman degradation, and are indicated in single letter code above the primer sequences. Underlined Met are initiator methionine codons. Other underlined amino acids in the light chain primers are segments of the peptide linker that fuses $V_H$ to $V_L$ in the single chain configuration. Underlined nucleotides in B1HFr1 and B5HFr1 encode the initiator methionine for expression in *E. coli*, and include an NdeI restriction site. Underlined nucleotides in B1HFr4 and B5HFr4 are complementary to the coding sequence for segments of the peptide linker that fuses $V_H$ to $V_L$ in the single-chain configuration. Underlined nucleotides in B1LFr4 B5LFr4 are complementary to the coding sequence of the junction between the Fv and PE38 and include a HindIII restriction site.

| Seq. Name | Sequence 5'-3' | ID |
|---|---|---|
| B1HFr4 | ACCGGATCCGCCTGCAGAGACAGTGAC | 6 |
| B5HFr4 | ACCGGATCCGCCTCCGCCTGAGGAGACAGTGAC/G | 7 |
| Light chain primers | | |
| B3-L1 | GTCTCCAAGCTTGGGGATCCGGTGGTGGCGGATCTGGAGGTGGCGGAAGCGATGTGCTGACCCAGTCTCC | 8 |
| B3-L2 | AGTTGGTGCAGCATCAAAAGCTTT[G/T]A[G/T][T/C]TCCAGCTT[T/G]GT[G/C]CC | 9 |
| B3-L3 | TTGGGGATCCGGTGGTGGCGGATCTGGA | 10 |
| B3-L4 | AGCGGGAATTCATTATTTAATTTCCAGCTTTGTCCCCGAC | 11 |
| B1LFr1 |     G  G  G  S  D  V  V  M  T  Q<br>GGTGGCGGAAGCGATGTTGTGATGACCCAA | 42<br>12 |
| B5LFr1 |     G  G  G  S  D  V  L  L  T  Q<br>GGTGGCGGAAGCGATGTTTTGTTGACCCAA | 43<br>13 |
| C-kappa | TGGTGGGAAGATGGATACAGTTGG | 14 |
| B1LFr4 | GGAAGCTTTCAGCTCCAGCTTGGT | 15 |
| B5LFr4 | GGAAGCTTTATTTCCAACTTTGT | 16 |

Example 2
Cloning of DNA Fragments Encoding the Heavy and Light Fv Segments of MAbs B1 and B5

To obtain DNA encoding the variable regions of the heavy and light chains of B1 and B5, Poly(A)+ mRNA was prepared from $10^5$ hybridoma cells and reverse-transcribed using random hexamers as primers to yield first strand cDNA. Separate PCR® reactions were carried out to amplify fragments encompassing heavy chain variable through part of CH1 domains, and light chain variable through part of C-kappa. The B1 and B5 $V_H$ sequences were amplified using 5' end primers designed according to the amino-terminal protein sequence of the B1 and B5 heavy chains and 3' end primers designed according to consensus immunoglobulin constant region sequences (Kabat et al. (1991) supra.). In particular, B1 $V_H$ was amplified using 5' end primer B1HFr1 and 3' end primer GammaCH1 (Table 1, SEQ ID NOS: 3 and 5 respectively). B5 $V_H$ was amplified using 5' end primer B5HFr1 and 3' end primer B5HFr4 (Table 1, SEQ ID NOS: 4 and 7 respectively). Primer GammaCH1 was designed according to consensus IgG1 CH1 region codons 122–129 while primer B1HFr4 was designed according to the determined nucleotide sequence of codons 109–113 of B1 $V_H$ (Kabat et al., (1991) supra.).

The B1 and B5 $V_L$ sequences were amplified using 5' end primers B1LFr1 and B5LFr1 (Table 1 and SEQ ID NOS: 12 and 13 respectively) which were designed according to the amino-terminal protein sequence of B1 and B5 light chains respectively (SEQ ID NOS: 20 and 22, respectively) in combination with the primer C-kappa (Table 1, SEQ ID NO: 14). Primer C-kappa was designed according to consensus kappa light chain codons 113–120 (Id.).

PCR was performed as described by Brinkmann et al., *Proc. Nat. Acad. Sci.* USA 88: 8616–8620 (1991).

The crude PCR products were subcloned into a PCR® cloning vector (Invitrogen, San Diego, Calif., USA) employing blue/white selection. Clones containing the correct size insert by DNA restriction analysis were identified. The nucleotide sequence of the heavy or light chain coding regions was determined from double stranded plasmid DNA using sequencing primers (Invitrogen) adjacent to the PCR® EcoRI cloning site and the Sequenase™ kit (United States Biochemical Corp). Three to five independent clones were sequenced for each amplified DNA segment. The nucleotide sequences of the B1 $V_H$ and $V_L$ are shown in Sequence ID NOS. 19 and 20 respectively, while the nucleotide sequences of the B5 $V_H$ and $V_L$ are shown in Sequence ID NOS. 21 and 22 respectively. B5 could not be amplified using a mu chain CH1 primer, so the consensus heavy chain B5HFr4 primer (Table 1, and SEQ ID NO: 7) was used instead. $V_H$ Primer B5HFr4 was designed according to consensus IgG1 Fr4 region codons 109–113 (Kabat et al., (1991) supra.)

Alignment of B1, B3 (Brinkmann et al., *Proc. Nat. Acad. Sci.* USA 88: 8616–8620 (1991)), and B5 Fv sequences revealed that B5 is highly homologous to B3 (91.6% identity in $V_H$ and 94.9% identity in $V_L$ coding sequence) and to the anti-Lewis$^Y$ antibody H18A (Kaneko et al., *J. Biochem.*, 113: 114–117 (1993)) (93.3 % identity in $V_H$ and 97.6% identity in $V_L$ coding sequence). B1 differs considerably both in framework and in CDR sequence from both B3 (83.9% identity in $V_H$ and 88.9% identity in $V_L$ coding sequence) and B5 (86.3% identity in $V_H$ and 91.2% identity in $V_L$ coding sequence), and does not show high sequence identity to any known anti-carbohydrate antibody in a database search (Devereux et al., *Nucleic Acids Res.*, 12: 387–395 (1984)). All three antibodies have a mouse class III heavy chain and a kappa II light chain (Kabat et al., supra). The differences in sequence between B1 and B3 may explain why they recognize different epitopes of otherwise similar antigens (see, Pastan et al., *Cancer Res.*, 51: 3781–3787 (1991) and U.S. Pat. No. 5,242,813).

Example 3

Construction of Plasmids for Expression of B3(Fv) and B3(Fv)-Immunotoxins A) Construction of B3(Fv) and B3(Fv)-PE40

The expression plasmid pVC38H contains the gene from the immunotoxin TGFα-PE40 under control of the T7 promoter (Chaudhary et al., *Proc. Natl. Acad. Sci.* USA 87: 1066–70 (1990)), the Tc transcription terminator at the 3' end of the PE40 coding region and the single strand replication origin, F$^+$, to generate single stranded phage DNA by cotransfection with (M13) helper phages, if desired, to create derivatives of the plasmid by site directed mutagenesis. The TGFα coding region in pVC38H has an NdeI recognition site at the 5' end and a HindIII site at the point of connection to the DNA encoding PE40.

To create a plasmid for expression of the immunotoxin B3 (Fv)-PE40 (pULEE3), the TGFα gene was removed and replaced by the B3(Fv) gene in a 3 -fragment ligation, using an NdeI/BamHI fragment of the heavy chain coding region and the BamHI/HindIII fragment encoding the light chain Fv (FIG. 1a). Because sequence analysis showed a mutation (deletion and frameshift) at the 5' end of the light chain Fv gene due to a sequence repetition in the PCR primer annealing region, site-directed mutagenesis was performed (Kunkel, *Proc. Natl. Acad. Sci.* USA, 82: 488–92 (1985)), using uridine incorporated single stranded phagemid DNA (pULEE3) as the mutagenesis template. In the resulting plasmid (pULI1), the correct amino end of the B3 light chain established by partial protein sequencing of monoclonal antibody B3, was reconstructed.

To make another B3(Fv) immunotoxin, B3(Fv)-PE38DKEL, the PE40 coding region was removed from pULI1 from the HindIII site to an EcoRI site positioned just beyond the PE40 gene, and replaced by a HindIII/EcoRI fragment from pRK79K encoding the PE variant PE38KDEL which lacks domain Ia (amino acids 1–252) and part of domain Ib (amino acids 365–380), and also contains an altered carboxyl terminal sequence KDEL (SEQ ID NO: 51) (Chaudhary et al., *Proc. Natl. Acad. Sci.*, 87: 308–12 (1990)). The expression plasmid pULI4 for production of B3(Fv) was constructed by removal of the light chain and PE40 coding region from pULI1 from BamHI to EcoRI which was replaced by a PCR fragment obtained by amplification of the light chain Fv coding sequence with the primer-pair B3–L3+B3–L4. The primer B3–L3 (Table 1) is similar to B3L1, used for cloning of light chain Fv from cDNA and B3–L4 (Table 1) is, in the 3' part for priming the PCR, identical to B3–L2, but, at the 5' end, the HindIII site for fusion to PE-sequences is replaced by translation stop codons followed by an EcoRI recognition sequence.

Figure 1B:
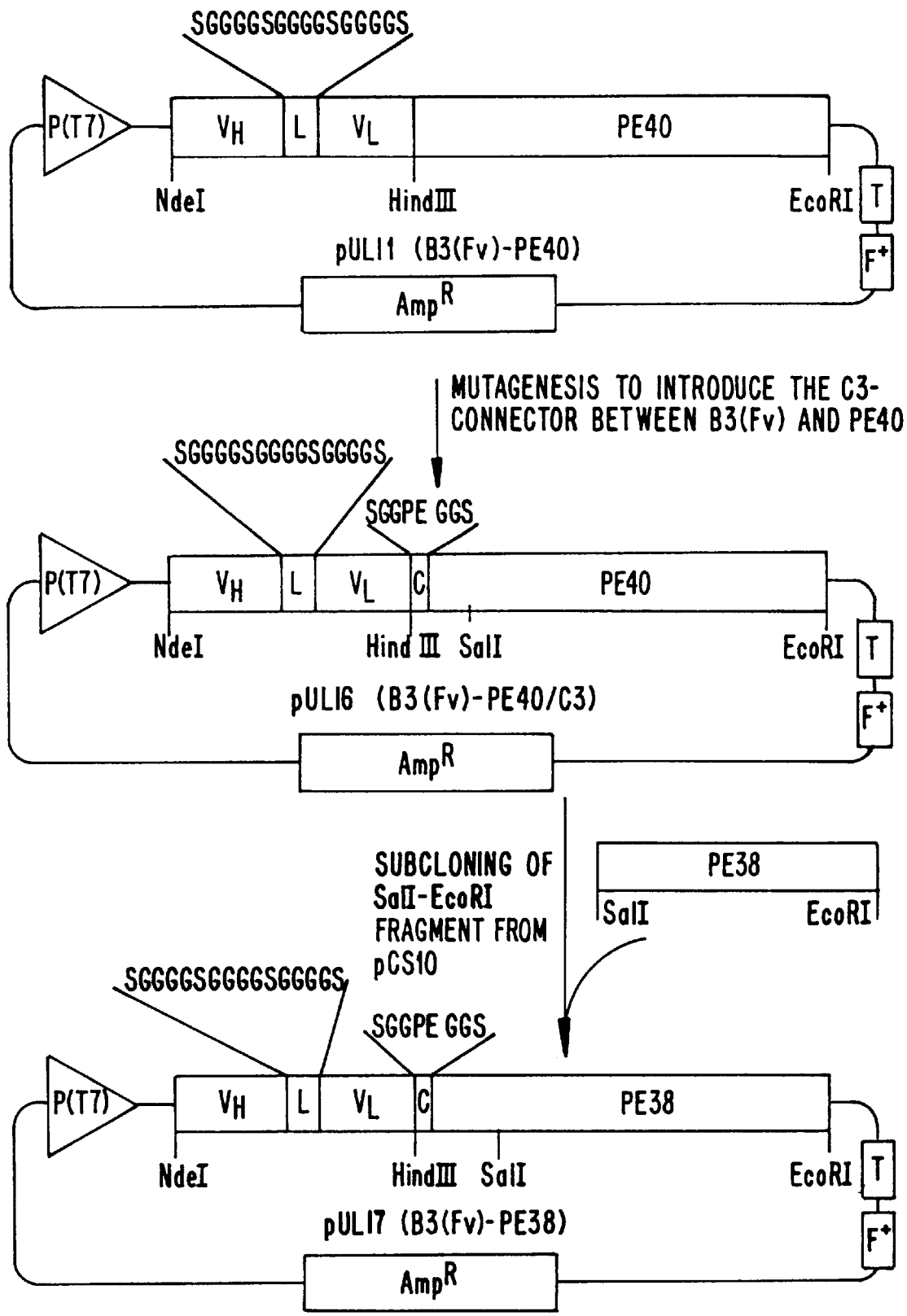
FIG. 1b shows the construction LMB7, the immunotoxin B3(Fv)-PE38 with a "C3 connector" between the Fv region and the PE38 cytotoxin (SGGGGSGGGGSGGGGSGGGGS linker=SEQ ID NO: 54; SGGPEGGS C3 connector=SEQ ID NO: 44).

B) Construction of pULI7, the Plasmind for Expression of LMB7, (B3(Fv)-PE38 with C3-Connector B3(Fv)-PE38, also called LMB7 is one recombinant B3(Fv)-immunotoxin of this invention preferred for use as a cancer therapeutic. The plasmid pULI7 for expression of B3(Fv)PE38 was constructed as follows: Plasmid pULI1 contains the Fv region of monoclonal antibody B3 in the form of a single chain Fv containing a (Gly$_4$Ser)$_3$ (SEQ ID NO: 3) peptide linker between $V_H$ and $V_L$, fused to PE-40, a truncated form of Pseudomonas exotoxin (see Brinkmann et al., *Proc. Nat. Acad. Sci.* USA 88: 8616–8620 (1991) and FIG. 1b). To improve folding and production of this molecule, a flexible "connector" peptide, designated C3, was added between the Fv and the toxin moiety by PCR mutagenesis (Brinkmann, et al. *Proc. Natl. Acad. Sci.* USA 89: 3075–3079 (1992)) to result in pULI6. Finally, part of the toxin portion of pULI6 was replaced with a shorter molecule with the same activity, PE38 (lacking domain Ib of PE), replacing by subcloning a SalI-EcoRI toxin fragment of pULI6 with the PE38 coding SalI-EcoRI fragment of pCS10 (Siegall et al. *J. Biol. Chem.*, 264: 14256–14261 (1989)). The resulting expression plasmid, which codes for the immunotoxin B3(Fv)-PE38 is pULI7 (FIG. 1b).

Example 4

Construction of Plasmids for Expression of B1(Fv)- and B5(Fv)-Immunotoxins

For expression as single-chain immunotoxins, B1 and B5 Fv fragments replaced B3Fv sequences in the expression plasmid pULI7 which encodes the B3(Fv)-PE38 immunotoxin (Benhar et al. *Bioconjug. Chem.*, 5:321–326 (1994)). For each Fv, the $V_H$ sequences were PCR amplified using the heavy chain clones in PCR® plasmids as templates. Primers B1HFr1 and 5'-phosphorylated B1HFr4 were used to amplify B1$V_H$, while primers B5HFr1 and 5'-phosphorylated B5HFr4 were used to amplify B5$V_H$. The $V_L$ sequences were amplified using the light chain clones in PCR® plasmids as templates. Primers B1LFr1 and 5'-phosphorylated B1LFr4 were used to amplify B5$V_L$, while primers B5LFr1 and 5'-phosphorylated B5LFr4 were used to amplify B5$V_L$. The primers had at their ends sequences that are complementary to the translation initiation, peptide linker and Fv-toxin junction (connector) which are common to the single-chain Fv-immunotoxin expression vectors. Primers B1LFr4 and B5LFr4 were designed according to the determined nucleotide sequence of codons 102–107 of B1 and B5 $V_L$ respectively. The PCR amplifications were performed as described in Example 2.

The PCR products were purified using spin columns, combined and annealed to a uracil-containing single-stranded DNA phagemid pULI7 which encodes the single-chain immunotoxin B3(Fv)-PE38. The phagemid was prepared by rescue of pULI7 phagemid with an M13MK07 helper phage (Bio-Rad, Hetcules, Calif., USA). The DNA was extended and ligated according to the MUTA-GENE® mutagenesis kit protocol (Bio-Rad).

Since the annealing efficiency of the PCR fragments to the single-stranded template, and hence the mutagenesis efficiency was relatively low (about 10%), an additional step was added. Plasmid DNA obtained from a pool of transformants from the mutagenesis reaction was digested with a restriction endonuclease which had a unique site in the B3Fv template, but whose site was absent from both B1 and B5. The digested DNA was used to re-transform *E. coli* cells. Following this extra step mutants were obtained with an efficiency greater than 80%. Correct clones were identified by DNA restriction analysis and verified by DNA sequencing. The resulting immunotoxin clones were named pB1 (Fv)-PE38 and pB5(Fv)-PE38.

Example 5
Expression and Purification of Recombinant B3(Fv)-Immunotoxins

Plasmids were transformed in the expression-host *E. coli* BL21 (λDE3) (Studier et al. *J. Mol. Biol.* 189: 113–30 (1986)). The bacteria were grown in superbroth containing 0.2–0.4% glucose, 0.05% $MgSO_4$, and 100 μg/ml ampicillin, induced in the log phase at $OD_{600}$ of 3.0 with 1 mM isopropyl-B-D-thiogalactopyranoside (IPTG) and harvested 90 min later. About 30% of the total protein of the induced cultures was the recombinant expression product which was deposited in inclusion bodies. The purified inclusion bodies contained almost pure recombinant protein, which had the expected size of about 67 kDa for a single chain immunotoxin. The recombinant immunotoxin molecules were solubilized, refolded, purified, and the protein was analyzed as previously described (Chaudhary et al., *Nature* 339: 394–97 (1989) & Batra et al., *J. Biol. Chem.* 265: 15198–202 (1990)). Protein concentrations were determined by Bradford assay (Bradford, *Anal. Biochem.* 72: 848–54 (1976)).

Example 6
Expression and Purification of B1(Fv)-PE38 and B5(Fv)-PE38

Cultures of *E. coli* (BL21λDE3, see Studier, et al. *J. Mol. Biol.* 189: 113–130 (1986)) were transformed with each expression plasmid to produce B1(Fv)- and B5(Fv)- immunotoxins. Following IPTG induction, the overproduced fusion proteins accumulated in inclusion bodies. These were isolated by solubilization and refolding of inclusion body protein using redox-shuffle as described (Buchner et al., *Anal. Biochem.* 205, 267–270 (1992)). Briefly, inclusion bodies were dissolved in 6M guanidine (HCl)/0.1M Tris (HCl) pH 8.0/2 mM EDTA and reduced by the addition of solid DTE to a final concentration of 65 mM at a protein concentration of 10 mg/ml. The solubilized and reduced inclusion body proteins were diluted ×100 into 0.1M Tris (HCl) pH 8.0/0.5M L-arginine/0.9 mM oxidized glutathione/2 mM EDTA and were allowed to refold for 36 hr at 10° C. The refolded proteins were extensively dialyzed against 20 mM Tris (HCl) pH 7.4/2 mM EDTA/0.1M Urea. Properly refolded proteins were separated from contaminating proteins and aggregates by sequential ion-exchange chromatography on Q-sepharose and Mono Q columns (Pharmacia, Piscataway, N.J., USA) followed by size exclusion chromatography on a TSK G3000SW (TosoHaas, Montgomeryville, Pa., USA) column. Typically, purified monomeric proteins were over 95% pure.

Example 7
Cytotoxic Activity of Chemically Linked and Recombinant B3(Fv)-Immunotoxins Assays measuring inhibition of protein synthesis were performed as previously described (Chaudhary et al., *Nature,* 339: 394–97 (1989) and Batra et al., *J. Biol. Chem.* 265: 15198–202 (1990)). All assays were performed in 96 well plates each well containing $1.6 \times 10^4$ cells in 200 μl medium. For competition assays designed to prove the specificity of the recombinant immunotoxins, the medium was changed and 50 μg/well of antibody was added 15 min prior to the addition of the immunotoxin.

Figure 3A:
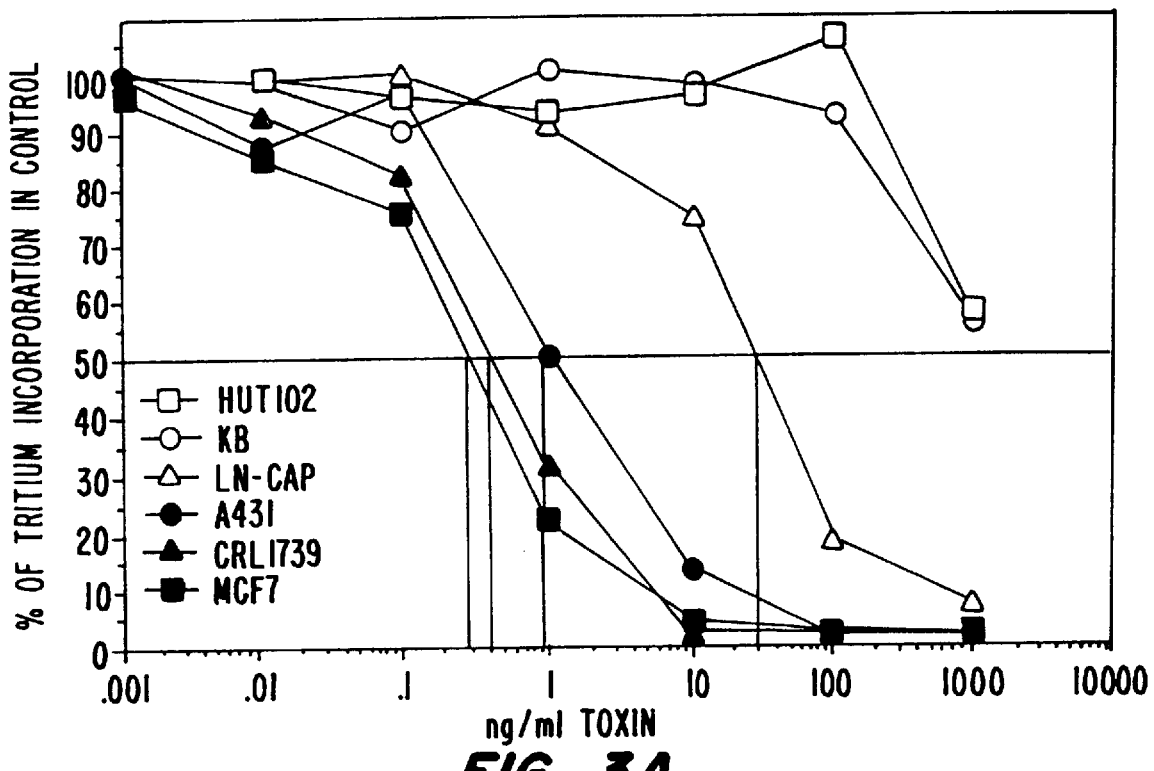
FIG. 3a represents the toxicity of B3(Fv)-PE38KDEL on different cell lines. Cytotoxicity assays were performed as described in Example 7.

As shown in FIG. 3a and in Table 2, the recombinant single chain immunotoxins inhibited protein synthesis in cells expressing the B3 antigen but not in non-expressing cells, similarly to the previously described results with chemical conjugate of B3 with a truncated form of PE (Pai et al., *Proc. Natl. Acad. Sci. USA,* 88: 3358–62 (1991)). The relative potencies of the chemical conjugate and the single chain immunotoxins were about the same on the four antigen positive cell lines MCF7, CRL1739, A431 and LNCaP. The most active agent was B3(Fv)-PE38KDEL.

TABLE 2

Activities of B3 immunotoxins on different cell lines. Cytotoxicity ($ID_{50}$) in ng/ml (pM).

| Cell Line | Cancer Type | B3 antigen | B3(Fv)-PE40KDEL | B3(Fv)-PE38 | B3-LysPE40 |
|---|---|---|---|---|---|
| MCF7 | breast | ++ | 3 (50) | 0.2 (3.2) | 3 (16) |
| CRL1739 | gastric | ++ | 3 (50) | 0.3 (5) | 3 (16) |
| A431 | epidermoid vulva | + | 3 (50) | 0.8 (13) | 8 (42) |
| LNCaP | prostate | + | 40 (1330) | 20 (325) | 85 (460) |
| KB3-1 | epidermoid cervix | − | >1000 | >1000 | >1000 |
| HUT102 | adult T cell leukemia | − | >1000 | >1000 | >1000 |

The recombinant single chain B3-Fv immunotoxins did not affect B3 antigen-negative control cells. The cytotoxicity of the recombinant B3(Fv)-PE40 ($ID_{50}$=50 pM; 3.0 ng/ml) was similar to the chemically linked B3-immunoconjugate ($ID_{50}$=42 pM; 8 ng/ml), whereas B3(Fv)-PE38KDEL was much more active than the chemical conjugate ($ID_{50}$=13 pM; 0.8 ng/ml). This is despite the fact that the single chain immunotoxins possess only one antigen binding site per molecule and the chemical conjugate has two (see Table 3 below).

TABLE 3

Structure and Activity of B3 Immunotoxins on A431 Cells.

| Immunotoxin | Toxin Part | C-Term | Binding | $ID_{50}$ |
|---|---|---|---|---|
| B3 chemical conjugate | PE40 | REDLK | bivalent | 8.0 ng/ml (42 pM) |
| B3(Fv) fusion protein | PE40 | REDLK | monovalent | 3.0 ng/ml (50 pM) |
| B3(Fv) fusion protein | PE38 | KDEL | monovalent | 0.8 ng/ml (13 pM) |

B3(Fv)-PE38KDEL has two features that distinguish it from B3(Fv)-PE40. One is that a portion of domain Ib encompassing amino acids 365–380 is deleted. This removes the disulfide bond formed between cysteine residues at positions 372 and 379, which might form disulfide bonds with other cysteines during the renaturation process and thereby result in the creation of inactive chimeric toxins. The second feature is that the carboxyl terminus of the toxin is changed from the original sequence REDLK (SEQ ID NO: 53) to KDEL (SEQ ID NO: 51). When the disulfide bond was removed in other molecules, the increase in activity was small. For example, TGFα-PE38 is only 50% more active than TGFα-PE40 (see Siegall et al., *J. of Biol. Chem.* 264: 14256–14261 (1989)). IL6PE38 is no more active than IL6-PE40. Changing REDLK (SEQ ID NO: 53) to KDEL (SEQ ID NO: 51) usually only produces a two to three fold increase in activity of chimeric toxins.

Figure 3B:
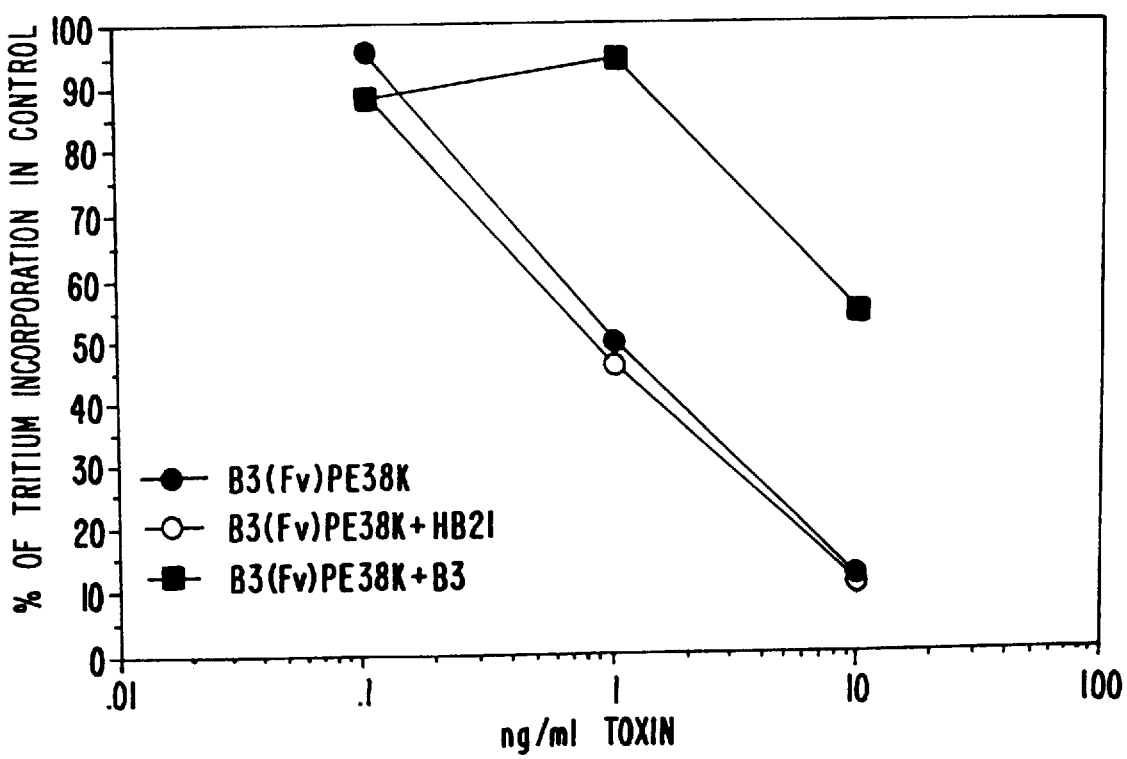
(FIG. 3b): Inhibition of the cytotoxicity of B3(Fv)-PE38KDEL by monoclonal antibody B3.

To analyze whether the cytotoxicity of B3(Fv)-immunotoxins was specific, competition experiments were carried out with an excess of monoclonal antibody B3. The data in FIG. 3b shows that the intoxication of A431 carcinoma cells by B3(Fv)-PE38KDEL is due to the specific binding to the B3 antigen, since its cytotoxicity was blocked by excess B3 but not by MAb HB21 which recognizes the transferrin receptor on these cells (Haynes et al., *J. Immunol.*, 127: 347–51 (1981)). A large excess of monoclonal antibody B3 is necessary for reversal of cytotoxicity, probably because there is a large amount of the B3 antigen on the surface of A431 cells (Pai et al., supra.)

Example 8
Antigen Binding, ADP-Ribosylation and Specific Cytotoxicity of Recombinant Immunotoxins A) ADP-Ribosylation Activity The ADP-ribosylation activity of each of the immunotoxins was to tested to verify that they were of equal enzymatic activity. ADP-ribosylation activity was determined by the incorporation on [$^{14}$C]-NAD into acid-precipitable material using elongation factor 2 enriched wheat-germ extract (Collier and Kandel, *J. Biol. Chem.*, 246: 1496–1503 (1971)). As shown in FIG. 4(A), B3(Fv)-PE38, which was used as a reference molecule, B1(Fv)-PE38 and B5(Fv)-PE38 had similar ADP-ribosylation activities.

B) Specific Cytotoxicity

Cytotoxicity towards A431 cells was measured by the inhibition of incorporation of [$^3$H]-leucine into cell protein, following 2 hours or 20 hours of incubation of the cells with serial dilutions of immunotoxins in PBS+0.2% BSA (see Brinkmann. et al., *Proc. Natl. Acad. Sci.* USA, 88: 8616–8620 (1991)). As shown in FIG. 4(B), when tested on A431 cells which strongly bind the B3 and the B1 MAbs, B3(Fv)-PE38 has an $IC_{50}$ of 2.8 ng/ml and 2.0 ng/ml following 2 or 20 hours incubation respectively. B1(Fv)-PE38 has an $IC_{50}$ of 0.6 ng/ml and 0.3 ng/ml following 2 or 20 hours incubation respectively. B5(Fv)-PE38 has an IC-50 of 120 ng/ml and 20 ng/ml following 2 or 20 hours incubation respectively.

To check the specificity of the immunotoxins, the same cytotoxic assay (Brinkmann et al. supra.) was done on additional cell lines. As shown in Table 4, B3(Fv)-PE38, B1(Fv)-PE38, and B5(Fv)-PE38 had the same spectrum of recognition of the cancer cell lines tested albeit having different levels of cytotoxic activity toward the antigen-positive cells, which correlates with the binding affinity of each immunotoxin toward its cellular binding site. These cell lines differ in their level of B3 or B1 antigen expression (Pastan et al., 1991; Brinkmann et al., 1993; see Table 4).

TABLE 4

Cytotoxicity of B1(Fv)PE38, B3(Fv)PE38, and B5(Fv)P8 toward various cell lines.

| Cell Line | Source | B1 or B3 antigen expression | B1(Fv)-PE38 | B3(Fv)-PE38 | B5(Fv)-PE38 |
|---|---|---|---|---|---|
| A431 | Epidermoid carcinoma | +++ | 0.3 | 2.0 | 20 |
| MCF7 | Breast carcinoma | +++ | 0.6 | 4.0 | 22 |
| LnCap | Prostate carcinoma | + | 2.7 | 21 | 210 |
| KB 3-1 | Cervical carcinoma | − | >1000 | >1000 | >1000 |
| HUT102 | T-cell leukemia | − | >1000 | >1000 | >1000 |
| L929 | Mouse fibroblast | − | >1000 | >1000 | >1000 |

C) Antigen Binding Affinity of B1(Fv)-PE38 and B5(Fv)-PE38

The specific antigen binding of the immunotoxins was further analyzed by determination of their binding affinity to antigen positive cells by competition assays, in which increasing concentrations of each immunotoxin were used to compete the binding of iodinated B3 IgG or B1 IgG to A431 adenocarcinoma cells at 4° C. as described by Benhar et al., *Bioconjug. Chem.*, (1994) supra). As shown in FIGS. 5a and 5b, B1(Fv)-PE38 competed for the binding of [$^{125}$I]-B1 IgG to A431 cells by 50% at 1.3 μM, and for the binding of [$^{125}$I]-B3 IgG by 50% at 1.7 μM. B3(Fv)-PE38 competed for the binding of [$^{125}$I]-B1 IgG to A431 cells by 50% at 2.7 μM, and for the binding of [$^{125}$I]-B3 IgG by 50% at 2.5 μM. B5(Fv)-PE38 competed for the binding of [$^{125}$I]-B1 IgG to A431 cells by 50% at about 50–100 μM, and for the binding of [$^{125}$I]-B3 IgG by 50% at 50 μM. B1 IgG competed by 50% for the binding of $^{125}$I labeled B1 IgG at 110 nM and B3 IgG competed by 50% for the binding of $^{125}$I labeled B3 IgG at 200 nM (not shown).

The analyses of the B1(Fv)-PE38 and B5(Fv)-PE38 and their comparison with B3(Fv)-PE38 showed that all three had similar ADP-ribosylation activities (FIG. 4(A)), indicating that cytotoxic activity differences between the immunotoxins did not result from different enzymatic activity, but instead reflect relative antigen binding affinities. The cytotoxic assays (FIG. 4(B) and Table 4), show that the cytotoxic activity of B1(Fv)-PE38, B3(Fv)-PE38 , and B5(Fv)-PE38, is specific, as they all kill antigen positive cells, whose sensitivity to intoxication is proportional to the level of antigen expression, while antigen-negative cells are spared. The activities of the immunotoxins varied with B1(Fv)-PE38 being the most potent. In a 20 hr assay B1(Fv)-PE38 had an $IC_{50}$ of 0.3 ng/ml on A431 cells, and B5(Fv)-PE38 was the least potent, with an $IC_{50}$ of 20 ng/ml on A431 cells.

The antigen binding assays (FIG. 5) showed that apparently B1 and B5 recognize the same antigen as B3, because all three immunotoxins compete for the binding of $^{125}$I labeled B1 IgG and B3 IgG. However, the possibility of each recognizing a different epitope of a mutual antigen can not be excluded. A clear correlation was observed between each immunotoxins' antigen binding affinity and its cytotoxic potency. The relative low affinity of B5(Fv)-PE38 is consistent with its being derived from an IgM.

Example 9
Stability of Immunotoxins

The stability of the B1(Fv)-, B3(Fv)- and B5(Fv) immunotoxins following heat treatment was determined by incubation at 0.1 mg/ml in PBS at 37° C. for 4 hours, followed by analytical chromatography on a TSK G3000SW (TosoHaas) column, to separate the monomers from the aggregates. Cytotoxic activities of aliquots of heat treated immunotoxins were determined as described above, and compared to the activities of the untreated immunotoxins.

As shown in FIG. 6(A), all three immunotoxins were monomeric before the incubation (FIG. 6(A), broken lines), whereas after 4 hours of incubation in PBS at 37° C., about half B1(Fv)-PE38 and B5(Fv)-PE38 were aggregated, and B3(Fv)-PE38 was completely aggregated (FIG. 6(A), solid lines). As shown in FIG. 6(B), following the 4 hours 37° C. treatment, B1(Fv)PE38 had an $IC_{50}$ of 1.8 ng/ml which is 25% of its cytotoxic activity before treatment. B5(Fv)-PE38 had an $IC_{50}$ of 30 ng/ml (FIG. 6(B)) which is 66% of its cytotoxic activity before treatment. No cytotoxic activity could be detected after treatment of B3(Fv)-PE38 for 4 hours at 37° C.

These stability assays reveal differences in stability among the single-chain Fv-immunotoxins tested here. This is evident both from the cytotoxicity assay (FIG. 6(B)) and the from the stability assay (FIG. (6)). The B3(Fv)-PE38 is somewhat unstable at 37° C. (Benhar et al., 1994 supra;

Brinkmann et al., Proc. Natl. Acad. Sci. USA, 90: 7538–7542 (1993)) and undergoes inactivation mainly by aggregation. As a consequence it shows little difference in cytotoxic activity when incubated 2 or 20 hours on A431 cells, because most of the immunotoxin is inactivated after 2 hours. B1(Fv)-PE38 is more stable, as indicated by the fact that its cytotoxic activity following 20 hours incubation on A431 cells is twice the activity following a 2 hour incubation, and by its reduced aggregation and inactivation following incubation at 37° C. B5(Fv)-PE38 may be the most stable as its cytotoxic activity following 20 hours incubation on A431 cells is six fold higher than the activity after a 2 hour incubation. B5(Fv)-PE38 seems to aggregate as much as B1(Fv)-PE38 in the absence of antigen, but, when incubated with cells, it appears to be more resistant than both B1(Fv)-PE38 and B3(Fv)-PE38 to inactivation following incubation at 37° C. Since the antigen binding studies were done at 4° C. for three hours, conditions under which all three immunotoxins are stable, the relative binding affinities of the immunotoxins best correlate with their relative cytotoxic activities following a 2 hour incubation period.

Example 10
Assay of Blood Levels of B3(Fv)-PE38KDEL in Mice

Six week old (19–20 gm) female Balb/c mice were injected with 10 μg of B3(Fv)-PE38KDEL in the tail vein. Blood was drawn at various time intervals and the level of the immunotoxin measured by incubating serum with A431 cells and measuring inhibition of protein synthesis. A standard curve was made with pure B3(Fv)-PE38KDEL and the blood level of immunotoxin (which is shown in FIG. 7) calculated using this curve.

Example 11
Anti-tumor Activity of B3(Fv)-PE38KDEL in Nude Mice Bearing a Human Epidermoid Carcinoma A431 cells (3–10$^6$) were injected subcutaneously on day 0 into female nude mice (4–6 weeks old, 18–20 gm). Mice with 5 mm by 5 mm tumors, that usually developed by day 4, were treated with B3(Fv)-PE38KDEL or, as a control, with MAbB3 or antiTac(Fv)-PE38KDEL (Chaudhary et al., Nature 339: 39497 (1989)). Because the lifetime of B3(Fv)-PE38KDEL in the circulation of the mice was observed to be only 15–20 min (FIG. 7), six injections were given at 12 hour intervals into the tail vein, starting 4 days after tumor implantation. Each treatment group consisted of five animals. The volume of the tumor was calculated by (tumor volume in cm$^3$=length×width$^2$×0.4).

As shown in FIG. 8, injection of either 2.5, 5 or 10 μg twice daily produced complete tumor regression despite the fact that B3(Fv)-PE38KDEL has a short lifetime (15–20 min) in the circulation. Partial regression was observed when only 0.5 μg was injected. No toxicity was observed at these doses. In addition, when mice with large tumors about 1 cm in diameter were treated with 5 μg twice a day for 4 days, complete regression of these large tumors containing about 5×10$^4$ cells rapidly occurred (FIG. 8(D)). Previously, it was found that even the administration of 75 μg per day for 5 days of a chemical conjugate composed of B3 and PE40 (see Table 3) only produced partial regression of large tumors despite the fact that the chemical conjugate has a much longer lifetime in the blood (4 hours). The recombinant molecule probably has a higher antitumor activity in the mouse model because of its small size which allows better access to tumor cells. Regression of MCF-7 tumors (breast carcinoma) also was observed with 5 μg twice daily of B3(Fv)-PE38KDEL.

Example 12
Chimeric Fv Region Immunotoxins and Mutated Immunotoxins Show Increased Stability In order to investigate the mechanism contributing to the greater stability of B5(Fv)-PE38 as compared to B3(Fv)-PE38 immunotoxins comprising chimeric Fv regions in which the light and heavy chains were derived from different antibodies were constructed as described below. In addition, B3(Fv)-PE38 immunotoxins carrying $V_L$ mutations M4L (in which methionine 4 is replaced with leucine) and S7T (in which serine 7 is replaced with threonine) in combination or separately were prepared. The cytotoxicity and stability of the chimeric Fv and mutated fusion proteins was then determined.

A) Cloning and Expression of Chimeric Fv and Mutated Immunotoxins

To produce chimeric Fv immunotoxins, DNA encoding the variable regions of the heavy and light chains of B5 was prepared from mRNA obtained from B5 hybridoma cells as described in Example 2. To generate single chain immunotoxins with Fvs of B5, the $V_H$ and $V_L$ fragments were PCR amplified using phosphorylated primers to enable the ligation of extended PCR products (see Example 2). The resulting PCR products were used as "primers" in a "domain shuffling" scheme where they replaced the corresponding B3(Fv) $V_H$ or $V_L$ regions or both, generating single chain Fv-toxin expression plasmids having B3$V_H$-B5$V_L$, B5$V_H$-B3$V_L$, and B5Fv (FIG. 9). The extension of template-primer, ligation, transformation and analysis of clones are described in Examples 2 and 4. This procedure resulted in the generation of plasmids for expression in E. coli in which either the $V_H$ or the $V_L$ domains of B3 were replaced by the corresponding domains from B5 (FIG. 9).

In addition, plasmids expressing B3(Fv)-PE38 derivatives carrying $V_L$ mutations M4L and S7T in combination or separately, were prepared by site-specific mutagenesis (Kunkel, et al. Proc. Natl. Acad. Sci. USA, 82: 488–492 (1985)). In addition, similar plasmids expressing B3(Fv)-PE38 derivatives carrying $V_L$ mutations M4L and S7r together or separately were prepared by site-specific mutagenesis using oligonucleotide primers.

Plasmids encoding B3(Fv)-PE38, B5$V_H$-B5$V_L$-PE38, B5$V_H$-B3$V_L$-PE38, B5(Fv)-PE38 or mutated B3(Fv)-PE38 were expressed and the fusion protein purified as described in Example 6. Typically, monomeric proteins were recovered that were over 95% pure.

B) Specific cytotoxicity of recombinant immunotoxins

The cytotoxic activity of B3(Fv)-PE38 and its derivatives was assessed, according to the method of Brinkmann et al., Proc. Nat. Acad. Sci. USA 88: 8616–8620 (1991), by measuring the incorporation of [$^3$H]-leucine by various human carcinoma cell lines after treatment with serial dilutions of the immunotoxin in phosphate buffered saline (PBS) containing 0.2% BSA as described in Example 8.

When tested on A431 cells, which strongly bind monoclonal antibody B3, B3(Fv)-PE38 has an IC$_{50}$ of 2.8 ng/ml and 2.0 ng/ml following 2 or 20 hours incubation respectively. B3$V_H$-B5$V_L$-PE38 and B3(Fv)-PE38 $V_L$: M4L S7T are more active and have identical IC$_{50}$s of 0.6 ng/ml and 0.3 ng/ml following 2 or 20 hours incubation respectively. B5(Fv)-PE38 is much less active with an IC$_{50}$ of 120 ng/ml and 20 ng/ml following 2 or 20 hours incubation respectively. B5$V_H$-B$^3V_L$-PE3$^8$ has an IC$_{50}$ of 200 ng/ml and 120 ng/ml following 2 or 20 hours incubation respectively (data not shown).

C) Stability of the recombinant immunotoxins

The stability of B$^3V_H$-B5$V_L$-PE38, and B$^3$(Fv) PE3$^8$;$V_L$M4L S7T were tested and compared to that of B3(Fv)-PE38 by determination of their respective levels of aggregation and inactivation at 37° C. as described in Example 9. All three immunotoxins were principally monomeric before incubation at 37° C. After one hour of incubation in PBS at 37° C., about half of B3V$_H$-B5V$_L$-PE38 and B3(Fv)PE38 V$_L$: M4L S7T were aggregated, whereas B3(Fv)-PE38 was about 75% aggregated. After 2 hours of incubation in PBS at 37° C., 60% of B3V$_H$-B5V$_L$-PE38 and B3(Fv)-PE38 V$_L$: M4L S7T were aggregated, and B3(Fv)-PE38 was >80% aggregated. After 4 hours of incubation in PBS at 37° C., about 80% B3V$_H$-B5V$_L$-PE38 and B3(Fv)-PE38 V$_L$: M4L S7T had aggregated, whereas B3(Fv)PE38 was almost completely aggregated.

The cytotoxic activities of these immunotoxins are shown in FIG. 10. Following the 1 hour incubation at 37° C. in PBS, B3(Fv)-PE38 had an IC$_{50}$ of 8 ng/ml which is 25 % of its cytotoxic activity before treatment. After 2 hours at 37° C., it had an IC$_{50}$ of 200 ng/ml which is about 1% of its cytotoxic activity before treatment. Both B3V$_H$-B5V$_L$-PE38 and B3(Fv)-PE38: V$_L$M4L S7T cytotoxic activities after one hour at 37° C. in PBS were similar to their pretreatment activities. After 2 hours they showed an IC$_{50}$ of 3.5 ng/ml which is 12% of their cytotoxic activity before treatment.

The lower IC$_{50}$ of the chimera and the mutant can be explained by the fact that both are more stable that the wild type B3(Fv)-PE38. This improved stability was evident from their slower aggregation and loss of cytotoxic activity upon incubation in PBS at 37° C. Very little B3(Fv)-PE38 monomer survives a 2 hours incubation, whereas the stabilized variants survive for a longer time. This correlates with the fact that while B3(Fv)-PE38 cytotoxic activity is only slightly increased if A431 cells are expressed to it for 20 hours instead of two hours, whereas the stabilized variants show a 3 fold increase upon a 20 hour incubation when compared to a 2 hour incubation on A431 cells.

Site specific mutagenesis was used to identify which of the three V$_L$ residues that differ between B3 and B5 was previously responsible for the stabilizing effect. Since B3V$_H$-B5V$_L$-PE38 and B3(Fv)-PE38: V$_L$M4L S7T (which differs from the chimera only at the fourth CDR1 residue) had identical characteristics in the assays, the CDR residue is not the stabilizing one. Analysis of B3(Fv)-PE38 derivatives carrying mutations V$_L$ M4L or V$_L$ S7T separately showed that replacing V$_L$ methionine 4 with leucine stabilized the immunotoxin as much as the B$^3$V$_H$-BSV$_L$-PE38 combination, whereas replacing V$_L$ serine 7 with threonine had no stabilizing effect (data not shown).

A binding study using a BioCore instrument indicated that B3(Fv)-PE38: V$_L$ M4L S7T has a similar off rate to that of B3(Fv)-PE38 (0.0023 and 0.0021, respectively) whereas the on rates differ (1150 and 984, respectively). The apparent Kd is 2.33×10$^{-6}$ for B3(Fv)-PE38 and 1.84×10$^{-6}$ for B3(Fv)-PE38: V$_L$ M4L S7T. This data correlates with binding data obtained by competition with $^{125}$I B3 IgG.

Example 13
Humanization of the B3(Fv) Antibody

B3(Fv) was humanized by a process of "framework exchange". As will be explained in detail below, the variable domains of the heavy and light chains were aligned with human antibody sequences and, by comparison of each domain with its best human homolog, framework residues that differed between the mouse B3 and its human homolog were identified. Eleven framework residues in V$_H$ and eight in V$_L$ were changed by site-specific mutagenesis to human residues and introduced simultaneously into a pre-assembled single-chain Fv (scFv) expression cassette.

A) Identification of Residues for Humanization

A structural model of B3(Fv) was constructed based on the crystal structure of the variable domains of monoclonal antibody McPC603 (Satow et al., *J. Mol. Biol.*, 190: 593–604 (1986); Abola et al., pp. 107–132 in *Crystallographic databases-information content*, Software Systems, Scientific Application, eds. Allen, Bergerhoff, & Sievers, Data Comm. of the Intl. Union of Crystallogr., Bonn (1987); Protein Data bank Entry IMCP), which was modified and refined by an energy minimization algorithm using the program CHARMM (Brooks et al., *J. Comput. Chem.*, 4: 187–217 (1983)) version 22. The construction of this refined model in described in detail elsewhere (Jung et al, *Protein Structure Function and Genetics*, 19: 35–47 (1994)). The amino acid sequences of B3 V$_H$ and V$_L$ were independently aligned with all the human antibody sequences contained in the SWISS-PROT Data Base using the FASTA program (Release 27.0 10/93) (Devereux et al., *Nucleic Acids Res.* 12: 387–395 (1984)).

The V$_H$ of the human fetal immunoglobulin 56P1'CL (Schroeder et al., *Science*, 238: 791–793 (1987)) had the highest overall sequence identity and had the highest identity in the framework regions. The alignment of B3 V$_H$ with 59P1'CL VH is shown in FIG. 11a. The V$_L$ of the human IgM GM607 (Klobeck et al., *Nature*, 309, 73–76 (1984)) (SWISSPROT file sw:kv2e-human) scored fourth in overall sequence identity (77.7%), but had the highest identity in the framework regions. The alignment of B3 V$_L$ with GM603 V$_L$ is shown in FIG. 11b. The amino acid residues that differ are identified in FIGS. 11a, 11b and 11c by vertical lines above the sequence. Based on experiments with B3(Fv)-PE38 mutants (Benhar, unpublished), and on the analysis of B3Fv using the structural model, it was decided to preserve the mouse residues at V$_H$ positions 1, 3, 19, 24, 89, and 91 and V$_L$ positions 2, 3 and 41 (Kabat, et al. *Sequences of proteins of immunological interest*. 5th edition. U.S. (1991); FIGS. 11a, 11b, and 11c). These residues are identified by asterisks in FIGS. 11a and 11b, some of them are inter-domain residues and others are buried and therefore are not expected to be part of an immunogenic epitope (Padlan, *Mol. Immunol.* 28: 489–498 (1991) and Roguska et al. *Proc. Natl. Acad. Sci.* USA, 91: 969–973 (1994)).

The human antibodies chosen also had similarity to B3(Fv) in the sequence of the complementarity determining region loops (CDRs), and had the same CDR length which further indicates that they belong to a similar structural group, and possibly have a similar canonical structure of the CDR loops (Chothia et al., *J. Biol. Chem.* 227: 799–817 (1992); Williams et al., *Eur. J. Immunol.* 23: 1456–1461 (1993)).

B) Construction of plasmids expressing humanized variants of B3(Fv)PE38

B3 V$_H$ and V$_L$ gene segments in plasmid pULI7 (FIG. 13(A)) encoding wild type B3(Fv)-PE38 was selected for modification via site-directed mutagenesis. Uracil-containing single-stranded DNA was prepared by rescue of our F+ origin containing plasmids with an M13KO7 helper phage and was used as a template for site-specific mutagenesis (Kunkel, *Proc. Natl. Acad. Sci.* USA, 82: 488–492 (1985)). The complete nucleotide sequence of the gene encoding B3(Fv)-PE38 has been described (Brinkmann, et al., *Proc. Natl. Acad. Sci.* USA, 88: 8616–8620 (1991)). Mutagenic oligonucleotides used and the mutation, they are listed in Table 5.

Figure 12C:
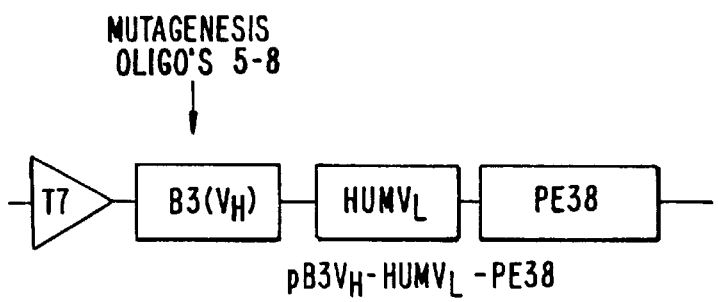
Figure 12D:
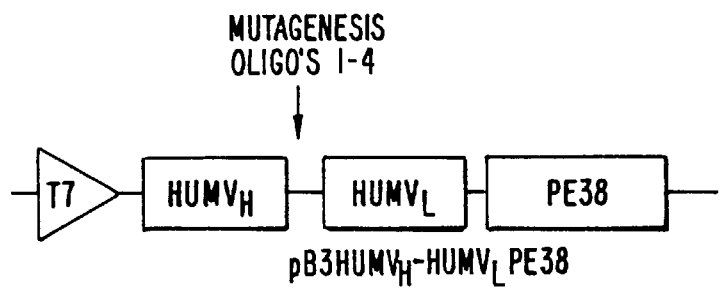

B3 $V_H$ and $V_L$ gene segments in plasmid pULI7 (FIG. 12(A)), encoding wild type B3(Fv)-PE38, were independently humanized by site specific mutagenesis. A set of four oligonucleotides was used to simultaneously introduce the mutations into each segment, with most of the oligonucleotides changing more than one mouse to human codon. In B3 $V_H$, the mutations introduced were L11V and G16R, T40A, E42G and R44G, A74S and R75K, S82aN, R82bS, K83R and S84A. The resulting plasmid was pB3HUMV$_H$-V$_L$-PE$^{38}$ (FIG. 12(B)). In B3 $V_L$, the mutations introduced were S14T, L15P, D17E and Q18P, K45Q, L83V, S100Q and L104V. The resulting plasmid, pB3HUMV$_H$-V$_L$-PE38 (FIG. 12(C)) was used as a template for a second mutagenesis with the combined heavy chain mutagenic oligonucleotides generating plasmid PHUMV$_H$-HUMV$_L$-PE38 (FIG. 12(D)), which encodes the humanized B3(Fv) single-chain immunotoxin. The residues that were mutated are identified in FIG. 11 by their numbers.

C) Expression and Purification of Recombinant Proteins

Expression plasmids encoding B3(Fv)-PE38 or its humanized derivatives were introduced into *E. coli* strain BL21 (λDE3) (Studier et al. *J. Mol. Biol.* 189, 113–130 (1986)) and the recombinant proteins were expressed as inclusion bodies as described in Example 6. The single-chain immunotoxins were obtained by solubilization and refolding of inclusion body protein as described and subsequently purified as described in Example 6. Typically, the monomeric proteins were obtained at over 95% purity, as determined by non-reducing SDS-PAGE of the product.

B3(Fv)-PE38 had an IC$_{50}$ of 1.8 ng/ml on A431 cells which express high levels of the B3 antigen. The variant B3V$_H$-HUMV$_L$-PE38(HUM$_L$) had a similar cytotoxic activity, while B3HUMV$_H$-V$_L$-PE38 (HUM$_H$) and B3-HUMV$_H$-HUMV$_L$-PE38 (HUM$_{H+L}$) had IC$_{50}$s of about 4.4 ng/ml.

To check whether humanizing B3(Fv)-PE38 caused a change in antigen specificity, the same cytotoxic assay was done on additional cell lines. As shown in Table 6, B3(Fv)-PE38 and all the humanized variants had the same spectrum of recognition of the cell lines used. These cell lines differ in their level of B3 antigen expression (Brinkmann et al., *Proc. Natl. Acad. Sci. USA*, 90: 7538–7542 (1993)). This result indicates that the antigen binding specificity of the B3(Fv) was not altered by the humanizing process.

The specific antigen binding affinity of the B3(Fv) immunotoxins was further analyzed by determination of the binding affinity of B3(Fv)-PE38 and the humanized variants to B3 antigen bearing cells by a competition assay, in which increasing concentrations of each immunotoxin were used to compete for the binding of [$^{125}$I]-B3 IgG to A431 cells at 4° C. As shown in FIG. 13c, both B3(Fv)-PE38 and HUM$_L$ blocked the binding of [$^{125}$I]-B3 antibody to A431 cells by 50% at 1–2 μM. However, HUM$_H$ and HUM2$_{H+L}$ had a lower affinity, and competed by 50% at 4–5 μM. The results from the cytotoxicity and the binding assays indicate that the humanized B3(Fv) suffered a 2–3 fold loss in antigen binding affinity and that the damaging mutation probably resides in the $V_H$ segment.

TABLE 5

Oligonucleotides utilized for site directed mutagenesis and the mutations they introduced. Restriction sites which were introduced into these oligonucleotides to facilitate identification of mutated clones are underlined.

| Primer | Sequence | Mutation | Seq. ID. No. |
|---|---|---|---|
| 1 | 5'-GGAGAGTTTCAGGGAGCGCCCGGGGTGC ACGACGCCTCCCCC-3', | V$_H$: L11V; G16R | 23 |
| 2 | 5'-TGCGACCCACTCCAGGCCCTTGCCCGGG GCCTGGCGAACCCAATA-3' | V$_H$: T40A; E42G; R44G | 24 |
| 3 | 5'-GAGGGTGTTCTTGCTATTGTCTCTAGAG ATGGTGAACCG-3' | V$_H$: A74S; R75K | 25 |
| 4 | 5'-TATGGCTGTGTCCTCGGCGCGCAGGCTG TTCATTTGCAGGTA-3' | V$_H$: S82aN; R82bS; K83R; S84A | 26 |
| 5 | 5'-GCAAGAGATGGAGGCCGGCTCTCCCGGG GTGACAGGTAAACTCAA-3' | V$_L$: S14T; L15P; D17E; Q18P | 27 |
| 6 | 5'-AACTTTGTAGATCAGCAGCTGTGGAGAC TGGGCTGG-3' | VL: K45Q | 28 |
| 7 | 5'-GCAGTAATAAACTCCGACGTCCTCAGCC TCCAC-3' | V$_L$: L83V/ | 29 |
| 8 | 5'-GGAAGCTTTAATTTCGACCTTGGTACCC TGGCCGAACGTGAATGG-3' | V$_L$: S100Q L104 | 30 |

D) Cytotoxicity and Binding Affinity of Humanized B3(Fv)-P38

The ADP-ribosylation activity of each immunotoxin was tested, to verify that they are of equal enzymatic activity. As shown in FIG. 13a, B3(Fv)-PE38 and the humanized variants had similar ADP-ribosylation activities.

The cytotoxic activity of B3(Fv)-PE38 and of its humanized variants was measured by incubating various human carcinoma cell lines with serial dilutions of the immunotoxin, and measuring the incorporation of [$^3$H]-leucine as described in Example 8. As shown in FIG. 13b,

TABLE 6

Cytotoxicity of recombinant B3(Fv)PE38 and
its humanized variants toward various cell lines.

| Cell Line | Source | B3 antigen expression | B3 (Fv)PE38 | $HUM_L$ | $HUM_H$ | $HUM_{H+L}$ | HUMFv |
|---|---|---|---|---|---|---|---|
| A431 | Epidermoid carcinoma | +++ | 1.8 | 1.9 | 4.4 | 4.2 | 2.2 |
| MCF7 | Breast carcinoma | +++ | 4.0 | 3.8 | 8.2 | 8.5 | 4.2 |
| LnCap | Prostate carcinoma | + | 35 | 30 | 110 | 90 | 300 |
| KB 3-1 | Cervical carcinoma | − | >1000 | >1000 | >1000 | >1000 | >1000 |
| HUT102 | T-cell leukemia | − | >1000 | >1000 | >1000 | >1000 | >1000 |
| L929 | Mouse fibroblast | − | >1000 | >1000 | >1000 | >1000 | >1000 |

Cytotoxicity data are given as $IC_{50}$ values, the concentration of immunotoxin that causes a 50% inhibition of protein synthesis following it's incubation on the cells for 20 hours. Expression level estimation of the B3 antigen is based on immunofluorescence. +++, strong; + weak; −, not detected. The immunotoxins used are B3(Fv)PE38, $B3V_H$-$HUMV_L$-PE38 ($HUM_L$), $B3HUMV_H$-$V_L$-PE38 ($HUM_H$), $B3HUMV_H$-$HUMV_L$-PE38 ($HUM_{H+L}$), HUMB3 (Fv)-PE38 (HUMFv). All cell lines except L929 are of human origin.

E) Back-Mutating $V_H$ Residue 82b to Restore Activity

To restore the reduced activity of $HUM_{H+L}$, some mutated forms which were partially humanized in the VH region were tested for cytotoxic activity. It was found that a mutant of B3(Fv)-PE38 in which the $V_L$ was wild type and $V_H$ residues at positions 74, 75 or 83 were humanized, did not lose cytotoxic activity, while a derivative in which residues 74, 75 and 82a, 82b, 83, and 84 were humanized was about 5–6 fold less active. In the B3 $V_H$ structural group (mouse III(A)) residue 82a is most commonly asparagine, as it is in $HUM_{H+L}$. However, serine is never found at position 82b. Furthermore, the original residue at position 82b, arginine, is acceptable in human IgGs. Therefore, residue 82b in $HUM_{H+L}$ was mutated to arginine by site-specific mutagenesis. The resulting molecule is named HUMB3(Fv)-PE38. The protein was purified to near homogeneity and was subjected to activity and binding assays. As shown in FIG. 13a, its ADP-ribosylation activity did not differ significantly from that of the other immunotoxins. Moreover, as shown in FIGS. 13b, 13c, and Table 6, its cytotoxic and antigen binding activities were improved relative to $HUM_{H+L}$ and were similar to those of the original B3(Fv)-PE38 immunotoxin.

Example 17
Reactivity with Sera from Monkeys Immunized with B3(Fv)-PE38

Sera obtained from monkeys that had been immunized with B3(Fv)-PE38 contain antibodies to PE38 as well as a lower reactivity with B3Fv. To assess the success of humanizing B3Fv, sera from four Cynomolgus monkeys containing specific anti B3(Fv)-PE38 titers (Id.) were pooled and used in an ELISA assay on plates that were coated with B3(Fv)-PE38, $HUM_{H+L}$, or HUMFv (B3HUMFv). An excess of PE38 was included as a competitor to preadsorb reactivity which is directed against the toxin moiety of the molecule. As shown in FIG. 14, the anti B3(Fv)-PE38 sera had a weaker reaction against both $HUM_{H+L}$ and HUMFv than with the wild-type B3(Fv)PE38, indicating that primate B3(Fv) epitope(s) were missing in the humanized variants.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

Example 18
The $V_H$ Tyrosine to Serine Mutation Improves the Affinity of Anti-$Le^Y$ Carbohydrate Antibodies When comparing the amino acid sequence of B3 to the conserved framework sequences of other antibodies (Kabat et al. (1991) supra.) it was observed that a tyrosine at position $V_H$ 95 was exchanged to serine, which is very unusual. To investigate the significance of this exchange, this residue was mutated to tyrosine or to phenylalanine, which are the amino acids that are mostly present at this position in other antibodies. It was found, that both exchanges reduced the affinity of B3(Fv) compared to the molecule with the original serine approximately 10 fold. Thus, the serine is important for high affinity binding. This was unexpected and surprising, because position $V_H$ 95 is in the $V_H$-$V_L$ interface, and thus neither in the binding region nor close to it (see, commonly assigned U.S. patent application Ser. No. 08/077,252 filed on Jun. 14, 1993). This excludes the possibility that a direct (contact) effect of the serine, influences binding. The most likely explanation for the effect of the serine is, that, because it is positioned in the $V_H$-$V_L$ interface and slightly destabilizes the interface contacts it enables a movement of $V_H$ relative to $V_L$, mediating a so called "induced fit" antibody binding mode (Rini et al., Science, 255: 959–965 (1992) and Stanfield et al, Structure, 1: 83–93 (1993)). To analyze whether the "serine mutation" at $V_H$ 95, which was found in B3(FV) increases only the affinity of B3(Fv) or if it can (possibly by mediating induced fit) also increase the affinity of other $Le^Y$ binding antibodies, we introduced this mutation into B5(Fv). B5 Fv binds like B3 $Le^Y$ but contains a different antibody binding site, and in addition contains the "conserved" tyrosine in position $V_H$ 95. Exchange of this tyrosine to serine was done by site directed mutagenesis (Kunkel, et al. 1985) supra.). The resulting B5(Fv)-SER $V_H$ 95 mutant molecule (designated B5(Fv): $V_H$ Y95S) showed 4-fold increase in specific binding activity as analyzed by cytotoxicity assays, from which the (relative) affinities can be deduced (Table 7). Thus, the VH tyrosine to serine 95 mutation not only increases the affinity of B3(Fv) but also of one other $Le^Y$ binding antibody and probably others. Since the mechanism by which the ser 95 causes increased affinity is most likely facilitation of induced fit binding, it is expected that this mutation can also increase the affinity of certain other antibodies, in cases where induced fit will generate increased interactions between the antibody and the antigen.

TABLE 7

Relative binding affinity of single chain fusion proteins with substitutions at $V_H$ position 95.

| Single Chain Antibody | Amino Acid at Position 95 of $V_H$ | Percentage Binding Affinity* |
|---|---|---|
| B3(Fv) | tyrosine | 10% |
| B3(Fv) | serine | 100% |
| B5(Fv) | tyrosine | 25% |
| B5(Fv) | serine | 100% |

*Best binding affinity was set to 100%.

What is claimed is:

1. A recombinant DNA molecule that encodes a single chain fusion protein, said recombinant DNA molecule comprising:
   a) a DNA sequence that encodes the Fv region of both the light and heavy chains of an antibody wherein said Fv region is selected from the group consisting of B3(Fv): $V_L$ M4L, B3(Fv): $V_L$ S7T and B3(Fv): $V_L$ M4L S7T; and
   b) a DNA sequence that encodes an effector molecule.

2. A recombinant DNA molecule that encodes a single chain antibody, said recombinant DNA molecule comprising a DNA sequence that encodes the Fv region of the heavy chain and a DNA sequence that encodes the Fv region of the light chain of an antibody; wherein said DNA sequences are recombinantly fused to form a single molecule and wherein said Fv region is selected from the group consisting of B3(Fv): $V_L$ M4L, B3(Fv): $V_L$ S7T and B3(Fv): $V_L$ M4L S7T.

3. A recombinantly produced single chain antibody comprising an Fv region of both a light and a heavy chain of an antibody where said Fv region is selected from the group consisting of B3(Fv): $V_L$ M4L, B3(Fv): $V_L$ S7T and B3(Fv): $V_L$ M4L S7T.

* * * * *

SEQUENCE LISTING (1) GENERAL INFORMATION:

(iii) NUMBER OF SEQUENCES: 68

(2) INFORMATION FOR SEQ ID NO:1:

(i) SEQUENCE CHARACTERISTICS:
      (A) LENGTH: 44 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1..44
      (D) OTHER INFORMATION: /note= "B3-H1 Heavy chain PCR primer"

(xi) SEQUENCE DESCRIPTION: SEQ ID NO:1:

TAACTAGGAT CCGTCCATAT GGATGTGAAG CTGGTGGAGT CTGG      44

(2) INFORMATION FOR SEQ ID NO:2:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1..39
      (D) OTHER INFORMATION: /note= "B3-H2 Heavy chain PCR primer"

(xi) SEQUENCE DESCRIPTION: SEQ ID NO:2:

TGGATAGACT GATGGGGATC CGCCTCCGCC TGAGGAGAC      39

(2) INFORMATION FOR SEQ ID NO:3:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (ii) MOLECULE TYPE: DNA (ix) FEATURE:

(A) NAME/KEY: -
        (B) LOCATION: 1..39
        (D) OTHER INFORMATION: /note= "B1HFr1 Heavy chain PCR primer"

(xi) SEQUENCE DESCRIPTION: SEQ ID NO:3:

GATATACATA TGGAGGTGCA GCTGGTGGAA TCTGGAGGA                                   39

(2) INFORMATION FOR SEQ ID NO:4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..39
        (D) OTHER INFORMATION: /note= "B5HFr1 Heavy chain PCR primer"

(xi) SEQUENCE DESCRIPTION: SEQ ID NO:4:

GATATACATA TGGAGGTGAA GCTGGTGGAA TCTGGAGGA                                   39

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..24
        (D) OTHER INFORMATION: /note= "GammaCH1 Heavy chain PCR
              primer"

(xi) SEQUENCE DESCRIPTION: SEQ ID NO:5:

AGCAGATCCA GGGGCCAGTG GATA                                                   24

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..27
        (D) OTHER INFORMATION: /note= "B1HFr4 Heavy chain PCR primer"

(xi) SEQUENCE DESCRIPTION: SEQ ID NO:6:

ACCGGATCCG CCTGCAGAGA CAGTGAC                                                27

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA -continued (ix) FEATURE:
    (A) NAME/KEY: -
    (B) LOCATION: 1..33
    (D) OTHER INFORMATION: /note= "B5HFr4 Heavy chain PCR primer"

(xi) SEQUENCE DESCRIPTION: SEQ ID NO:7:

ACCGGATCCG CCTCCGCCTG AGGAGACAGT GAS          33

(2) INFORMATION FOR SEQ ID NO:8:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..70
        (D) OTHER INFORMATION: /note= "B3-L1 Light chain PCR primer"

(xi) SEQUENCE DESCRIPTION: SEQ ID NO:8:

GTCTCCAAGC TTGGGGATCC GGTGGTGGCG GATCTGGAGG TGGCGGAAGC GATGTGCTGA          60

CCCAGTCTCC          70

(2) INFORMATION FOR SEQ ID NO:9:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..42
        (D) OTHER INFORMATION: /note= "B3-L2 Light chain PCR primer"

(xi) SEQUENCE DESCRIPTION: SEQ ID NO:9:

AGTTGGTGCA GCATCAAAAG CTTTTKAKYTC CAGCTTKGTS CC          42

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..28
        (D) OTHER INFORMATION: /note= "B3-L3 Light chain PCR primer"

(xi) SEQUENCE DESCRIPTION: SEQ ID NO:10:

TTGGGGATCC GGTGGTGGCG GATCTGGA          28

(2) INFORMATION FOR SEQ ID NO:11:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
    (A) NAME/KEY: -
    (B) LOCATION: 1..40
    (D) OTHER INFORMATION: /note= "B3-L4 Light chain PCR primer"

(xi) SEQUENCE DESCRIPTION: SEQ ID NO:11:

AGCGGGAATT CATTATTTAA TTTCCAGCTT TGTCCCCGAC                    40

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..30
        (D) OTHER INFORMATION: /note= "B1LFr1 Light chain PCR primer"

(xi) SEQUENCE DESCRIPTION: SEQ ID NO:12:

GGTGGCGGAA GCGATGTTGT GATGACCCAA                              30

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..30
        (D) OTHER INFORMATION: /note= "B5LFr1 Light chain PCR primer"

(xi) SEQUENCE DESCRIPTION: SEQ ID NO:13:

GGTGGCGGAA GCGATGTTTT GTTGACCCAA                              30

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..24
        (D) OTHER INFORMATION: /note= "C-kappa Light chain PCR primer"

(xi) SEQUENCE DESCRIPTION: SEQ ID NO:14:

TGGTGGGAAG ATGGATACAG TTGG                                    24

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear

```
         (ii) MOLECULE TYPE: DNA (ix) FEATURE:
              (A) NAME/KEY: -
              (B) LOCATION: 1..24
              (D) OTHER INFORMATION: /note= "B1LFr4 Light chain PCR primer"

(xi) SEQUENCE DESCRIPTION: SEQ ID NO:15:

GGAAGCTTTC AGCTCCAGCT TGGT                                             24

(2) INFORMATION FOR SEQ ID NO:16:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1..23
              (D) OTHER INFORMATION: /note= "B5LFr4 Light chain PCR primer"

(xi) SEQUENCE DESCRIPTION: SEQ ID NO:16:

GGAAGCTTTA TTTCCAACTT TGT                                              23

(2) INFORMATION FOR SEQ ID NO:17:

(i) SEQUENCE CHARACTERISTICS:
              (A) LENGTH: 357 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1..357
              (D) OTHER INFORMATION: /note= "B3 Variable Heavy chain (V-H)"

(xi) SEQUENCE DESCRIPTION: SEQ ID NO:17:

GATGTGAAGC TGGTGGAGTC TGGGGGAGGC TTAGTGCAGC CTGGAGGGTC CCTGAAACTC       60

TCCTGTGCAA CCTCTGGATT CACTTTCAGT GACTATTACA TGTATTGGGT TCGCCAGACT      120

CCAGAGAAGA GGCTGGAGTG GGTCGCATAC ATTAGTAATG ATGATAGTTC CGCCGCTTAT      180

TCAGACACTG TAAAGGGCCG GTTCACCATC TCCAGAGACA ATGCCAGGAA CACCCTCTAC      240

CTGCAAATGA GCCGTCTGAA GTCTGAGGAC ACAGCCATAT ATTCCTGTGC AAGAGGACTG      300

GCCTGGGGAG CCTGGTTTGC TTACTGGGGC CAAGGGACTC TGGTCACTGT CTCCTCA        357

(2) INFORMATION FOR SEQ ID NO:18:

(i) SEQUENCE CHARACTERISTICS:
              (A) LENGTH: 336 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1..336
              (D) OTHER INFORMATION: /note= "B3 Variable Light chain (V-L)"
```

(xi) SEQUENCE DESCRIPTION: SEQ ID NO:18:

```
GATGTGCTGA TGACCCAGTC TCCATTGAGT TTACCTGTCA GTCTTGGAGA TCAAGCCTCC        60
ATCTCTTGCA GATCTAGTCA GATCATTGTA CATAGTAATG GAAACACCTA TTTAGAATGG       120
TACCTGCAGA AACCAGGCCA GTCTCCAAAG CTCCTGATCT ACAAAGTTTC CAACCGATTT       180
TCTGGGGTCC CAGACAGGTT CAGTGGCAGT GGATCAGGGA CAGATTTCAC ACTCAAGATC       240
AGCAGAGTGG AGGCTGAGGA TCTGGGAGTT TATTACTGCT TTCAAGGTTC ACATGTTCCA       300
TTCACGTTCG GCTCGGGGAC AAAGCTGGAA ATTAAA                                 336
```

(2) INFORMATION FOR SEQ ID NO:19:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..363
        (D) OTHER INFORMATION: /note= "B1 Variable Heavy chain (V-H)"

(xi) SEQUENCE DESCRIPTION: SEQ ID NO:19:

```
GAGGTGCAGC TGGTGGAATC TGGAGGAGGC TTAGTGAAGC CTGGAGGGTC CCTGAAACTC        60
TCCTGTGCAG CCTCTGGATT CATTTTCAGT GACAATTACA TGTATTGGGT TCGCCAGACT       120
CCGGAGAAGA GGCTGGAGTG GGTCGCAACC ATTAGTGATG GTGGCACTTA TATCGACTAT       180
TCAGACAGTG TGAAGGGGCG ATTCACCATC TCCAGAGACA ATGCCAAGAA TAATCTGTAC       240
TTGCAAATGA GCAGTCTGAG GTCTGAGGAC ACAGGCATGT ATTATTGTGG AAGGAGTCCG       300
ATCTACTATG ATTACGCCCC GTTTACTTAC TGGGGCCAAG GGACTCTGGT CACTGTCTCT       360
GCA                                                                    363
```

(2) INFORMATION FOR SEQ ID NO:20:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..336
        (D) OTHER INFORMATION: /note= "B1 Variable Light chain (V-L)"

(xi) SEQUENCE DESCRIPTION: SEQ ID NO:20:

```
GATGTTGTGA TGACCCAGAC TCCACTCTCC CTGCCTGTCA GTCTTGGAGA TCAAGCCTCC        60
ATCTCTTGCA GATCTAGTCA AAACCTTGTA CACAGTGATG GAAAAACCTA TTTACATTGG       120
TTCCTGCAGA AGCCTGGCCA GTCTCCAACG CTCCTGATCT ACAAAGTTTC CAACCGATTT       180
TCTGGGGTCC CAGACAGGTT CAGTGGCAGT GGATCAGGGA CAGATTTCAT ACTCAAGATC       240
AGCAGAGTGG AGGCTGAGGA TCTGGGAGTT TATTTCTGCT CTCAAAGTAC ACATGTTCCG       300
CTCACGTTCG GTGCTGGGAC CAAGCTGGAG CTGAAA                                 336
```

(2) INFORMATION FOR SEQ ID NO:21:

(i) SEQUENCE CHARACTERISTICS:

```
            (A) LENGTH: 357 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..357
            (D) OTHER INFORMATION: /note= "B5 Variable Heavy chain (V-H)"

(xi) SEQUENCE DESCRIPTION: SEQ ID NO:21:

GAGGTGAAGC TGGTGGAATC TGGAGGAGGC TTAGTGCAGC CTGGAGGGTC CCTGAAACTC      60

TCCTGTGCAA CCTCTGGATT TACTTTCAGT GACTATTACA TGTATTGGGT TCGCCAGACT     120

CCAGAGAAGA GGCTGGAGTG GGTCGCATAC ATTAGTAATG GTGGTGGTAG CACCTATTAT     180

CCAGACACTG TAAAGGGCCG ATTCACCATC TCCAGAGACA ACGCCAAGAA CACCCTGTAC     240

CTGCAGATGA GCCGTCTGAA GTCTGAGGAC ACAGCCATGT ATTACTGTGC AAGGGGGCTC     300

TCTGATGGTT CCTGGTTTGC TTACTGGGGC CAAGGGACTC TGGTCACTGT CTCCTCA       357

(2) INFORMATION FOR SEQ ID NO:22:

(i) SEQUENCE CHARACTERISTICS:
            (A) LENGTH: 336 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..336
            (D) OTHER INFORMATION: /note= "B5 Variable Light chain (V-L)"

(xi) SEQUENCE DESCRIPTION: SEQ ID NO:22:

GATGTTTTGT TGACCCAAAC TCCACTCTCC CTGCCTGTCA GTCTTGGAGA TCAAGCCTCT      60

ATTTCTTGTA GATCTAGTCA GAGCATTGTA CATAGTAATG GAAACACCTA TTTAGAATGG     120

TACCTGCAGA AACCAGGCCA GTCTCCAAAG CTCCTGATCT ACAAAGTTTC CAACCGATTT     180

TCTGGGGTCC CAGACAGGTT CAGTGGCAGT GGATCAGGGA CAGATTTCAC ACTCAAGATC     240

AGCAGAGTGG AGGCTGAGGA TCTGGGAGTT TATTACTGCT TTCAAGGTTC ACATGTTCCA     300

TTCACGTTCG GCTCGGGGAC AAAGTTGGAA ATTAAA                              336

(2) INFORMATION FOR SEQ ID NO:23:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..42
            (D) OTHER INFORMATION: /note= "Primer 1 for B3 Variable
                Heavy chain (V-H) site-directed
                mutagenesis of L11V; G16R"

(xi) SEQUENCE DESCRIPTION: SEQ ID NO:23:

GGAGAGTTTC AGGGAGCGCC CGGGGTGCAC GACGCCTCCC CC                         42
```

(2) INFORMATION FOR SEQ ID NO:24:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..45
        (D) OTHER INFORMATION: /note= "Primer 2 for B3 Variable
            Heavy chain (V-H) site-directed
            mutagenesis of T40A; E42G; R44G"

(xi) SEQUENCE DESCRIPTION: SEQ ID NO:24:

TGCGACCCAC TCCAGGCCCT TGCCCGGGGC CTGGCGAACC CAATA                45

(2) INFORMATION FOR SEQ ID NO:25:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..39
        (D) OTHER INFORMATION: /note= "Primer 3 for B3 Variable
            Heavy chain (V-H) site-directed
            mutagenesis of A74S; R75K"

(xi) SEQUENCE DESCRIPTION: SEQ ID NO:25:

GAGGGTGTTC TTGCTATTGT CTCTAGAGAT GGTGAACCG                       39

(2) INFORMATION FOR SEQ ID NO:26:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..42
        (D) OTHER INFORMATION: /note= "Primer 4 for B3 Variable
            Heavy chain (V-H) site-directed
            mutagenesis of S82aN; R82bS; K83R;
            S84A"

(xi) SEQUENCE DESCRIPTION: SEQ ID NO:26:

TATGGCTGTG TCCTCGGCGC GCAGGCTGTT CATTTGCAGG TA                   42

(2) INFORMATION FOR SEQ ID NO:27:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..45

5,981,726

(D) OTHER INFORMATION: /note= "Primer 5 for B3 Variable
            Light chain (V-L) site-directed
            mutagenesis of S14T; L15P; D17E; Q18P"

(xi) SEQUENCE DESCRIPTION: SEQ ID NO:27:

GCAAGAGATG GAGGCCGGCT CTCCCGGGGT GACAGGTAAA CTCAA                45

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..36
        (D) OTHER INFORMATION: /note= "Primer 6 for B3 Variable
            Light chain (V-L) site-directed
            mutagenesis of K45Q"

(xi) SEQUENCE DESCRIPTION: SEQ ID NO:28:

AACTTTGTAG ATCAGCAGCT GTGGAGACTG GGCTGG                          36

(2) INFORMATION FOR SEQ ID NO:29:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..33
        (D) OTHER INFORMATION: /note= "Primer 7 for B3 Variable
            Light chain (V-L) site-directed
            mutagenesis of L83V"

(xi) SEQUENCE DESCRIPTION: SEQ ID NO:29:

GCAGTAATAA ACTCCGACGT CCTCAGCCTC CAC                             33

(2) INFORMATION FOR SEQ ID NO:30:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..45
        (D) OTHER INFORMATION: /note= "Primer 8 for B3 Variable
            Light chain (V-L) site-directed
            mutagenesis of S100Q; L104V"

(xi) SEQUENCE DESCRIPTION: SEQ ID NO:30:

GGAAGCTTTA ATTTCGACCT TGGTACCCTG GCCGAACGTG AATGG                45

(2) INFORMATION FOR SEQ ID NO:31:

(i) SEQUENCE CHARACTERISTICS:
        (A) LENGTH: 738 base pairs
        (B) TYPE: nucleic acid -continued

```
        (C) STRANDEDNESS: single
        (D) TOPOLOGY: linear (ii) MOLECULE TYPE: DNA (ix) FEATURE:
        (A) NAME/KEY: -
        (B) LOCATION: 1..738
        (D) OTHER INFORMATION: /note= "Humanized B3 single-chain Fv"

(xi) SEQUENCE DESCRIPTION: SEQ ID NO:31:

GATGTGAAGC TGGTGGAGTC TGGGGGAGGC GTCGTGCAGC CCGGGCGCTC CCTGAAACTC    60

TCCTGTGCAA CCTCTGGATT CACTTTCAGT GACTATTACA TGTATTGGGT TCGCCAGGCC   120

CCGGGCAAGG GCCTGGAGTG GGTCGCATAC ATTAGTAATG ATGATAGTTC CGCCGCTTAT   180

TCAGACACTG TAAAGGGCCG GTTCACCATC TCTAGAGACA ATAGCAAGAA CACCCTCTAC   240

CTGCAAATGA ACCGTCTGCG CGCCGAGGAC ACAGCCATAT ATTCCTGTGC AAGAGGACTG   300

GCCTGGGGAG CCTGGTTTGC TTACTGGGGC CAAGGGACTC TGGTCACTGT CTCCTCAGGC   360

GGAGGCGGAT CCGGTGGTGG CGGATCTGGA GGTGGCGGAA GCGATGTGCT GATGACCCAG   420

TCTCCATTGA GTTTACCTGT CACCCCGGGA GAGCCGGCCT CCATCTCTTG CAGATCTAGT   480

CAGATCATTG TACATAGTAA TGGAAACACC TATTTAGAAT GGTACCTGCA GAAACCAGGC   540

CAGTCTCCAC AGCTGCTGAT CTACAAAGTT TCCAACCGAT TTTCTGGGGT CCCAGACAGG   600

TTCAGTGGCA GTGGATCAGG GACAGATTTC ACACTCAAGA TCAGCAGAGT GGAGGCTGAG   660

GACGTCGGAG TTTATTACTG CTTTCAAGGT TCACATGTTC CATTCACGTT CGGCCAGGGT   720

ACCAAGGTCG AAATTAAA                                                 738

(2) INFORMATION FOR SEQ ID NO:32:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

Gly Gly Gly Gly Ser Gly Gly Gly Gly Ser Gly Gly Gly Gly Ser
1               5                   10                  15

(2) INFORMATION FOR SEQ ID NO:33:

(i) SEQUENCE CHARACTERISTICS:
        (A) LENGTH: 772 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..772
        (D) OTHER INFORMATION: /note= "Single-chain antibody fusion
            protein of B3 monoclonal antibody
            Variable Heavy chain (V-H) and
            Variable Light chain (V-L) Fv region
            joined by a (Gly-4Ser)-3 peptide linker"

(ix) FEATURE:
        (A) NAME/KEY: CDS
        (B) LOCATION: 27..770

(xi) SEQUENCE DESCRIPTION: SEQ ID NO:33:
```

```
TTTAACTTTA AGAAGGAGAT ATACAT ATG GAT GTG AAG CTG GTG GAG TCT GGG          53
                            Met Asp Val Lys Leu Val Glu Ser Gly
                             1               5

GGA GGC TTA GTG CAG CCT GGA GGG TCC CTG AAA CTC TCC TGT GCA ACC         101
Gly Gly Leu Val Gln Pro Gly Gly Ser Leu Lys Leu Ser Cys Ala Thr
 10              15                  20                  25

TCT GGA TTC ACT TTC AGT GAC TAT TAC ATG TAT TGG GTT CGC CAG ACT         149
Ser Gly Phe Thr Phe Ser Asp Tyr Tyr Met Tyr Trp Val Arg Gln Thr
             30                  35                  40

CCA GAG AAG AGG CTG GAG TGG GTC GCA TAC ATT AGT AAT GAT GAT AGT         197
Pro Glu Lys Arg Leu Glu Trp Val Ala Tyr Ile Ser Asn Asp Asp Ser
         45                  50                  55

TCC GCC GCT TAT TCA GAC ACT GTA AAG GGC CGG TTC ACC ATC TCC AGA         245
Ser Ala Ala Tyr Ser Asp Thr Val Lys Gly Arg Phe Thr Ile Ser Arg
     60                  65                  70

GAC AAT GCC AGG AAC ACC CTC TAC CTG CAA ATG AGC CGT CTG AAG TCT         293
Asp Asn Ala Arg Asn Thr Leu Tyr Leu Gln Met Ser Arg Leu Lys Ser
 75                  80                  85

GAG GAC ACA GCC ATA TAT TCC TGT GCA AGA GGA CTG GCC TGG GGA GCC         341
Glu Asp Thr Ala Ile Tyr Ser Cys Ala Arg Gly Leu Ala Trp Gly Ala
 90                  95                 100                 105

TGG TTT GCT TAC TGG GGC CAA GGG ACT CTG GTC ACT GTC TCC TCA GGC         389
Trp Phe Ala Tyr Trp Gly Gln Gly Thr Leu Val Thr Val Ser Ser Gly
                 110                 115                 120

GGA GGC GGA TCC GGT GGT GGC GGA TCT GGA GGT GGC GGA AGC GAT GTG         437
Gly Gly Gly Ser Gly Gly Gly Gly Ser Gly Gly Gly Gly Ser Asp Val
             125                 130                 135

CTG ATG ACC CAG TCT CCA TTG AGT TTA CCT GTC AGT CTT GGA GAT CAA         485
Leu Met Thr Gln Ser Pro Leu Ser Leu Pro Val Ser Leu Gly Asp Gln
         140                 145                 150

GCC TCC ATC TCT TGC AGA TCT AGT CAG ATC ATT GTA CAT AGT AAT GGA         533
Ala Ser Ile Ser Cys Arg Ser Ser Gln Ile Ile Val His Ser Asn Gly
     155                 160                 165

AAC ACC TAT TTA GAA TGG TAC CTG CAG AAA CCA GGC CAG TCT CCA AAG         581
Asn Thr Tyr Leu Glu Trp Tyr Leu Gln Lys Pro Gly Gln Ser Pro Lys
170                 175                 180                 185

CTC CTG ATC TAC AAA GTT TCC AAC CGA TTT TCT GGG GTC CCA GAC AGG         629
Leu Leu Ile Tyr Lys Val Ser Asn Arg Phe Ser Gly Val Pro Asp Arg
                 190                 195                 200

TTC AGT GGC AGT GGA TCA GGG ACA GAT TTC ACA CTC AAG ATC AGC AGA         677
Phe Ser Gly Ser Gly Ser Gly Thr Asp Phe Thr Leu Lys Ile Ser Arg
             205                 210                 215

GTG GAG GCT GAG GAT CTG GGA GTT TAT TAC TGC TTT CAA GGT TCA CAT         725
Val Glu Ala Glu Asp Leu Gly Val Tyr Tyr Cys Phe Gln Gly Ser His
         220                 225                 230

GTT CCA TTC ACG TTC GGC TCG GGG ACA AAG CTG GAA ATT AAA GCT             770
Val Pro Phe Thr Phe Gly Ser Gly Thr Lys Leu Glu Ile Lys Ala
     235                 240                 245

TT                                                                      772

(2) INFORMATION FOR SEQ ID NO:34:

(i) SEQUENCE CHARACTERISTICS:
        (A) LENGTH: 248 amino acids
        (B) TYPE: amino acid
        (D) TOPOLOGY: linear (ii) MOLECULE TYPE: protein
```

(xi) SEQUENCE DESCRIPTION: SEQ ID NO:34:

Met Asp Val Lys Leu Val Glu Ser Gly Gly Gly Leu Val Gln Pro Gly
1               5                   10                  15

Gly Ser Leu Lys Leu Ser Cys Ala Thr Ser Gly Phe Thr Phe Ser Asp
            20                  25                  30

Tyr Tyr Met Tyr Trp Val Arg Gln Thr Pro Glu Lys Arg Leu Glu Trp
        35                  40                  45

Val Ala Tyr Ile Ser Asn Asp Asp Ser Ser Ala Ala Tyr Ser Asp Thr
    50                  55                  60

Val Lys Gly Arg Phe Thr Ile Ser Arg Asp Asn Ala Arg Asn Thr Leu
65                  70                  75                  80

Tyr Leu Gln Met Ser Arg Leu Lys Ser Glu Asp Thr Ala Ile Tyr Ser
                85                  90                  95

Cys Ala Arg Gly Leu Ala Trp Gly Ala Trp Phe Ala Tyr Trp Gly Gln
            100                 105                 110

Gly Thr Leu Val Thr Val Ser Ser Gly Gly Gly Ser Gly Gly Gly
            115                 120                 125

Gly Ser Gly Gly Gly Ser Asp Val Leu Met Thr Gln Ser Pro Leu
    130                 135                 140

Ser Leu Pro Val Ser Leu Gly Asp Gln Ala Ser Ile Ser Cys Arg Ser
145                 150                 155                 160

Ser Gln Ile Ile Val His Ser Asn Gly Asn Thr Tyr Leu Glu Trp Tyr
                165                 170                 175

Leu Gln Lys Pro Gly Gln Ser Pro Lys Leu Leu Ile Tyr Lys Val Ser
            180                 185                 190

Asn Arg Phe Ser Gly Val Pro Asp Arg Phe Ser Gly Ser Gly Ser Gly
            195                 200                 205

Thr Asp Phe Thr Leu Lys Ile Ser Arg Val Glu Ala Glu Asp Leu Gly
    210                 215                 220

Val Tyr Tyr Cys Phe Gln Gly Ser His Val Pro Phe Thr Phe Gly Ser
225                 230                 235                 240

Gly Thr Lys Leu Glu Ile Lys Ala
                245

(2) INFORMATION FOR SEQ ID NO:35:

(i) SEQUENCE CHARACTERISTICS:
  (A) LENGTH: 58 base pairs
  (B) TYPE: nucleic acid
  (C) STRANDEDNESS: single
  (D) TOPOLOGY: linear (ii) MOLECULE TYPE: DNA (ix) FEATURE:
  (A) NAME/KEY: -
  (B) LOCATION: 1..58
  (D) OTHER INFORMATION: /note= "3' Variable Light chain (V-L)
   sequence from nucleotides 721-779 for
   expression of single-chain B3(Fv) alone"

(ix) FEATURE:
  (A) NAME/KEY: CDS
  (B) LOCATION: 3..47

(xi) SEQUENCE DESCRIPTION: SEQ ID NO:35:

CA CAT GTT CCA TTC ACG TTC GGC TCG GGG ACA AAG CTG GAA ATT AAA 47
 His Val Pro Phe Thr Phe Gly Ser Gly Thr Lys Leu Glu Ile Lys
   250     255     260

TAATGAATTC C 58

(2) INFORMATION FOR SEQ ID NO:36:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:36:

```
His Val Pro Phe Thr Phe Gly Ser Gly Thr Lys Leu Glu Ile Lys
 1               5                  10                  15
```

(2) INFORMATION FOR SEQ ID NO:37:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

CTCTCCCTG                                                                                                                             9

(2) INFORMATION FOR SEQ ID NO:38:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

TTGAGTTTA                                                                                                                             9

(2) INFORMATION FOR SEQ ID NO:39:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

CCAGTCTCCA CTCTCC                                                                                 16

(2) INFORMATION FOR SEQ ID NO:40:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:40:

```
Met Glu Val Gln Leu Val Glu Ser Gly Gly
 1               5                  10
```

(2) INFORMATION FOR SEQ ID NO:41:

(i) SEQUENCE CHARACTERISTICS:

-continued (A) LENGTH: 10 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:41:

Met Glu Val Lys Leu Val Glu Ser Gly Gly
1 5 10

(2) INFORMATION FOR SEQ ID NO:42:

(i) SEQUENCE CHARACTERISTICS:
(A) LENGTH: 10 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:42:

Gly Gly Gly Ser Asp Val Val Met Thr Gln
1 5 10

(2) INFORMATION FOR SEQ ID NO:43:

(i) SEQUENCE CHARACTERISTICS:
(A) LENGTH: 10 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:43:

Gly Gly Gly Ser Asp Val Leu Leu Thr Gln
1 5 10

(2) INFORMATION FOR SEQ ID NO:44:

(i) SEQUENCE CHARACTERISTICS:
(A) LENGTH: 8 amino acids
(B) TYPE: amino acid
(C) STRANDEDNESS:
(D) TOPOLOGY: linear (ii) MOLECULE TYPE: peptide (ix) FEATURE:
(A) NAME/KEY: Peptide
(B) LOCATION: 1..8
(D) OTHER INFORMATION: /note= "C3 connector between Fv region and PE38 cytotoxin effector molecule"

(xi) SEQUENCE DESCRIPTION: SEQ ID NO:44:

Ser Gly Gly Pro Glu Gly Gly Ser
1 5

(2) INFORMATION FOR SEQ ID NO:45:

(i) SEQUENCE CHARACTERISTICS:
(A) LENGTH: 119 amino acids
(B) TYPE: amino acid
(C) STRANDEDNESS:
(D) TOPOLOGY: linear (ii) MOLECULE TYPE: protein (ix) FEATURE:
(A) NAME/KEY: Protein
(B) LOCATION: 1..119

(D) OTHER INFORMATION: /note= "Mouse monoclonal antibody B3
    Variable Heavy chain (V-H)"

(xi) SEQUENCE DESCRIPTION: SEQ ID NO:45:

Asp Val Lys Leu Val Glu Ser Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Asp Ser Ser Ala Ala Tyr Ser Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Arg Leu Lys Ser Glu Asp Thr Ala Ile Tyr Ser Cys
            85                  90                  95

Ala Arg Gly Leu Ala Trp Gly Ala Trp Phe Ala Tyr Trp Gly Gln Gly
            100                 105                 110

Thr Leu Val Thr Val Ser Ser
            115

(2) INFORMATION FOR SEQ ID NO:46:

(i) SEQUENCE CHARACTERISTICS:
        (A) LENGTH: 119 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..119
        (D) OTHER INFORMATION: /note= "Human fetal immunoglobulin
            56P1'CL Variable Heavy chain (V-H)"

(xi) SEQUENCE DESCRIPTION: SEQ ID NO:46:

Gln Val Glu Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Arg Ser Ala Arg Thr Tyr Tyr Phe Asp Tyr Trp Gly Gln Gly
            100                 105                 110

Thr Leu Val Thr Val Ser Ser
            115

(2) INFORMATION FOR SEQ ID NO:47:

(i) SEQUENCE CHARACTERISTICS:
        (A) LENGTH: 119 amino acids
        (B) TYPE: amino acid (C) STRANDEDNESS:
        (D) TOPOLOGY: linear (ii) MOLECULE TYPE: protein (ix) FEATURE:
        (A) NAME/KEY: Protein
        (B) LOCATION: 1..119
        (D) OTHER INFORMATION: /note= "Humanized B3 Variable Heavy
            chain (V-H) (HumB3V-H)"

(xi) SEQUENCE DESCRIPTION: SEQ ID NO:47:

Asp Val Lys Leu Val Glu Ser Gly Gly Gly Val Val Gln Pro Gly Arg
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Tyr Ile Ser Asn Asp Ser Ser Ala Ala Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Ile Tyr Ser Cys
                85                  90                  95

Ala Arg Gly Leu Ala Trp Gly Ala Trp Phe Ala Tyr Trp Gly Gln Gly
            100                 105                 110

Thr Leu Val Thr Val Ser Ser
            115

(2) INFORMATION FOR SEQ ID NO:48:

(i) SEQUENCE CHARACTERISTICS:
        (A) LENGTH: 112 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..112
        (D) OTHER INFORMATION: /note= "Mouse monoclonal antibody B3
            Variable Light chain (V-L)"

(xi) SEQUENCE DESCRIPTION: SEQ ID NO:48:

Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Ile Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

(2) INFORMATION FOR SEQ ID NO:49:

(i) SEQUENCE CHARACTERISTICS:
       (A) LENGTH: 112 amino acids
       (B) TYPE: amino acid
       (C) STRANDEDNESS:
       (D) TOPOLOGY: linear (ii) MOLECULE TYPE: protein (ix) FEATURE:
       (A) NAME/KEY: Protein
       (B) LOCATION: 1..112
       (D) OTHER INFORMATION: /note= "Human IgM antibody GM607
           Variable Light chain (V-L)"

(xi) SEQUENCE DESCRIPTION: SEQ ID NO:49:

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gln Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Thr Pro Gln Thr Phe Gly Gln Gly Thr Lys Val Glu Ile Lys
            100                 105                 110

(2) INFORMATION FOR SEQ ID NO:50:

(i) SEQUENCE CHARACTERISTICS:
       (A) LENGTH: 112 amino acids
       (B) TYPE: amino acid
       (C) STRANDEDNESS:
       (D) TOPOLOGY: linear (ii) MOLECULE TYPE: protein (ix) FEATURE:
       (A) NAME/KEY: Protein
       (B) LOCATION: 1..112
       (D) OTHER INFORMATION: /note= "Humanized B3 Variable Light
           chain (V-L) (HumB3V-L)"

(xi) SEQUENCE DESCRIPTION: SEQ ID NO:50:

Asp Val Leu Met Thr Gln Ser Pro Leu Ser Leu Pro Val Thr Pro Gly
1               5                   10                  15

Glu Pro Ala Ser Ile Ser Cys Arg Ser Ser Gln Ile Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Val Glu Ile Lys
            100                 105                 110

(2) INFORMATION FOR SEQ ID NO:51:

(i) SEQUENCE CHARACTERISTICS:
    (A) LENGTH: 4 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:51:

Lys Asp Glu Leu
1

(2) INFORMATION FOR SEQ ID NO:52:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:52:

Arg Glu Asp Leu
1

(2) INFORMATION FOR SEQ ID NO:53:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:53:

Arg Glu Asp Leu Lys
1               5

(2) INFORMATION FOR SEQ ID NO:54:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:54:

Ser Gly Gly Gly Gly Ser Gly Gly Gly Gly Ser Gly Gly Gly Gly Ser
1               5                   10                  15

(2) INFORMATION FOR SEQ ID NO:55:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:55:

Glu Val Lys Leu Val Glu Ser Gly Gly Gly Leu Val Gln Pro Gly Gly
1               5                   10                  15

Ser Leu (2) INFORMATION FOR SEQ ID NO:56:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 17
        (D) OTHER INFORMATION: /product= "OTHER"
            /note= "Xaa = unsure"

(xi) SEQUENCE DESCRIPTION: SEQ ID NO:56:

```
Asp Val Leu Met Thr Gln Ser Pro Leu Ser Leu Pro Val Ser Leu Gly
 1               5                  10                  15

Xaa Gln
```

(2) INFORMATION FOR SEQ ID NO:57:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..411
        (D) OTHER INFORMATION: /note= "Mouse monoclonal antibody B1 Fv
            Heavy chain region"

(xi) SEQUENCE DESCRIPTION: SEQ ID NO:57:

```
GAGGTGCAGC TGGTGGAATC TGGAGGAGGC TTAGTGAAGC CTGGAGGGTC CCTGAAACTC    60

TCCTGTGCAG CCTCTGGATT CATTTTCAGT GACAATTACA TGTATTGGGT TCGCCAGACT   120

CCGGAGAAGA GGCTGGAGTG GGTCGCAACC ATTAGTGATG GTGGCACTTA TATCGACTAT   180

TCAGACAGTG TGAAGGGGCG ATTCACCATC TCCAGAGACA ATGCCAAGAA TAATCTGTAC   240

TTGCAAATGA GCAGTCTGAG GTCTGAGGAC ACAGGCATGT ATTATTGTGG AAGGAGTCCG   300

ATCTACTATG ATTACGCCCC GTTTACTTAC TGGGGCCAAG GGACTCTGGT CACTGTCTCT   360

GCAGCCAAAA CGACACCCCC ATCTGTCTAT CCACTGGCCC CTGGATCTGC T           411
```

(2) INFORMATION FOR SEQ ID NO:58:

(i) SEQUENCE CHARACTERISTICS:
        (A) LENGTH: 375 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..375
        (D) OTHER INFORMATION: /note= "Mouse monoclonal antibody B1 Fv
            Light chain region"

(xi) SEQUENCE DESCRIPTION: SEQ ID NO:58:

```
GATGTTGTGA TGACCCAGAC TCCACTCTCC CTGCCTGTCA GTCTTGGAGA TCAAGCCTCC    60

ATCTCTTGCA GATCTAGTCA AAACCTTGTA CACAGTGATG GAAAAACCTA TTTACATTGG   120
```

| | |
|---|---|
| TTCCTGCAGA AGCCTGGCCA GTCTCCAACG CTCCTGATCT ACAAAGTTTC CAACCGATTT | 180 |
| TCTGGGGTCC CAGACAGGTT CAGTGGCAGT GGATCAGGGA CAGATTTCAT ACTCAAGATC | 240 |
| AGCAGAGTGG AGGCTGAGGA TCTGGGAGTT TATTTCTGCT CTCAAAGTAC ACATGTTCCG | 300 |
| CTCACGTTCG GTGCTGGGAC CAAGCTGGAG CTGAAACGGG CTGATGCTGC ACCAACTGTA | 360 |
| TCCATCTTCC CACCA | 375 |

(2) INFORMATION FOR SEQ ID NO:59:

(i) SEQUENCE CHARACTERISTICS:
        (A) LENGTH: 375 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..375
        (D) OTHER INFORMATION: /note= "Mouse monoclonal antibody B5 Fv
            Heavy chain region"

(xi) SEQUENCE DESCRIPTION: SEQ ID NO:59:

| | |
|---|---|
| GAGGTGAAGC TGGTGGAATC TGGAGGAGGC TTAGTGCAGC CTGGAGGGTC CCTGAAACTC | 60 |
| TCCTGTGCAA CCTCTGGATT TACTTTCAGT GACTATTACA TGTATTGGGT TCGCCAGACT | 120 |
| CCAGAGAAGA GGCTGGAGTG GGTCGCATAC ATTAGTAATG GTGGTGGTAG CACCTATTAT | 180 |
| CCAGACACTG TAAAGGGCCG ATTCACCATC TCCAGAGACA ACGCCAAGAA CACCCTGTAC | 240 |
| CTGCAGATGA GCCGTCTGAA GTCTGAGGAC ACAGCCATGT ATTACTGTGC AAGGGGGCTC | 300 |
| TCTGATGGTT CCTGGTTTGC TTACTGGGGC CAAGGGACTC TGGTCACTGT CTCCTCAGGC | 360 |
| GGAGGCGGAT CCGGT | 375 |

(2) INFORMATION FOR SEQ ID NO:60:

(i) SEQUENCE CHARACTERISTICS:
        (A) LENGTH: 375 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..375
        (D) OTHER INFORMATION: /note= "Mouse monoclonal antibody B5 Fv
            Light chain region"

(xi) SEQUENCE DESCRIPTION: SEQ ID NO:60:

| | |
|---|---|
| GATGTTTTGT TGACCCAAAC TCCACTCTCC CTGCCTGTCA GTCTTGGAGA TCAAGCCTCT | 60 |
| ATTTCTTGTA GATCTAGTCA GAGCATTGTA CATAGTAATG GAAACACCTA TTTAGAATGG | 120 |
| TACCTGCAGA AACCAGGCCA GTCTCCAAAG CTCCTGATCT ACAAAGTTTC CAACCGATTT | 180 |
| TCTGGGGTCC CAGACAGGTT CAGTGGCAGT GGATCAGGGA CAGATTTCAC ACTCAAGATC | 240 |
| AGCAGAGTGG AGGCTGAGGA TCTGGGAGTT TATTACTGCT TTCAAGGTTC ACATGTTCCA | 300 |
| TTCACGTTCG GCTCGGGGAC AAAGTTGGAA ATTAAACGGG CTGATGCTGC ACCAACTGTA | 360 |
| TCCATCTTCC CACCA | 375 |

(2) INFORMATION FOR SEQ ID NO:61:

(i) SEQUENCE CHARACTERISTICS:

(A) LENGTH: 137 amino acids
    (B) TYPE: amino acid
    (C) STRANDEDNESS:
    (D) TOPOLOGY: linear (ii) MOLECULE TYPE: protein (ix) FEATURE:
    (A) NAME/KEY: Region
    (B) LOCATION: 1..137
    (D) OTHER INFORMATION: /note= "Mouse monoclonal antibody B1 Fv
        Heavy chain region"

(xi) SEQUENCE DESCRIPTION: SEQ ID NO:61:

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ile Phe Ser Asp Asn
            20                  25                  30

Tyr Met Tyr Trp Val Arg Gln Thr Pro Glu Lys Arg Leu Glu Trp Val
        35                  40                  45

Ala Thr Ile Ser Asp Gly Gly Thr Tyr Ile Asp Tyr Ser Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Gly Met Tyr Tyr Cys
                85                  90                  95

Gly Arg Ser Pro Ile Tyr Tyr Asp Tyr Ala Pro Phe Thr Tyr Trp Gly
            100                 105                 110

Gln Gly Thr Leu Val Thr Val Ser Ala Ala Lys Thr Thr Pro Pro Ser
        115                 120                 125

Val Tyr Pro Leu Ala Pro Gly Ser Ala
130                 135

(2) INFORMATION FOR SEQ ID NO:62:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:62:

Glu Val Gln Leu Val Glu Ser Gly Gly Gly Leu Val Lys Pro Gly Gly
1               5                   10                  15

Ser Leu (2) INFORMATION FOR SEQ ID NO:63:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Region
        (B) LOCATION: 1..125
        (D) OTHER INFORMATION: /note= "Mouse monoclonal antibody B1 Fv
            Light chain region"

(xi) SEQUENCE DESCRIPTION: SEQ ID NO:63:

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Asn Leu Val His Ser
            20                  25                  30

Asp Gly Lys Thr Tyr Leu His Trp Phe Leu Gln Lys Pro Gly Gln Ser
        35                  40                  45

Pro Thr Leu Leu Ile Tyr Lys Val Ser Asn Arg Phe Ser Gly Val Pro
    50                  55                  60

Asp Arg Phe Ser Gly Ser Gly Ser Gly Thr Asp Phe Ile Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
                100                 105                 110

Arg Ala Asp Ala Ala Pro Thr Val Ser Ile Phe Pro Pro
            115                 120                 125

(2) INFORMATION FOR SEQ ID NO:64:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:64:

Asp Val Val Met Thr Gln Thr Pro Leu Ser Leu Pro Val Ser Leu Gly
1               5                   10                  15

Asp (2) INFORMATION FOR SEQ ID NO:65:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Region
        (B) LOCATION: 1..125
        (D) OTHER INFORMATION: /note= "Mouse monoclonal antibody B5 Fv
           Heavy chain region"

(xi) SEQUENCE DESCRIPTION: SEQ ID NO:65:

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Gly Gly Gly Ser Thr Tyr Tyr Pro Asp Thr Val
    50                  55                  60

Lys Gly Arg Phe Thr Ile Asp Arg Asp Asn Ala Lys Asn Thr Leu Tyr
65                  70                  75                  80

```
Leu Gln Met Ser Arg Leu Lys Ser Glu Asp Thr Ala Met Tyr Tyr Cys
            85                  90                  95

Ala Arg Gly Leu Ser Asp Gly Ser Trp Phe Ala Tyr Trp Gly Gln Gly
            100                 105                 110

Thr Leu Val Thr Val Ser Ser Gly Gly Gly Ser Gly
            115                 120             125
```

(2) INFORMATION FOR SEQ ID NO:66:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:66:

```
Glu Val Lys Leu Val Glu Ser Gly Gly Gly Leu Val Gln Pro Gly
1               5                   10                  15
```

(2) INFORMATION FOR SEQ ID NO:67:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Region
        (B) LOCATION: 1..125
        (D) OTHER INFORMATION: /note= "Mouse monoclonal antibody B5 Fv
            Light chain region"

(xi) SEQUENCE DESCRIPTION: SEQ ID NO:67:

```
Asp Val Leu Leu Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
            85                  90                  95

Ser His Val Pro Phe Thr Phe Gly Ser Gly Thr Lys Leu Glu Ile Lys
            100                 105                 110

Arg Ala Asp Ala Ala Pro Thr Val Ser Ile Phe Pro Pro
            115                 120                 125
```

(2) INFORMATION FOR SEQ ID NO:68:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:68:

```
Asp Val Leu Leu Thr Gln Thr Pro Leu Ser Leu Pro Val Ser Leu
1               5                  10                  15
```